United States Patent [19]

Kondo et al.

[11] Patent Number: 4,626,338
[45] Date of Patent: Dec. 2, 1986

[54] EQUIPMENT FOR DETECTING OXYGEN CONCENTRATION

[75] Inventors: Haruyoshi Kondo; Keiichi Saji; Takashi Takeuchi, all of Aichi, Japan

[73] Assignee: Kabushiki Kaisha Toyota Chuo Kenkyusho, Aichen, Japan

[21] Appl. No.: 373,257

[22] Filed: Apr. 29, 1982

[30] Foreign Application Priority Data

| May 1, 1981 | [JP] | Japan | 56-65180 |
| May 25, 1981 | [JP] | Japan | 56-78029 |
| May 25, 1981 | [JP] | Japan | 56-78030 |
| May 25, 1981 | [JP] | Japan | 56-78031 |
| May 25, 1981 | [JP] | Japan | 56-78033 |

[51] Int. Cl.[4] .................. G01N 27/46; G01N 27/58
[52] U.S. Cl. .................. 204/406; 204/1 T; 204/408; 204/425; 204/426; 204/429; 204/432; 204/421
[58] Field of Search .............. 204/406, 408, 412, 421, 204/424, 425, 426, 427, 429, 431, 432, 1 S, 1 Y; 123/440, 489, 589; 60/276; 364/497

[56] References Cited

U.S. PATENT DOCUMENTS

| 4,107,019 | 8/1978 | Takao et al. | 204/425 |
| 4,264,425 | 4/1981 | Kimura et al. | 204/429 |
| 4,301,807 | 12/1981 | Mentelos | 204/408 |
| 4,356,065 | 10/1982 | Dietz | 204/1 S |
| 4,366,039 | 12/1982 | Uchida et al. | 204/1 S |
| 4,376,026 | 3/1983 | Hoffmann et al. | 204/408 |
| 4,391,691 | 7/1983 | Linder et al. | 204/426 |
| 4,419,190 | 12/1983 | Dietz et al. | 204/425 |

Primary Examiner—John F. Niebling
Assistant Examiner—B. J. Boggs, Jr.

[57] ABSTRACT

This oxygen concentration detector employs an oxygen concentration sensor provided with a plate produced of a material which exhibits ionic conduction for oxygen (An oxygen ionic conductor), a cathode placed on the one surface of the oxygen ionic conductor plate, an anode placed on the other surface of the oxygen ionic conductor plate, and a porous material layer which functions to regulate the flow of oxygen which passes through the porous material layer to reach the cathode and the oxygen ionic conductor plate. The improvement realized in this oxygen concentration detector is to remove a drawback in which the output of this sensor makes an error depending on the temperature of a gas of which the oxygen concentration is measured. This oxygen concentration detector is provided with a limiting electric current type oxygen concentration sensor, a means for applying a voltage to the sensor for the purpose to measure a limiting current flowing in the sensor, a means for measuring a current which flows in the sensor responsive to the application of a voltage to the sensor, a means for measuring the internal resistance of the sensor, and a means for regulating at least one of the foregoing three means including a limiting electric current type oxygen concentration sensor, a means for applying a voltage to the sensor and a means for measuring a current flowing in the sensor, flowing the amount of the internal resistance of the sensor detected by the foregoing means for measuring the internal resistance of the sensor.

30 Claims, 59 Drawing Figures

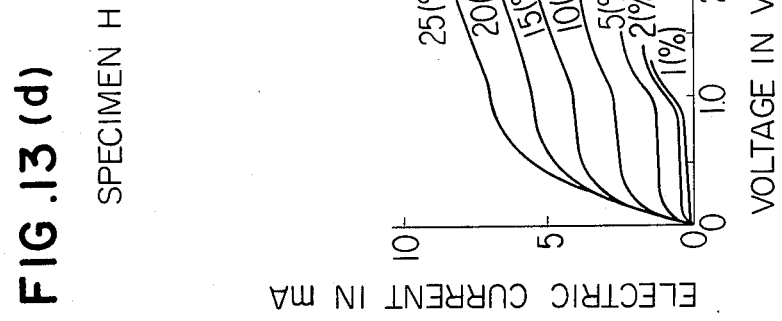
FIG.13 (d) SPECIMEN H
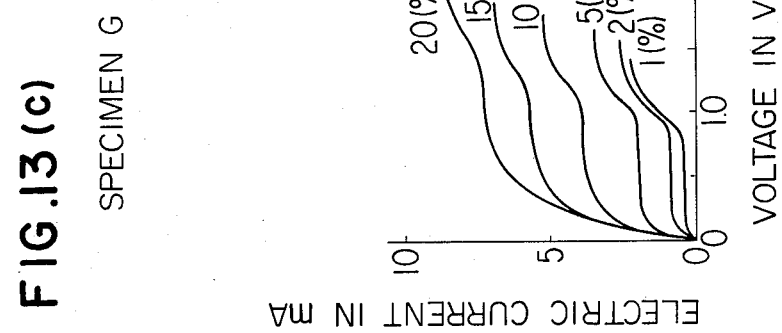
FIG.13 (c) SPECIMEN G
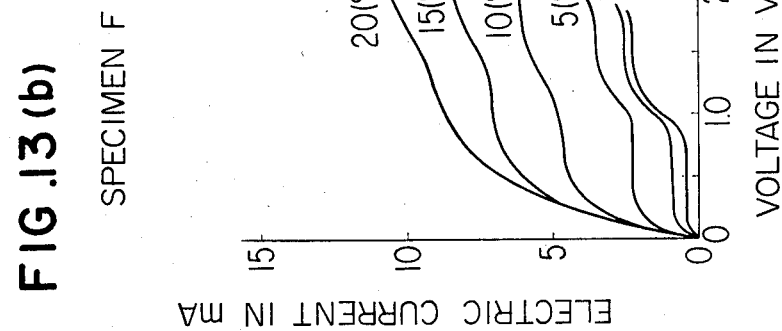
FIG.13 (b) SPECIMEN F
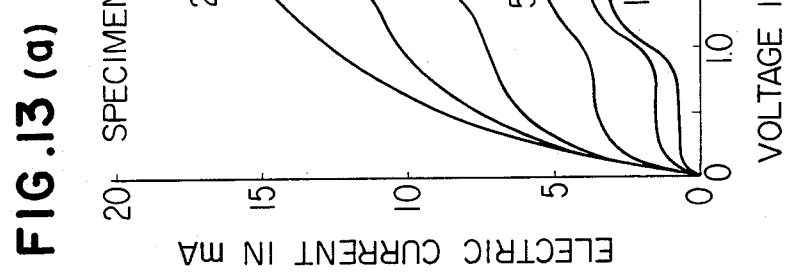
FIG.13 (a) SPECIMEN E

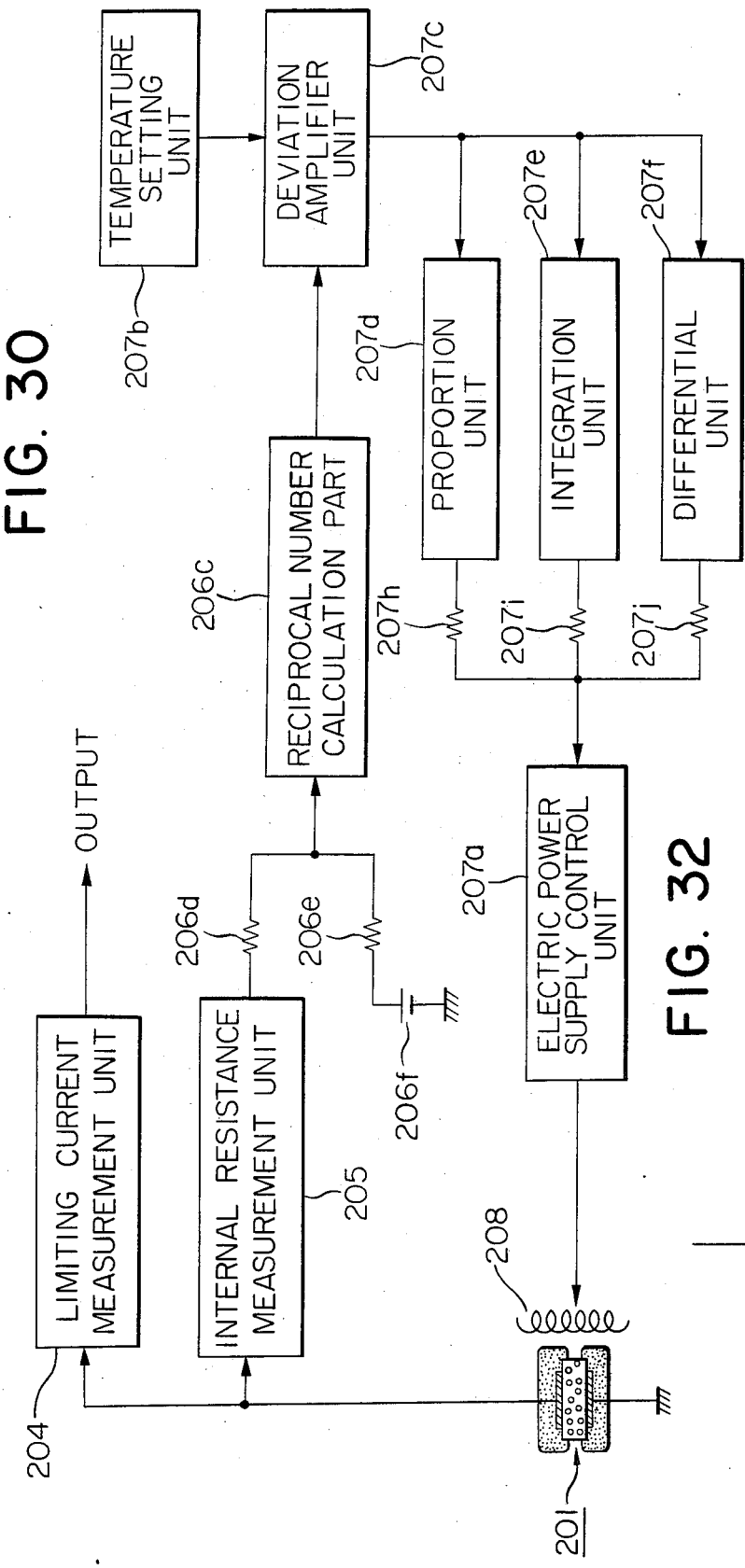
FIG. 30
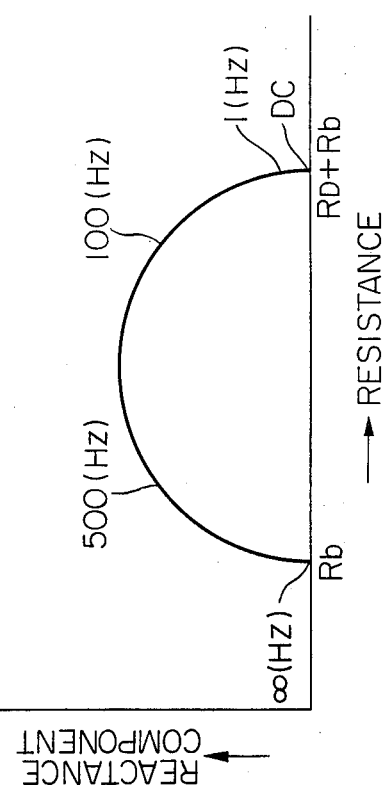
FIG. 33
FIG. 32

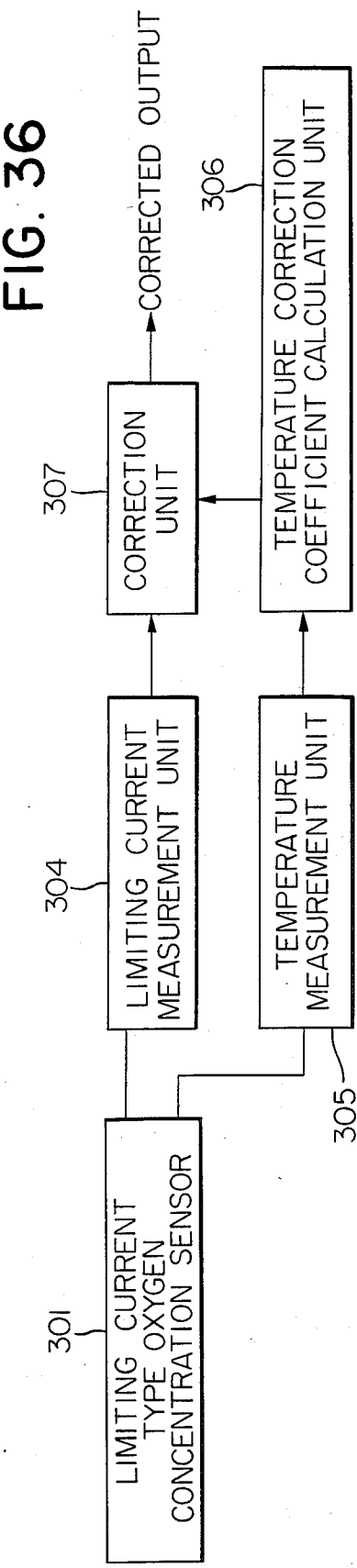
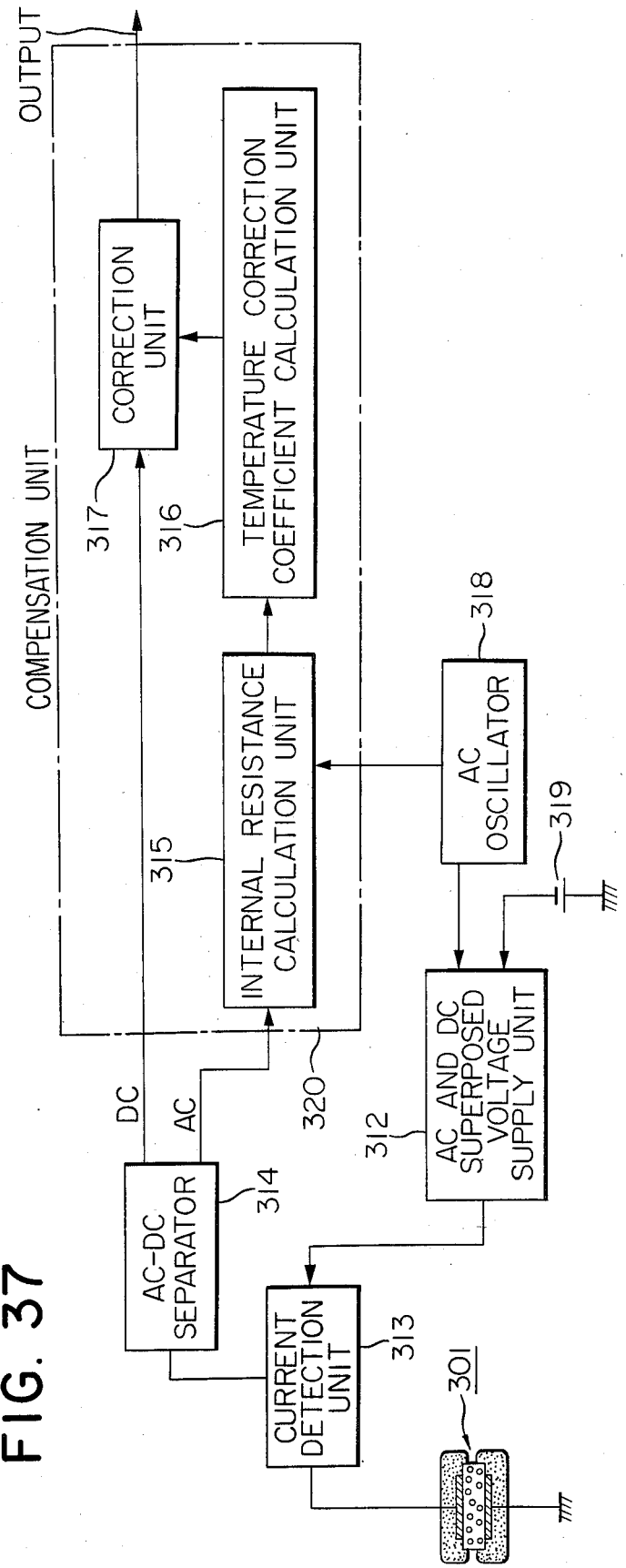

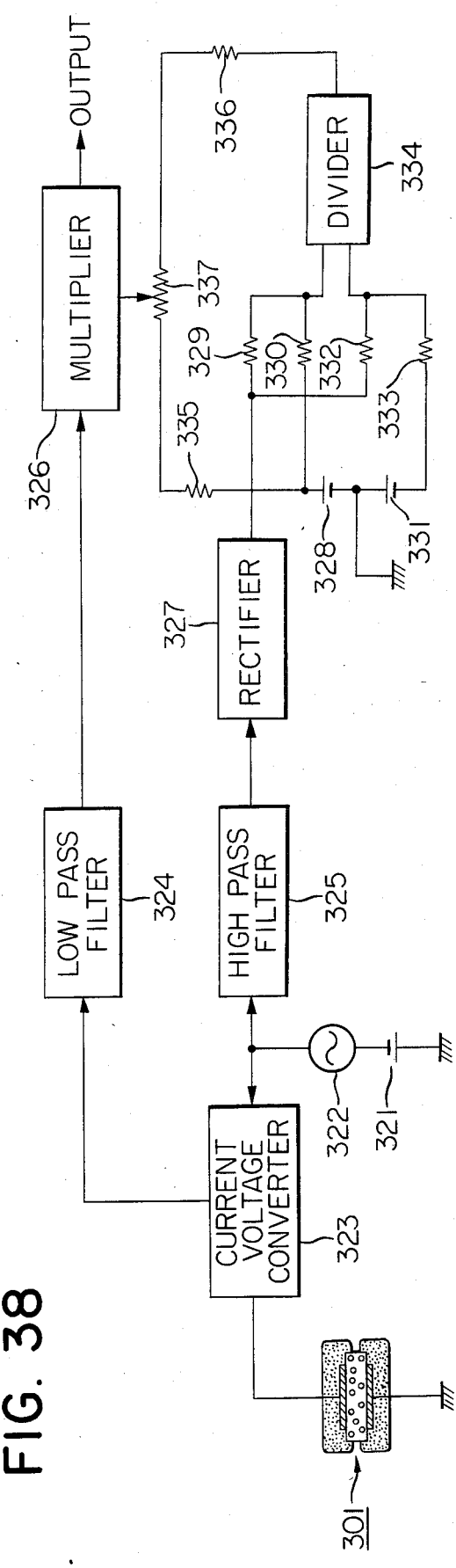
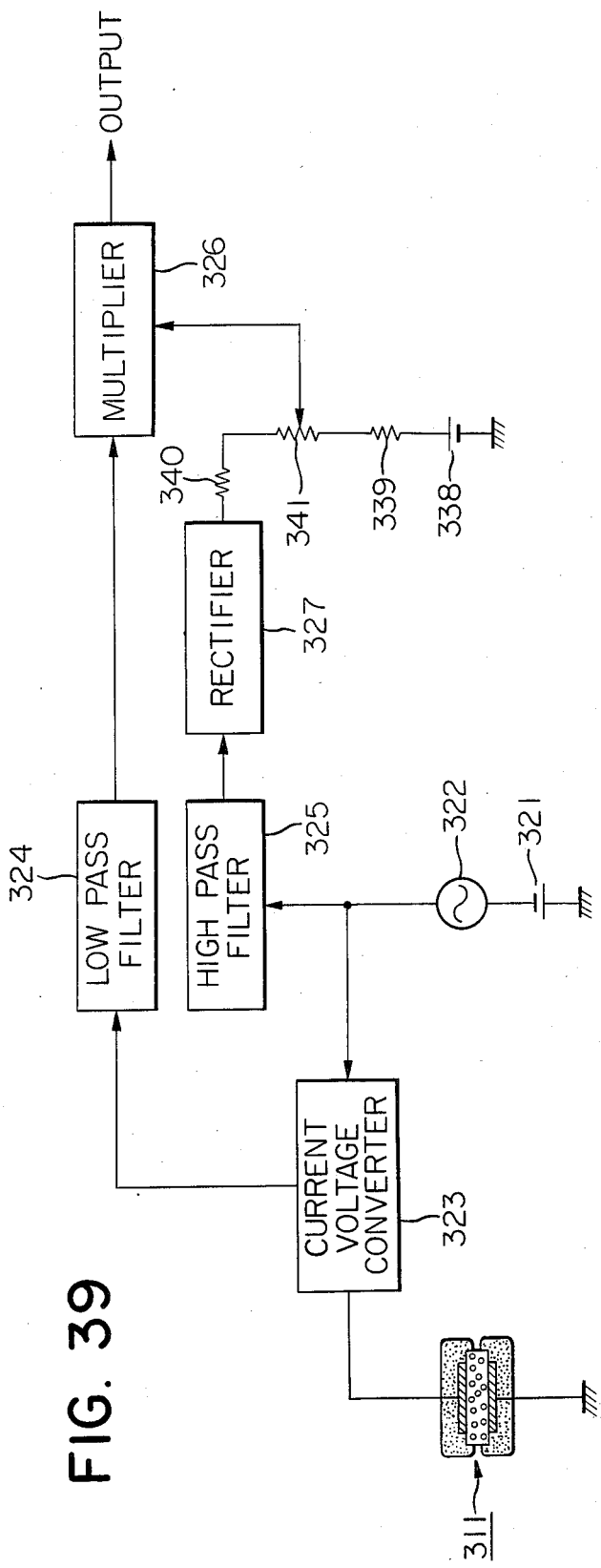
FIG. 38
FIG. 39

EQUIPMENT FOR DETECTING OXYGEN CONCENTRATION

FIELD OF THE INVENTION

This invention relates to equipment employable for detecting the concentration of oxygen contained in a gas, and more particularly to equipment for detecting oxygen concentration employing an oxygen sensor which is based on a combination of principles one of which is that a material which exhibits ionic conduction for oxygen, such as zirconium dioxide, hafnium dioxide, thorium dioxide, dibismuth trioxide et al. exhibits an electric current vs. voltage relation which depends on a parameter which is the concentration of oxygen available in the neighborhood of such a material and the other of which is that the foregoing electric current vs. voltage relation has a tendency to saturate in a certain voltage range, in which the amount of current is limited, thereby the concentration of oxygen available in the neighborhood of a cathode which supplies oxygen ions toward such an oxygen ionic conductive material or an oxygen ionic conductor, can be precisely detected with a quick-response time by measurement of the saturated current or the limiting current which flows in the oxygen ionic conductor under a condition where oxygen is available in the neighborhood of the oxygen ionic conductor at a certain amount of concentration. Needless to emphasize, the foregoing features enable the foregoing limiting current type equipment for detection of oxygen concentration to be employed for the purpose of detecting the concentration of oxygen contained in exhaust gases emitted by boilers installed in thermal powerstations, internal combustion engines mounted on cars et al.

BACKGROUND OF THE INVENTION AND STATEMENT OF THE PRIOR ARTS

Various types of combustion equipment and absolutely essential for human life. For example, boilers installed in thermal powerstations supply electric power and various types of internal combustion engines are mounted on cars which are one of the major transportation means in modern society. Unfortunately, however, this combustion equipment is inevitably accompanied by the possibility of emission of a considerable quantity of injurious gases, depending on the condition in which the combustion takes place. Therefore, a long standing strong requirement is recognized for the development of combustion equipment which is free from the air contamination problem, in addition to the traditional requirement for development of combustion equipment having a higher combustion efficiency and which requires less quantity of fuel for generating a unit quantity of energy. Further, it is recognized that a new requirement has come out for development of a technology for cleaning the air contaminated with injurious gases.

It is believed that combustion of a lean fuel or combustion of a mixture of a less quantity of a gaseous fuel and a larger quantity of air is effective to simulaneously satisfy both requirements for a decreased emission of injurious gases and for an increased combustion efficiency of a combustion equipment. For example, it is publicly known that a lean fuel mixture (hereafter lean fuel) is preferably employed for a Diesel engine. Therefore, it is hopefully assumed that a lean fuel could be employed for a gasoline engine to satisfy the foregoing objects.

However, mixture containing a fuel and air at an undersired content ratio readily causes such engines to exhaust a considerable quantity of soot and/or causes misfiring, despite the fact that such engines inherently prefer a lean fuel, causing various problems including the air pollution problem due to the emission of soot or the unburned fuel and the less satisfactory magnitude of combustion efficiency. In other words, such a mis-use of a lean fuel is not only ineffective to satisfy the foregoing objects but also involved with a possibility that it causes various reverse effects. Therefore, adjustment of the ratio of fuel and air is an extremely important item to allow combustion equipment to operate under satisfactory conditions. It is quite true for any type of control system that the accurate and quick detection of an object to be controlled (in this case, the ratio of fuel and air in a range in which the fuel ratio is relatively small.) is essential for performance of the control system. Unfortunately, however, none of the sensors which are at present available in the prior art is satisfactory for the foregoing purposes. For example, the magnetic oxygen concentration detector is unsatisfactory for the purpose to be employed under a condition wherein the detector is mounted on a car, because of its rather slow response speed. The density type sensor or the thermal conductivity type sensor is also unsatisfactory for the purpose to control the combustion of an internal engine, because the accuracy thereof is inclined to be infuenced even by a marginal quantity of hydrogen ($H_2$) contained in the gas.

The known equipment for detecting oxygen concentration are represented by a limiting electric current type oxygen concentration detector which was invented by the inventors of this invention and was laid open to public inspection under the Laying-open of Application No. Toku-Kai-Sho No. 52-72286 in Japan and which disclosed the conceptual construction of the limiting electric current type oxyten concentration detector and by another limiting electric current type oxygen concentration detector which was invented by the inventors of this invention and was filed under the application No. 55-123677 in Japan which disclosed an improvement applied to the foregoing conceptual construction or an improved construction of a limiting electric current type oxygen concentration detector of which the cathode is covered by a porous material.

Either of these limiting current type oxygen concentration detectors is free from various drawbacks which are inevitably involved with the oxygen concentration detector available in the prior art. From this viewpoint, either of these limiting current type oxygen concentration detector is recognized as an oxygen concentration detector having an excellent feature. From other view points, however, either of the foregoing limiting current type oxygen concentration detectors is involved with possibilities of further improvement. It is quite often than internal combustion engines vary the temperature of their exhaust gas depending on the corresponding operating conditions. Therefore, a limiting current type oxygen concentration detector is required to have a stable performance in a relatively wide range of oxygen concentration, when it is employed as a detector for an exhaust gas. However, a limiting current type oxygen concentration detector is inclined to vary the oxygen concentration vs. the limiting current relations depending on the temperature of the sensor even under a constant voltage applied thereto. As a result, the limiting current type oxygen concentration detector is involved with a considerable amount of error caused by variation of the temperature of a gas and the oxygen concentration range in which the reliable measurement is available, is fairly limited. Further, the limiting current type oxygen concentration detector has a tendency, under a constant oxygen concentration, to sharply decrease the amount of the limiting current following a decrease in temperature in a low temperature range, which reduces the temperature range in which reliable operation is allowed. This sharp decrease of the limiting current in a low temperature range is caused by an increase of the internal resistance of the oxygen sensor.

OBJECTS AND SUMMARY OF THE INVENTION

An object of this invention is to provide a limiting electric current type oxygen concentration detector wherein improvements are realized to prohibit an error caused by the variation in temperature thereof and an error caused by variation of the internal resistance thereof due to the variation in temperature thereof and to widen the temperature range and the oxygen concentration range in which the measurement is allowed.

To achieve the foregoing object, a limiting electric current type oxygen concentration detector in accordance with this invention is provided with (a) a limiting electric current type oxygen concentration sensor, (b) a means for applying a voltage to the foregoing limiting electric current type oxygen concentration sensor to measure a limiting electric current of the foregoing limiting electric current type oxygen concentration sensor, (c) a means for measuring electric current flowing in the foregoing limiting electric current type oxygen concentration sensor responsive to the application of the voltage to the limiting electric current type oxygen concentration sensor, (d) a means for detecting the internal resistance of the limiting electric current type oxygen concentration sensor, and (e) a means for regulating at least one of the aforesaid i.e. the limiting electric current type oxygen concentration sensor, the means for applying voltage to said limiting electric current type oxygen concentration sensor and the means for measuring the electric current flowing in the limiting electric current type oxygen concentration sensor, following the detection of internal resistance by limiting electric current type oxygen concentration detector in accordance with the first embodiment of this invention with which an accurate measurement for oxygen concentration is allowed regardless of a variation of the temperature of a gas of which the oxygen concentration is measured, is provided with a means for regulating the temperature of a limiting electric current type oxygen sensor, following the temperature of the oxygen sensor which is determined by means of detection of the internal resistance of the oxygen sensor. More specifically, this limiting current type oxygen concentration detector is provided with (a) a limiting electric current type oxygen concentration sensor, (b) a means for detecting the internal resistance of the foregoing limiting electric current type oxygen concentration sensor, (c) a means for regulating the temperature of the foregoing limiting electric current type oxygen concentration sensor for the purpose to maintain the temperature unchanged, and (d) a means for measuring the limiting electric current of the foregoing limiting electric current type oxygen concentration sensor.

A limiting electric current type oxygen concentration detector in accordance the second embodiment of this invention is provided with a means for applying temperature compensation to the output of the limiting electric current type oxygen concentration sensor, following the temperature of the oxygen sensor which is determined by means of detection of the internal resistance of the oxygen sensor. More specifically, this limiting current type oxygen concentration detector is provided with (a) a limiting electric current type oxygen concentration sensor, (b) a means for applying a voltage to the foregoing limiting electric current type oxygen concentration sensor to measure a limiting electric current of the foregoing limiting electric current type oxygen concentration sensor, (c) a means for measuring an electric current flowing in the foregoing limiting electric current type oxygen concentration sensor, (d) a means for applying a voltage to or for flowing an electric current in the foregoing limiting electric current type oxygen concentration sensor to measure the internal resistance of the foregoing limiting electric current type oxygen concentration sensor, (e) a means for measuring the internal resistance of the foregoing limiting electric current type oxygen concentration sensor, (f) a means for calculating a temperature compensation coefficient, following the internal resistance of the foregoing limiting electric current type oxygen concentration sensor determined by means of the foregoing means for measuring the internal resistance of the foregoing limiting electric current type oxygen concentration sensor, and (g) a means for correcting the output of the foregoing means for measuring electric current flowing in the limiting electric current type oxygen concentration sensor, following the output of the means for calculating a temperature compensation coefficient.

A limiting electric current type oxygen concentration detector in accordance with the third embodiment of this invention wherein occurrence of errors caused by variation of the internal resistance which variation is further caused by variation of the temperature of an oxygen sensor and particularly occurrence of errors caused by an increase in the internal resistance of the oxygen sensor are effectively prohibited particularly in the low temperature range, is provided with (a) a limiting electric current type oxygen concentration sensor, (b) a means for applying a voltage to the limiting electric current type oxygen concentration sensor to measure a limiting electric current of the foregoing limiting electric current type oxygen concentration sensor, (c) a means for measuring an electric current flowing in the limiting electric current type oxygen concentration sensor, and (d) a means to compensate the amount of voltage which is applied to the limiting electric current type oxygen concentration sensor by means of the foregoing means for applying a voltage to the limiting electric current type oxygen concentration sensor to measure a limiting electric current of the limiting electric current type oxygen concentration sensor, following the voltage drop caused by the internal resistance of the limiting electric current type oxygen concentration sensor.

Another object of this invention is to provide a means for detecting the internal resistance of a limiting electric current type oxygen concentration sensor which is assembled in a limiting electric current type oxygen concentration detector in accordance with this invention. Albeit measurement of an internal resistance requires a voltage applied to or an electric current flowing in an oxygen concentration sensor, it is not easy to satisfy this requirement, because a limiting electric current type oxygen concentration sensor has only two terminals which are employed for measurement of the limiting electric current of the oxygen concentration sensor.

To achieve the foregoing object, a means for detecting the internal resistance of a limiting electric current type oxygen concentration sensor in accordance with the first embodiment of this invention is based on an idea that an alternating current is employed to detect the internal resistance of the oxygen concentration sensor and that the alternating current is superposed on the direct current voltage which is employed for detection of the limiting current of the oxygen concentration sensor. More specifically, this means for detecting the internal resistance of a limiting electric current type oxygen concentration sensor is provided with (a) a means for applying a voltage or for supplying an electric current containing an alternating current superposed on a direct current, to a limiting electric current type oxygen concentration sensor, (b) a means to split the alternating current component and the direct current component from the current flowing in the limiting electric current type oxygen concentration sensor and which contains both components, (c) a means for detecting the limiting electric current from the direct current component, and (d) a means for detecting the internal resistance from the alternating current component.

A means for detecting the internal resistance of a limiting electric current type oxygen concentration sensor in accordance with the second embodiment of this invention is based on an idea in which a time sharing system is employed for alternating application of two independent voltages the one of which is for detecting limiting current and the other of which is for detecting the internal resistance of the sensor A means for detecting the internal resistance of a limiting electric current type oxygen concentration sensor in accordance with the third embodiment of this invention is based on an idea that a component for detecting the internal resistance of the limiting electric current type oxygen concentration sensor is provided in the oxygen concentration sensor so that the oxygen concentration sensor has three or four terminals. More specifically, this means for detecting the internal resistance of a limiting electric current type oxygen concentration sensor is provided with (a) a component for detecting a limiting electric current by means of an application of a voltage selected from the range which is under the influence of an excess voltage and which is provided with an oxygen ionic conductor having a cathode arranged on one surface thereof and an anode arranged on the other surface thereof and (b) a component for detecting the internal resistance of the sensor by means of an application of a voltage or of a supply of an electric current which is selected from the range which is under the influence of a resistance and which is composed of a portion of the foregoing oxygen ionic conductor and of an electrode layer arranged thereon.

The above and other objects, advantages and features of this invention will become more apparent from the following description of the foregoing and other embodiments thereof presented in conjunction with the accompanying drawings.

BRIEF DESCRIPTION OF THE DRAWINGS

FIGS. 13(a)–(d) are is a set of graphs showing the electric current vs. voltage relations employing the oxygen concentration as a parameter, of four different limiting electric current type oxygen concentration sensors of which the conceptual configuration is shown in FIG. 12 and each of which has a different diameter thereof, FIG. 30 is a block diagram of a limiting electric current type oxygen concentration detector in accordance with the third modification of the first embodiment of this invention wherein the calculation system is extremely simplified, FIG. 32 is a graph showing the locus of frequency responsive to variation of each component of impedance of a marginal amount of voltage (current) in the excess voltage domination range applied to a limiting current type oxygen concentration sensor, FIG. 33 is an equivalent circuit representing the characteristics shown in FIG. 32, FIG. 20 is provided, FIG. 36 is a block diagram showing the fundamental construction of a limiting electric current type oxygen concentration detector in accordance with the second embodiment of this invention, FIG. 37 is a block diagram of a limiting electric current type oxygen concentration detector in accordance with one modification of the second embodiment of this invention wherein alternative current is employed for measurement of the internal resistance of a limiting electric current type oxygen concentration sensor, FIG. 38 is a block diagram of a limiting electric current type oxygen concentration detector in accordance with another modification of the second embodiment of this invention of which the temperature correction coefficient calculation unit is composed employing the formula 22, FIG. 39 is a block diagram of a limiting electric current type oxygen concentration detector in accordance with the third modification of the second embodiment of this invention of which the temperature correction coefficient calculation unit is composed employing the formula 25, FIG. 20 is provided, FIG. 42 is a block diagram showing the fundamental construction of a limiting electric current type oxygen concentration detector in accordance with the third embodiment of this invention wherein a limiting current type oxygen concentration sensor having a portion for measuring the internal resistance thereof in addition to a portion for measuring the limiting current thereof is provided.

DETAILED DESCRIPTION

OXYGEN CONCENTRATION SENSOR EMPLOYED FOR THE PRESENT INVENTION

The oxygen concentration sensor which is employed for a limiting electric current type oxygen concentration detector in accordance with this invention will be described below.

(a) Limiting electric current type oxygen concentration sensor

Figure 1:
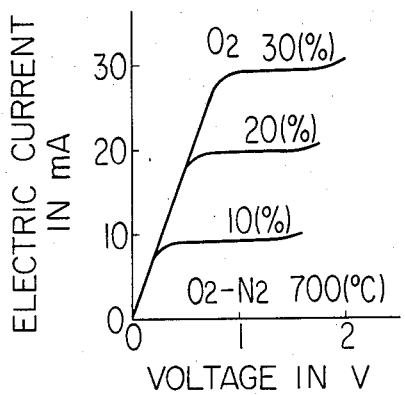
FIG. 1 is a graph showing the electric current vs. voltage relations employing the oxygen concentration as a parameter, of a limiting electric current type oxygen concentration sensor.

A limiting electric current type oxygen concentration sensor is a sensor for sensing the concentration of oxygen contained in a gas, the sensor being provided with (a) a plate produced of an ionic conductor or of a substance which exhibits the ionic conduction phenomenon for oxygen (b) a set of an anode and a cathode arranged respectively along either surface of the oxygen ionic conductor plate to be applied positive and negative voltages respectively, and (c) a means for regulation of the diffusion rate of oxygen which is arranged to cover the cathode to limit the quantity of oxygen diffused toward the cathode; thereby the concentration of oxygen contained in the gas is determined by means of detection of the amount of electric current flowing through the oxygen ionic conductor plate across the anode and cathode. FIG. 1 shows the electric current vs. voltage characteristics of an oxygen concentration sensor provided with a means for regulation of the diffusion rate of oxygen which is a plate of a replete material provided with a number of minute perforations. A voltage of the magnitude of 1 volt applied to an oxygen concentration sensor element having the characteristics shown in the figure causes an electric current of which the intensity is proportional to the concentration of oxygen contained in a gas. Since this type of oxygen concentration sensor has various advantages including (a) that it does not require a reference gas having a reference oxygen concentration, (b) that it has linear characteristics of the oxygen concentration vs. electric current, (c) that it is scarcely influenced by the temperature variation, and (d) that it is scarcely influenced by hysteresis, it can be employed for measurement of relatively higher concentrations of oxygen.

The saturated electric current characteristics (Hereinafter referred to as the limiting electric current characteristics.) shown in FIG. 1 is accounted for as follows.

An electric current flowing in an oxygen concentration sensor element having an oxygen ionic conductor plate provided with an anode and a cathode arranged respectively along either surface of the plate, ionizes oxygen available in the neighborhood of the cathode. The oxygen ions which have passed through the oxygen ionic conductor plate are deionized along the surface of the anode. The deionized oxygen is purged out of the element. It is clear that no electric current flows in the element, unless oxygen gas is supplied in the neighborhood of the cathode. Incidentally, a limitation applied to the quantity of oxygen gas to be supplied to the neighborhood of the cathode is accompanied by a limitation of the electric current flowing in the oxygen ionic conductor. A gradual increase in the voltage applied to the element is accompanied by the corresponding increase in the electric current until the amount of electric current reaches the amount corresponding to the maximum quantity of oxygen supplied to the cathode. This means that an increase in the voltage does not cause the corresponding increase in the electric current in excess of the amount of electric current corresponding to the quantity of oxygen supplied to the cathode. This saturated amount of electric current is defined as the limiting electric current. It is noted that the oxygen concentration becomes marginal in the geometrical area close to the cathode in this voltage range. As a result, the relations between the electric current and the voltage becomes as shown in FIG. 1. Albeit an oxygen concentration sensor provided with a means for regulation of the diffusion rate of oxygen which means is a plate of a replete material provided with a number of minute perforations, exhibits an excellent performance in detection of the oxygen concentration, it is involved with a costwise disadvantage, because it requires arrangement of a means for regulation of the diffusion rate of oxygen on an oxygen ionic conductor plate, after these two members are independently produced.

Figure 2:
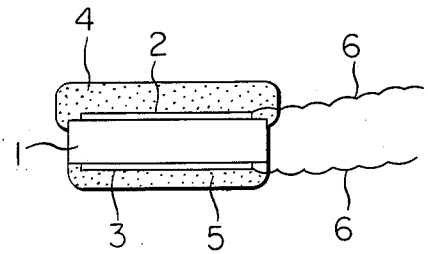
FIG. 2 is a side view of a limiting electric current type oxygen concentration sensor provided with a cathode covered by a layer of a porous material.

(b) Limiting electric current type oxygen concentration sensor provided with a means for regulation of the diffusion rate of oxygen produced of a porous material FIG. 2 shows the schematic configuration of one example of an oxygen concentration sensor based on the foregoing limiting electric current characteristics (Hereinafter referred to as a limiting electric current type oxygen concentration sensor or simply as an oxygen sensor.) and which is provided with a means for regulation of the diffusion rate of oxygen produced of a porous material. The oxygen sensor illustrated in FIG. 2 is provided with an oxygen ionic conductor 1, with a cathode 2 and an anode 3 provided respectively along either surface of the oxygen ionic conductor 1, and with a layer of a porous material 4 which covers the cathode 2. The amount of the limiting electric current is determined by the degree at which the layer of a porous material 4 allows a gas to penetrate it. The oxygen sensor is further provided with a protective layer of a porous material 5 which covers the anode 3 to protect the anode 3 from contaminative substances contained in a gas of which the oxygen concentration is measured, such as soot, uncombusted fuel, et al, and with lead wires 6 drawn from the cathode 2 and the anode 3. The oxygen sensor element having this schematic configuration has various advantages that (a) it is simple in construction, (b) it is less expensive in production cost thereof in comparison with the foregoing oxygen sensor provided with a means for regulation of the diffusion rate of oxygen which is a plate of a replete material provided with a number of minute perforations, and (c) it is suitable to be assembled in machines et al., such as automobiles, each of which has an inherent nature to be mass-produced. However, the oxygen sensor element having the schematic configuration shown in FIG. 2 has the electric current vs. voltage characteristics shown in FIG. 3. Referring to the figure, a voltage range in which a displacement of electric current scarcely causes the corresponding displacement of electric current which is defined as a voltage range, can not be clearly observed wherein the current is to saturate, in the high oxygen concentration range. In other words, it becomes difficult to recognize the amount of the limiting current which is the saturated electric current in the saturated current voltage range in the high oxygen concentration range in which the oxygen concentration exceeds 5 (%).

Figure 5:
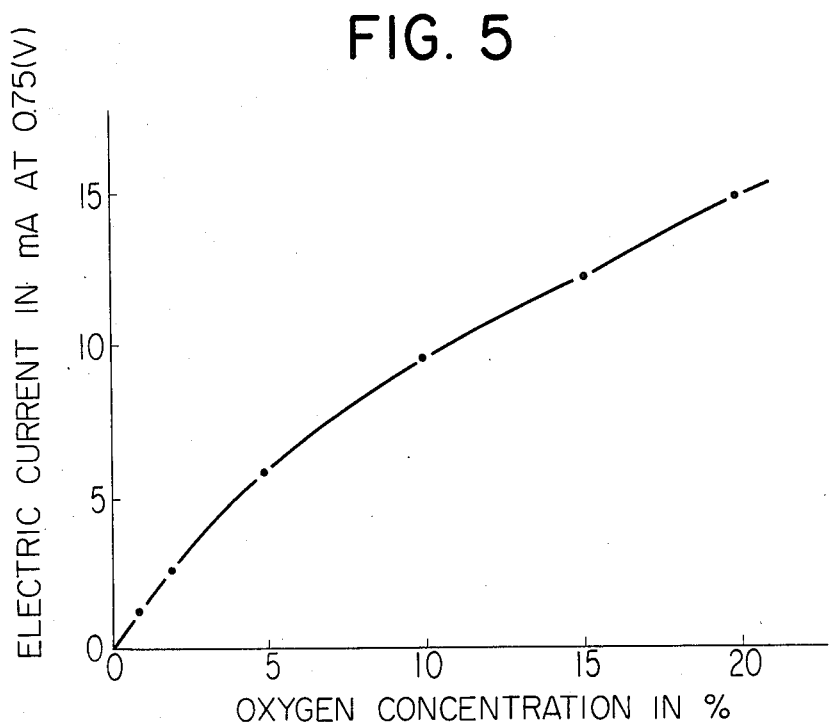
FIG. 5 is a graph showing the electric current vs. oxygen concentration relations of a limiting electric current type oxygen concentration sensor of which the conceptual configuration is shown in FIG. 2.

Supposing that the sensor output current is defined as an electric current which flows in an oxygen sensor which is applied a voltage in the range of 0.7 through 1 V, the foregoing phenomenon turns out to cause an adverse effect for the linearity of the output current vs. oxygen concentration characteristics of the oxygen sensor in the high oxygen concentration range, as shown in FIG. 5.

Figure 3:
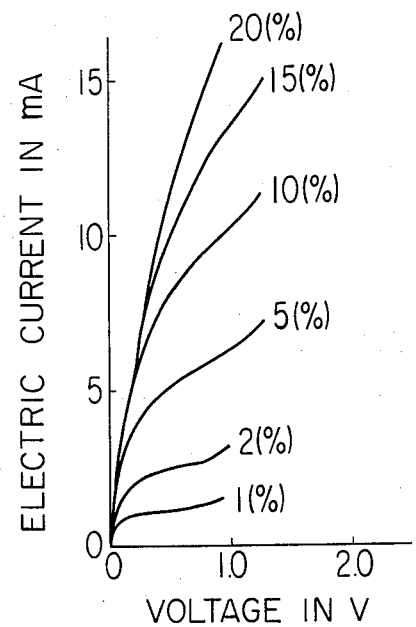
FIG. 3 is a graph showing the electric current vs. voltage relations employing the oxygen concentration as a parameter, of a limiting electric current type oxygen concentration sensor of which the conceptual configuration is shown in FIG. 2.

The unsatisfactory characteristics of which an example is shown in FIG. 5 to represent the relations of the output current vs. the oxygen concentration is accounted for as follows. The oxygen sensor element having the schematic configuration shown in FIG. 2 is provided with the layer of a porous material 4 which is arranged to cover the cathode 2. This means that a number of minute open spaces are available along the surface of the cathode 2 and that these minute open spaces are interconnected with the atmosphere outside the layer of a porous material 4 through a number of paths whose directions vary from one another like a maze. This further means that some portion of the gas of which the oxygen concentration is measured arrives at the cathode 2 in the direction perpendicular to the surface of the cathode 2 and some portion in the direction parallel to the surface of the cathode 2. The latter portion which proceeds parallel to the surface of the cathode 2 flows into the side portion of the porous material 4 from the atmosphere outside of the oxygen sensor element, before it arrives at the cathode 2 and proceeds along the surface of the cathode 2. Thus, the gas of which the oxygen concentration is measured diffuses through a maze of a number of minute open spaces which are available along the surface of the cathode 2 or in the neighborhood of the cathode 2. The oxygen contained in the gas of which the oxygen concentration is measured and which has arrived at the surface of the cathode 2 is, as described above, ionized and converted to oxygen ions, which move in the oxygen ionic conductor 1 toward the anode 3. Therefore, the cathode 2 can be interpreted to absorb oxygen. If the density of oxygen ions which travel from the cathode 2 toward the oxygen ionic conductor 1 or the current density is uniform throughout the entire surface of the cathode 2, the volume of oxygen absorbed by the cathode 2 is uniform throughout the entire surface of the cathode 2. However, oxygen is absorbed from the gas of which the oxygen concentration is measured during the period in which the gas proceeds from the peripheral portion of the cathode 2 toward the center portion of the cathode 2. Accordingly, the oxygen concentration contained in the gas available along the cathode 2 turns out to be less around the center portion of the cathode 2 with a graded increase toward the peripheral portion, insofar as the gas supplied from the side of the element in the horizontal direction is concerned. On the other hand, the oxygen concentration is uniform along the surface of the cathode 2 insofar as the gas supplied from the top of the element in the vertical direction is concerned. As a result, the overall oxygen concentration of the gas available along the surface of the cathode 2 is less around the center portion of the cathode 2 with a graded increase toward the peripheral portion. When a current which flows across the oxygen ionic conductor 1 gradually increases upto a level slightly less than the limiting current, the oxygen concentration becomes marginal around the center portion of the cathode due to the foregoing characteristic distribution of the oxygen concentration along the surface of the cathode, albeit the corresponding amount remains high in the peripheral portion of the cathode. In other words, an extreme magnitude of non-uniformity is observed for the oxygen concentration along the cathode. The foregoing description is based on an assumption that the density of electric current flowing from the cathode to the oxygen ionic conductor is uniform for the entire area of the cathode. In reality, however, a more amount of current flows in the peripheral region of the cathode where a larger oxygen concentration is available than in the center portion of the cathode where the oxygen concentration is limited. As a result, non-uniformity of the electric current density is observed along the surface of the cathode. This larger magnitude of current density in the peripheral region of the cathode is effective to decrease the oxygen concentration there. As a result, the foregoing assumed magnitude of non-uniformity of the oxygen concentration is decreased to some limited extent. However, this non-uniformity of the oxygen concentration actually remains on the overall basis, because the electric resistance of an oxygen ionic conductor is effective to limit the foregoing non-uniformity of current density. Accordingly, the foregoing non-uniformity of the oxygen concentration remains along the surface of the cathode, and the oxygen concentration is higher in the center region of the cathode than in the peripheral region of the cathode. An electric current slightly less than the limiting current is effective to saturate the electric current at the center region of the cathode where the oxygen concentration is marginal. However, such a magnitude of electric current is not effective to saturate the electric current at the peripheral region of the cathode where the oxygen concentration is high. As a result, the amount of electric current continues to increase following an increase of voltage applied to the element. This is the reason why the current vs. voltage relations do not saturate even in the voltage range wherein the electric current is to saturate, as shown in FIG. 3. This insufficient saturation of or relatively large increase rate of the electric current in the voltage range wherein the electric current is to saturate (the flat current voltage range), has an adverse effect for the linearity of the characteristics for detection of the oxygen concentration. The reason of this adverse effect will be described below, referring to FIG. 4. An oxygen sensor is applied a voltage Vs, shown as oc in the figure, to cause an output current to flow therein. The incline of the straight line ao represents the linear increase rate of the current which flows in the element in response to the gradual increase of the voltage. A straight line bc is drawn parallel to the straight line ao through a point c. This straight line crosses the curve representing the current vs. voltage relations at a point d. A straight line ce which is drawn parallel to the Y axis or the current axis through the point c crosses the curve representing the current vs. voltage relations at a point f. The point d is assumed to represent the limiting current. For the purpose to simplify the description, the following assumption is introduced. Firstly, the incline of the current vs. voltage curve is proportional to the limiting current Il in the voltage range wherein the electric current is to saturate (the flat current voltage range). In other words, the incline of the curve increases following the oxygen concentration which causes a corresponding increase of the limiting current Il, in the voltage range wherein the electric current is to saturate (the flat current voltage range). This assumption means that the foregoing non-uniformity of the electric current density distribution is maintained in the analogous situation independently from any variation of the oxygen concentration and is considered to be determined depending on the shape of the element.

Figure 4:
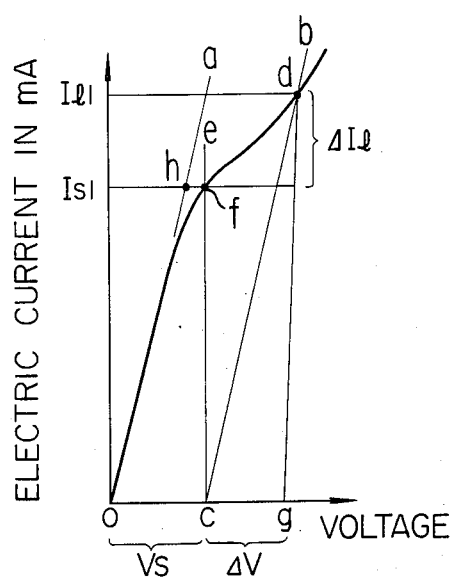
FIG. 4 is a graph employed for explanation of the electric current vs. voltage relations of a limiting electric current type oxygen concentration sensor.

Supposing that the output current of the element which is applied a specific voltage Vs is Is, this corresponds to a point f shown in FIG. 4. Albeit the Il represented by the point d should be outputted as the inherent output current of the sensor, the actual output current Is turns out to be less than Il, when the flat current voltage range fd considerably deviates from a horizontal line and has a large incline against the X axis. In other words, the amount of voltage which effectively functions for causing the limiting current characteristics is limited to an amount represented by an hf or an amount acquired by subtracting the voltage-drop generated in the oxygen ionic conductor from the specific voltage Vs, resultantly causing the amount of the output current to become less than Il. Supposing that the incline of the current flat voltage range portion is $\Delta Il/\Delta V$, this amount turns out to be proportional to the limiting current Il depending on the foregoing assumption. Namely, putting K to a coefficient which represents the incline of the current flat voltage range, $$\Delta Il/\Delta V = KIl \tag{1}$$

wherein, $\Delta V$ represents the amount of voltage-drop which is generated in an oxygen ionic conductor in which an electric current Il is flowing and which corresponds to the amount represented by cg shown in FIG. 4. Putting R to the resistance of an oxygen ionic conductor, $$\Delta V = RIl \tag{2}$$

Referring to FIG. 4, the output current Is of an oxygen sensor is:

$$Is = Il - \Delta Il \tag{3}$$

Substituting the formula (1) and (2) into this formula (3), $$Is/Il = 1 - KRIl \tag{4}$$

This formula represents the ratio of the amounts of sensor output current and of the limiting current, and the second term of the right side (KRIl) represents the deviation of the detection characteristics from the straight line or the detection error.

The foregoing description refers to a tendency inherent to an oxygen sensor having the configuration shown in FIG. 2 in which the current density is not uniform along the surface of the cathode due to a relatively large volume of oxygen which flows into the sensor from the side portion of the sensor in the horizontal direction. A large magnitude of the non-uniformity of the current density causes a large magnitude of the inclination of the current vs. voltage curve at the current flat voltage range, resulting in a large amount of K. The resistance R of an oxygen ionic conductor remains unchanged regardless of the amount of oxygen concentration. An element having a large amount of K is accompanied by a large amount of the error term under the condition where the oxygen concentration is high and the limiting current Il is large. Therefore, such an element has a tendency in which the detection performance is worsened following the increase in the oxygen concentration. Thus, an oxygen sensor having a cathode covered by a layer produced of a porous material shown in FIG. 2 is not satisfactory for the purpose to detect a wide range of oxygen concentration particularly in the high oxygen concentration range, because the sensing accuracy is unsatisfactory due to the unsatisfactory linearity of the current vs. voltage curve in the high oxygen concentration range, as shown in FIG. 4. This is the reason why the reliable range for detection of the oxygen concentration is limited to approximately 5 (%) (under 1 atmosphere) for such an oxygen sensor, as shown in FIG. 5.

The foregoing description has clarified that a large amount of lateral diffusion of gases is a major parameter which causes the unsatisfactory linearity of the current vs. voltage curve in the high oxygen concentration range shown in FIG. 3 or FIG. 5.

(c) Improvement in the limiting current type oxygen sensor

Therefore, it is expected by possible to improve the performance of the oxygen sensor shown in FIG. 2 by limiting the lateral diffusion of oxygen from the side portion of the element.

Figure 6:
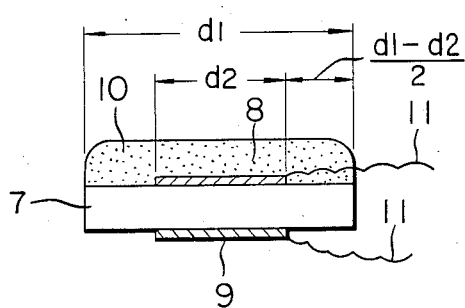
FIG. 6 is a side view of an improved model of a limiting electric current type oxygen concentration sensor.

FIG. 6 shows an example of the improved oxygen sensor. This oxygen sensor is provided with a cathode of which the area is less than the corresponding area of an oxygen ionic conductor, thereby the lateral diffusion of oxygen in the direction parallel to the surface of the cathode is limited. More specifically, the diameter of the cathode is selected to be considerably less than the corresponding diameter of the oxygen ionic conductor, thereby the contact area with which the porous layer and the oxygen ionic conductor contact each other is increased, resultantly improving the current vs. voltage characteristics of the sensor. Referring to FIG. 6, an oxygen ionic conductor 7 is put between a cathode 8 and an anode 9, and the cathode 8 is covered by a porous layer 10. One each leadwire 11 is drawn from the cathode 8 and the anode 9. The oxygen ionic conductor 7 is a disk of a replete material having a composition of $(ZrO_2)_{0.92}(Y_2O_3)_{0.08}$ and which is produced by means of sintering as described below. A mixture of zirconium dioxide ($ZrO_2$) and diyttrium trioxide ($Y_2O_3$) each of which is highly pure (in excess of 99.9 (%)) is produced to contain each substance at a mol ratio of 92:8, before a wet type ball mill is employed for crushing the mixture. After the wet mixture is dried, the dry mixture is prebaked for 10 hours at a temperature of 1,250 (°C.), before it is grounded down to a fine powder in an agate mortar. A water solution containing polyvinyl-alcohol by the quantity equivalent to 0.5 (weight %) of the fine powder is added to the fine powder, before it is kneaded to produce particles. A set of metal dies is employed with a press weight of 1,000 ($Kg/cm^2$) to mold a wet disk having the diameter of 4 (mm) and the thickness of 0.4 (mm) out of the foregoing particles. The wet disk is calcined in the air of 2,000 (°C.) for 2 hours to produce a replete sintered disk having the thickness of 0.3 through 0.35 (mm) and the diameter of 3.5 (mm). A sputtering process is employed to form platinum layers having the thickness of 1 (micrometer) on the center portion of each side of the oxygen ionic conductor for the purpose to produce the cathode 8 and the anode 9. Since the diameter of the cathode is an important parameter which determines the performance of an element, four different specimens having diameters different from one another are produced. Namely, specimens A, B, C and D respectively have diameters of 3.0 (mm), 2.5 (mm), 1.9 (mm) and 1.5 (mm). Anodes having the same dimension as the cathodes are produced on the corresponding location on the other surface of the oxygen ionic conductor. Lead wires 11 are platinum wires having a diameter of 0.3 (mm) and each of which is connected respectively to the cathode and anode by means of a thermal compression bonding process. The porous layer 10 is a layer of spinel having the thickness of 640 (micrometers) and which is produced to cover the cathode 8 by means of a plasma flame spraying process. The average grain size of the spinel is selected to be 47 (micrometers) in the diameter thereof. The determined porosity of the layer of the porous material is 9 (%).

Figure 9:
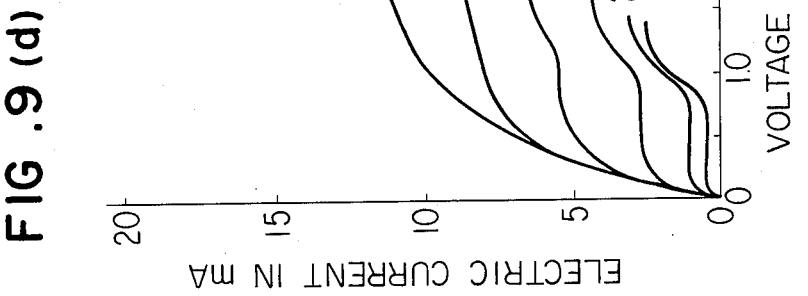
Figure 9:
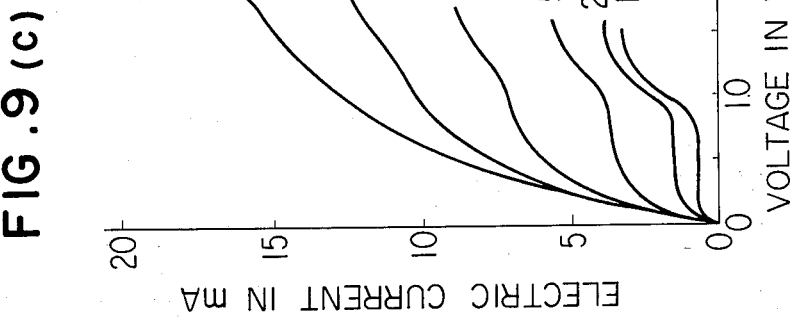
Figure 9:
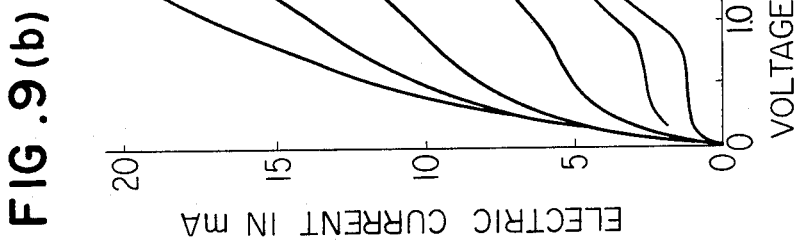
Figure 9:
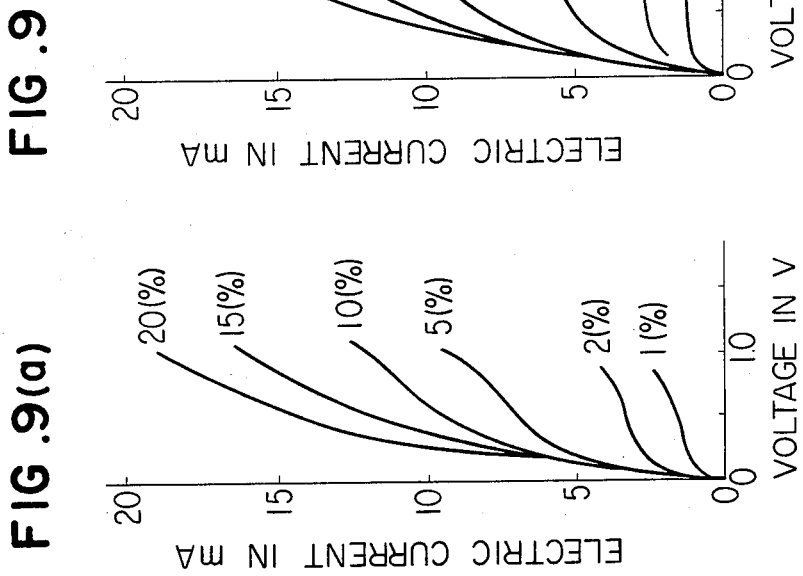
Figure 10:
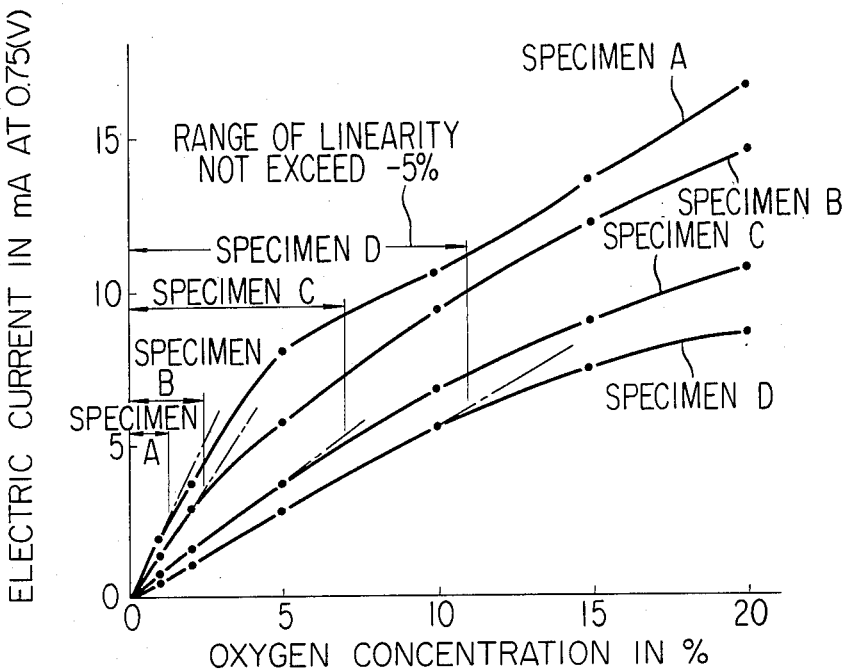
FIG. 10 is a graph showing the electric current vs. oxygen concentration relations of four different limiting electric current type oxygen concentration sensors of which the conceptual configuration is shown in FIG. 6 and each of which has a different diameter thereof.
Figure 11:
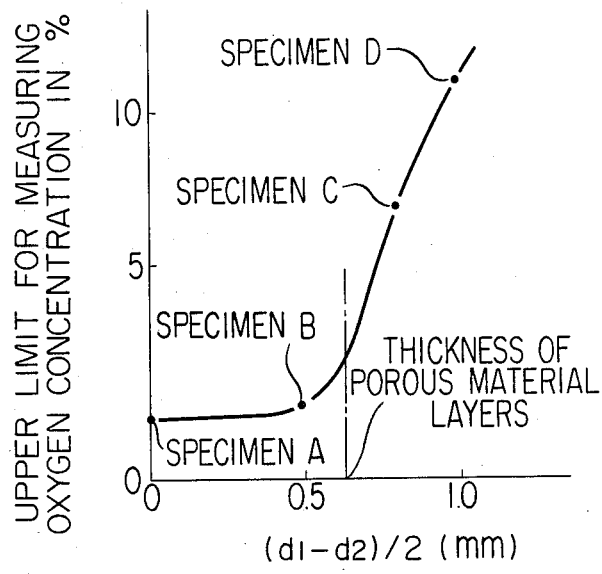
FIG. 11 is a graph showing a tendency in which an upper limit for measurement in terms of the oxygen concentration increases following an increase in the difference between the diameters of the cathode and the oxygen ionic conductor.

Measurement was carried out to determine the current vs. voltage characteristics of the sensor elements each of which has the amount of a diameter $d_2$ different for one another. The measurement was carried out in various types of atmospheres or quasi exhaust gases of a car produced by commingling water, carbon dioxide and oxygen with air to resultantly contain 3 (%) of $H_2O$, 10 (%) of $CO_2$ and 1 through 20 (%) of $O_2$. During the measurement carried out employing the foregoing various types of atmospheres, the temperature was maintained unchanged. FIGS. 9 (a), (b), (c) and (d) compares the results of measurement carried out for the four independent specimens A, B, C and D. FIG. 9 indicates that an increasingly less amount of the cathode diameter causes the corresponding less amount of incline of the current vs. voltage curve in the flat current voltage range. In other words, decrease of the area of a cathode in comparison with the overall area of an element is effective to improve the linearity of the current vs. voltage characteristics of the oxygen sensor. This effect is much clearer from FIG. 10 which compares the current vs. voltage relations for the four independent specimens A, B, C and D determined on the basis that the elements are applied a constant voltage of 0.75 (V). It is supposed that the oxygen concentration range wherein the linearity does not exceed −5 (%) for the output current vs. oxygen concentration relations is recognized as a range wherein measurement is allowed or the results of measurement is reliable (Hereinafter referred to as an upper limit for measurement.). Referring to FIG. 10, the upper limit for measurement in terms of the oxygen concentration is increased to 1.2 (%), 2.4 (%), 4.7 (%) and 11 (%) following the decrease of the diameter of the cathode respectively to 3.0 (mm), 2.5 (mm), 1.9 (mm) and 1.5 (mm). This is interpreted that an increasingly less area of the cathode in comparison with the areas of the oxygen ionic conductor and the layer of a porous material is effective to increase the area in which the layer of a porous material 10 directly contacts the oxygen ionic conductor 7 and that the corresponding increase in the length of the shortest path with which the gas reaches the cathode is effective to increase the upper limit for measurement in terms of the oxygen concentration. FIG. 11 shows a tendency of increase in the upper limit for measurement of the oxygen concentration which follows the increase in the length with which the layer of a porous material 10 contacts the oxygen ionic conductor $(d_1-d_2)/2$ (The amounts representing the upper limit for measurement of the oxygen concentration are acquired from FIG. 10 and the symbol $d_1$ represents the diameter of the oxygen ionic conductor). This indicates that if a length with which the layer of a porous material contacts the oxygen ionic conductor exceeds the thickness of the layer of a porous material 10, it is possible to considerably increase the oxygen concentration range in which the linearity is satisfactory. This requirement is satisfied in oxygen sensor elements shown in FIG. 7 or FIG. 8, because the layer of a porous material 10 and the oxygen ionic conductor 7 directly contact each other with a width equivalent to the thickness of the oxygen ionic conductor at the peripheral portion of the cathode. In the oxygen sensor element shown in FIG. 7, the layer of a porous material 10 connects with the other layer of a porous material 13 of which the purpose is to protect the anode. The essential requirements for the oxygen sensor element having this configuration shown in FIG. 7 are that the surface distance between the points a and b is equal to or larger than the thickness of the layer of a porous material 10 and the lateral thickness of the layer of a porous material 10 is so selected that the distance between the points b and c in FIG. 7 is equal to or larger than the thickness of the layer of a porous material 10 which covers the cathode.

Figure 8:
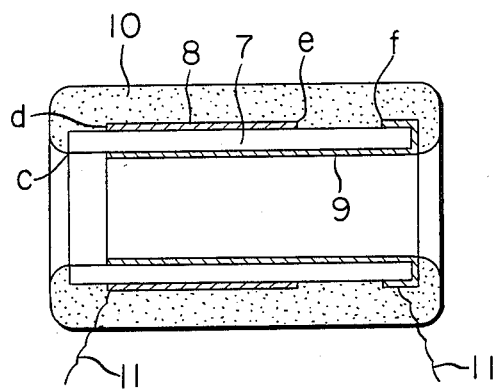
FIG. 8 is a side view of another modification of the limiting electric current type oxygen concentration sensor of which the conceptual configuration is shown in FIG. 6, FIGS. 9(a)–(d) are graphs showing the electric current vs. voltage relations employing the oxygen concentration as a parameter, of four different limiting electric current type oxygen concentration sensors of which the conceptual configuration is shown in FIG. 6 and each of which has a different diameter thereof.

FIG. 8 shows an oxygen sensor element provided with an oxygen ionic conductor having a cylindrical shape. Referring to the figure, an oxygen ionic conductor 7 having a cylindrical shape is provided with a cathode 8 arranged on the external surface thereof and with an anode 9 arranged on the internal surface thereof. One of the lead wires 11 is connected with the cathode 8 and the other of the lead wires 11 is connected with an end of the anode 9 which is extended to the external surface of the oxygen ionic conductor 7 along one end of the oxygen ionic conductor 7. A layer of a porous material 10 uniformly covers the entire external surface of the oxygen ionic conductor 7 having the cathode 8 and one end of the anode 9 arranged thereon. Each of the distances cd and ef which are distances along the surface of the oxygen ionic conductor is selected to exceed the thickness of the layer of a porous material 10. The distance de is selected to exceed the thickness of the layer of a porous material 10.

The second item of improvement applicable to the oxygen concentration sensor shown in FIG. 2 will be described below.

Figure 7:
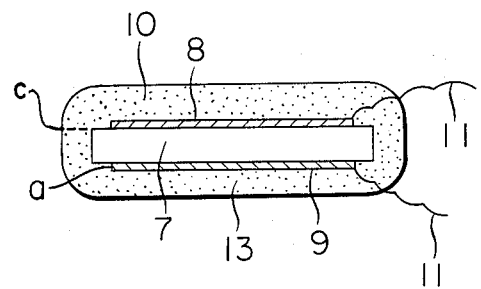
FIG. 7 is a side view of one modification of the limiting electric current type oxygen concentration sensor of which the conceptual configuration is shown in FIG. 6.

The foregoing first item of improvement described with reference to FIGS. 6, 7, and 8 is effective to improve the linearity of the oxygen concentration detection characteristics, the improvement being based on the uniform current density along the cathode realized by decrease of the cathode area in comparison with the corresponding area of the layer of a porous material. However, the foregoing improvement is not effective to entirely block the lateral flow of electric current. Therefore, the degree of decrease in the element current is less than the corresponding degree of the decrease in the cathode area. Accordingly, the current density is increased for the cathode. This increase in current is assumed to be a parameter to cause a problem for the stable performance for detection of the oxygen concentration, provided it is employed for a long time under severe conditions, for example in an exhaust gas of a car which is high in temperature and which contains a sizable amount of erosive gases.

Figure 12:
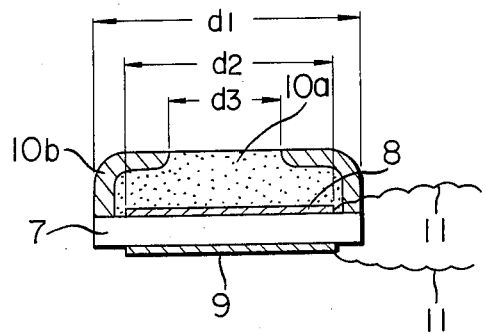
FIG. 12 is a side view of another improved model of a limiting electric current type oxygen concentration sensor.
Figure 14:
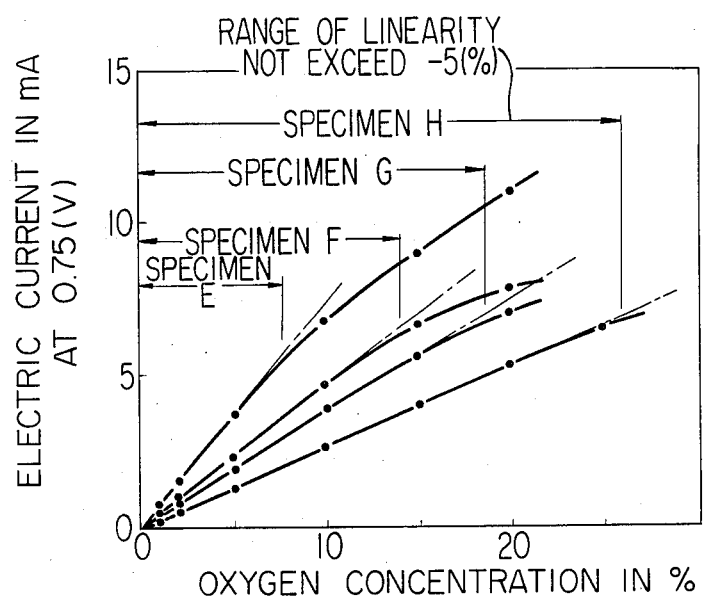
FIG. 14 is a graph showing the electric current vs. oxygen concentration relations of four different limiting electric current type oxygen concentration sensors of which the conceptual configuration is shown in FIG. 12 and each of which has a different diameter thereof.
Figure 15:
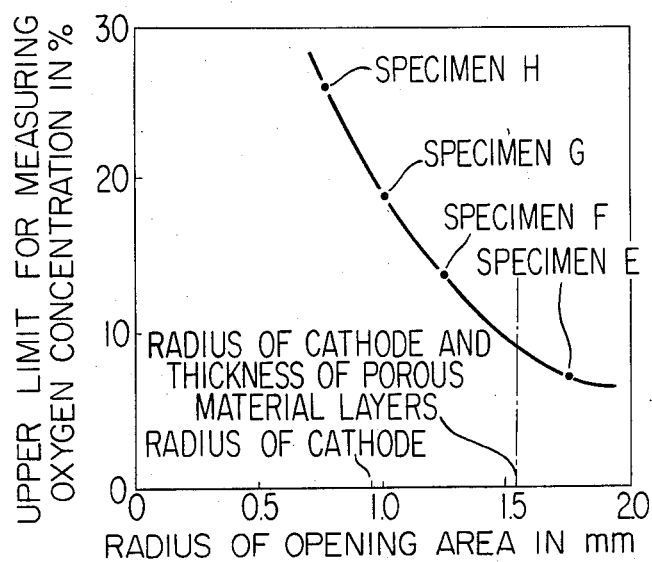
FIG. 15 is a graph showing a tendency in which an upper limit for measurement in terms of the oxygen concentration increases following a decrease in the diameter of the opening portion of the porous material layer arranged to cover the cathode of a sensor.

The foregoing drawback is removed in a limiting electric current type oxygen concentration sensor in accordance with the second embodiment of the present invention which will be described below. This oxygen concentration sensor is provided wih a porous material layer of which the porosity is decreased in the center portion thereof rather than in the peripheral portion thereof for the purpose to decrease the flow of oxygen in the direction parallel to the surface of a cathode from the side portion of the sensor. Further, the area by which the portion of the porous material layer having a larger amount of porosity is exposed to a gas of which the oxygen concentration is measured (Hereinafter referred to as an opening area.), is selected to be less than a certain amount. FIG. 12 shows the conceptual configuration of this oxygen concentration sensor. Referring to the figure, an oxygen ionic conductor 7 is provided with a cathode 8 and an anode 9 which are arranged on each surface thereof. The peripheral portion of a porous material layer 10a is impregnated with a filler to be converted to a portion 10b having a quite marginal amount of porosity. Lead wires 11 are drawn from the cathode 8 and the anode 9. Each of the members 7, 8, 9, 10a, and 11 is produced of the material similar to the material for the corresponding member of the foregoing first embodiment by means of the process similar to that for the foregoing first embodiment, and they are arranged in a concentric arrangement. The important parameters for this oxygen concentration sensor shown in FIG. 12 are the diameter $d_1$ of the oxygen ionic conductor 7, the diameter $d_2$ of the cathode 8, and the diameter $d_3$ of the opening area or the area of the portion of the porous material layer having a larger amount of porosity. One example of this oxygen concentration sensor has an oxygen ionic conductor having the diameter of 3.5 (mm) and the thickness of 0.3 (mm) through 0.35 (mm), a cathode and an anode each of which has the diameter of 1.9 (mm) and the thickness of 1 (micrometer). The thickness of the porous material layers 10a and 10b is 600 (micrometers). The peripheral portion of the porous material layer is, after it is produced employing the process similar to that which was employed for the first embodiment, sprayed with alumina based thermal resistant adhesive (having the brand name "Sumiseram" and produced and marketed by Sumitomo Chemical Industry Co. of Japan), while the opening portion 10a is covered by a water repelling soft material e.g. a silicon rubber, before the adhesive is impregnated uniformly in the hatched portion 10b. The thickness of the impregnated portion is determined by the viscosity of the coating agent and the length of period in which the coating process is carried out. Three specimens were produced for the purpose to determine the effect of the peripheral portion of a porous material layer in which the porosity is decreased. Each of the three specimens F, G and H has a lower porosity portion having the thickness of approximately 0.1 (mm) and an opening portion having the diameter respectively of 2.5 (mm), 1.9 (mm) and 1.5 (mm). FIG. 13(a), (b), (c) and (d) compares the electric current vs. voltage characteristics determined for the specimens F, G and H and for a specimen E of which the porous material layer is not impregnated with a coating material and of which the diameter of the opening portion is equivalent to 3.5 (mm). The figures show that the limiting current characteristics is improved following decrease is the area of opening area $d_3$. In other words, albeit the specimen E is accompanied by a large amount of incline of the current vs. voltage characteristics curve in the flat current voltage range particularly in the high oxygen concentration range and exhibits an unsatisfactory limiting current characteristics, specimens, F, G and H show increasingly better limiting current characteristics, following decrease in the area of the opening area $d_3$ particularly in the high oxygen concentration range. It is noted that the element current density or the cathode current density is decreased for the same oxygen concentration, following decrease in the area of the opening area $d_3$. FIG. 14 shows the sensor output vs. oxygen concentration characteristics of the sensors shown in FIG. 12 determined under the condition where the sensors are applied a voltage of 0.75 (V). Referring to FIG. 14, the oxygen concentration at which the linearity of the oxygen concentration detection characteristics decreases until $-5$ (%), is determined. FIG. 15 shows a tendency in which the upper limit for measurement in terms of the oxygen concentration increases following decrease in the diameter of the opening portion. FIGS. 14 and 15 show that the effect for improvement of the oxygen concentration detection characteristics is considerably increased, under the condition where the diameter of the opening portion is less than the length which is equivalent to the diameter of a cathode plus the thickness of a porous material layer. Further, FIG. 15 shows that the upper limit for measurement in terms of the oxygen concentration is improved to 20 (%) or more for the oxygen concentration sensors G and H of which the diameters of the opening portions are decreased to the length equivalent to the diameter of the cathode, allowing an extremely wide range of the oxygen concentration in which measurement is possible, for such sensors. It is determined that the cathode current density of the specimen H is decreased to $\frac{1}{3}$ or less in comparison with the specimen D which is one specimen representing the first embodiment of this invention, under the same grade of the oxygen concentration. The foregoing description has clarified that either of the foregoing embodiments satisfies the requirement that the oxygen concentration detection characteristics should be maintained for a long time.

Figure 16:
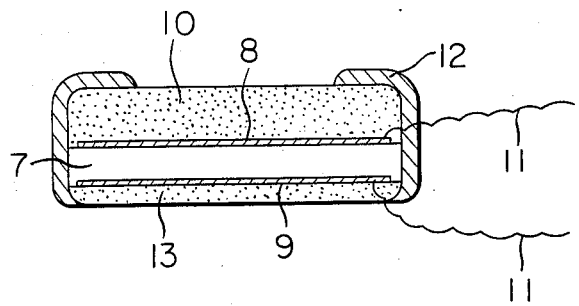
FIG. 16 is a side view of a limiting electric current type oxygen concentration sensor in accordance with one modification of the limiting electric current type oxygen concentration sensor shown in FIG. 12.
Figure 17:
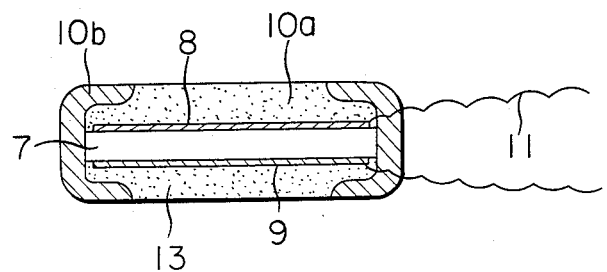
FIG. 17 is a side view of a limiting electric current type oxygen concentration sensor in accordance with another modification of the limiting electric current type oxygen concentration sensor shown in FIG. 12.
Figure 18:
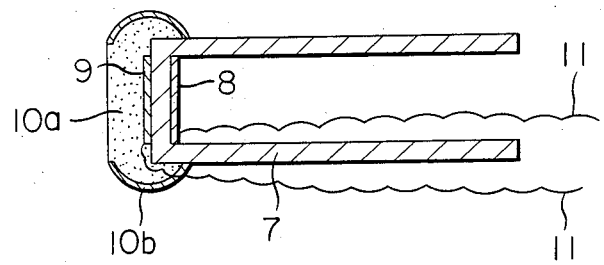
FIG. 18 is a side view of a limiting electric current type oxygen concentration sensor in accordance with the third modification of the limiting electric current type oxygen concentration sensor shown in FIG. 12.

A sintered solid solution having a composition of $(ZrO_2)_{0.92}(Y_2O_3)_{0.08}$ is employed as the oxygen ionic conductor in either of the first and second embodiments of this invention. In addition to this sintered solid solution, some other sintered solutions composed of one or more substances selected from the group of $HfO_2$, $ThO_2$, $Bi_2O_3$ et al. and one or more stabilizers selected from the group of CaO, MgO, $Sc_2O_3$ et al. can be employed as an oxygen ionic conductor. In addition to platinum, refractory conductive metals such as Rh, Ir, Pd, Ag et al. can be employed as a material for the cathode or the anode. Some of these metals or some alloys produced of these metals can be placed on an oxygen ionic conductor by means of sputtering, evaporation, metal plating, paste-baking et al. Thermo-resistant inorganic materials e.g. materials based on silica, alumina, spinel, magnesia, zircon et al. can be employed as a porous material. The porous material layer has a function to regulate the diffusion rate of oxygen therein. Even in the case where the diffusion rate is selected to a certain amount, selection is allowed for porosity, the diameter range of perforations and the thickness of the porous layer. Therefore, the porous material layer can be produced by depositing a layer having the thickness of e.g. 0.1 through 10 (micrometer) by means of sputtering, evaporation et al., before it is made porous by means of an etching process et al. In the case where a porous material layer of a material based on spinel is produced by means of the plasma sputtering process as is for the first or second embodiment, a source material having the average grain size of 2 through 70 (micrometers) can be utilized for the process. In this case, the thickness range of 100 through 1,000 (micrometers) can be realistic, because exfoliation, cracking et al. scarcely happen for the porous material layer. A porous material layer can be a protective layer for an anode. In the second embodiment, the diameter of the opening portion was produced by means of application of a thermo-resistant adhesive to the portion. This means can be employed for production of oxygen concentration sensors having the configuration shown in FIG. 16, 17 or 18. In FIG. 16, the indicated as 12 is a layer having a less amount of porosity, the layer being placed surrounding a porous layer 10 and an oxygen ionic conductor 7. The function of a porous layer 13 is to protect an anode 9. It is possible, as shown in FIG. 17, to produce the upper and lower surfaces symmetrical each other. The oxygen ionic conductor 7 shown in FIG. 18 is a tube whose one end is closed and wherein a reference gas e.g. air is introduced.

The foregoing description has clarified the configuration of an oxygen concentration sensor based on the limiting current characteristics acquired by covering an oxygen ionic conductor layer with a porous material layer thereby the oxygen concentration detection range is improved and the simplified configuration considerably decreases the production cost. Further, if this oxygen concentration sensor is applied with a heater which is arranged in the neighborhood of this sensor or is buried in this sensor, the sensor can be employed for detection of the oxygen concentration also for a wide temperature range which is inevitable for the detection of an exhaust gas of a car.

(d) Limiting electric current type oxygen concentration sensor provided with a means for detection of the internal resistance of a sensor A limiting electric current type oxygen concentration sensor in accordance with this embodiment of this invention is provided with a detector for the internal resistance thereof which is responsive to the temperature thereof for the purpose to control the operation of the sensor, following the determined internal resistance thereof, for the ultimate purpose to prevent a measurement error caused by deviation of the limiting current characteristics of the sensor and of the internal resistance of the sensor caused by deviation of the temperature thereof, from occurring.

The foregoing measurement of the internal resistance can be carried out for a tow-terminal type oxygen concentration sensor which has one cathode and one anode and which was presented in the description for the foregoing items (a), (b) and (c). However, a three or four-terminal type oxygen concentration sensor which has electrodes for measurement of the internal resistance of the sensor is accompanied by a simpler circuit for measurement of the internal resistance.

Figure 19:
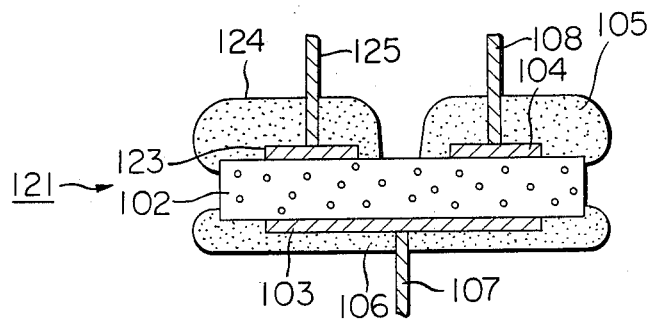
FIG. 19 is a side view of a limiting electric current type oxygen concentration sensor provided with a component for measuring the internal resistance in accordance with one embodiment of this invention.

FIG. 19 shows one example of a three-terminal type oxygen concentration sensor provided with a means for measurement of the internal resistance thereof. The limiting current type oxygen concentration sensor 121 is provided with the basic component which is an assembly consisting of an oxygen ionic conductor provided with a cathode placed on one surface of the oxygen ionic conductor and provided with an anode placed on the other sirface of the oxygen ionic conductor or which is an assembly (limiting current detection side) in which the cathode is covered by a member which limits the gas diffusion to the cathode layer and an additional component (internal resistance detection side) which is an assembly consisting of an oxygen ionic conductor 102 provided with an electrode 123 placed on one surface of the oxygen ionic conductor which detects the internal resistance of the sensor and provided with an electrode 103 placed on the other surface of the oxygen ionic conductor to face with the foregoing electrode 123. In the shown example, the electrode 103 functions both for the limiting current detection side and for the internal resistance detection side. The construction in which the electrode 103 is employed for the both purposes has an advantage in which the number of terminals is decreased to three for the limiting current type oxygen concentration sensor. The chemical compositions of the electrodes and the porous material layers are identical to those for the basic component. The purpose of a porous material layer 124 arranged on the electrode 123 is to simply protect the electrode 123, as is in the case of the porous material layer 106. Therefore, the same process can be employed for the porous material layer 124 as for the porous material layer 106.

Since the internal resistance detection side functions independently from the limiting current detection side, the internal resistance detection side can be flowed with a direct current for the purpose to detect the internal resistance. The porosity or the grade of gas diffusion of the porous material layer 106 is preferable to be selected to be same as that of the porous material layer 105. This is because the porous material layer 106 is to drain oxygen, albeit the porous material layer 105 is to regulate the oxygen diffusion rate.

If a larger grade of gas diffusion is selected for the porous material layer 124 than for the porous material layer 105, or if a less amount of electric current is selected for the porous material layer than the amount of current which causes the porous material layer 124 to regulate the speed of oxygen under the condition where the grade of gas diffusion is same for the both layers, the internal resistance detection side functions exclusively in the resistance domination range, even if the current density of the internal resistance detection side is selected to be identical to that of the limiting current detection side.

In the case where the quality of the both electrodes 123 and 104 and the quality of the both porous material layer 124 and 105 are same each other and in the case where the amount of the limiting current flowing in the unit area of the electrode is same as each other, if a same current density is flowed both to the limiting current detection side and to the internal resistance detection side, no voltage difference ΔV is generated between the electrode 123 and the electrode 104 or the point a and the point b. As a result, the internal resistance detection side also functions exclusively in an excess voltage domination range. Therefore, it is necessary to select the current density flowing in the electrode 123 of the internal resistance detection side to be less than the current density of the limiting current detection side. (From the practical viewpoint, less than 0.7 through 0.9 times as high as the limiting current detection side.)

Figure 20:
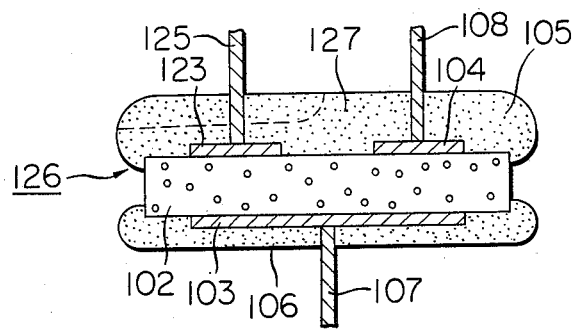
FIG. 20 is a side view of a limiting electric current type oxygen concentration sensor provided with a component for measuring the internal resistance in accordance with another embodiment of this invention.

If the grade of the gas diffusion is made larger if and the current density of the limiting current of the internal resistance detection side is made larger than the other by means of construction of the internal resistance detection side produced of a thin porous material layer 127 as shown by a broken line in FIG. 20, an excess voltage caused by the limiting current becomes non-influential at the electrode of the 123 side. It is clear that the internal resistance detection side can be constructed not to exhibit the limiting current characteristics at all. This can be realized by employing an electron ionic conductor or an ionic conductor for ions and electrons for producing the member which is put between the electrodes 123 and 104.

It is possible to prohibit the influence of an excess voltage from taking place, if the current density of the electrode of the internal resistance detection side is made less than the current density of the electrodes of the limiting current detection side (0.01 through 0.7 times) by making the area of the electrode 123 larger than the area of the electrode 104. In this case, the sensor is not necessary to have a special shape which is shown by a broken line in FIG. 20 for the purpose to make the amount of the limiting current large.

The electrode 123 of the internal resistance detection side and the electrode 104 of the limiting current detection side can be arranged in a concentric position rather than in a parallel position shown in FIG. 19 and FIG. 20.

The direction of the current is not limited to the direction shown in FIG. 19 or FIG. 20. In other words, the direction of the current for measuring the internal resistance is allowed to be contrary to the direction of the current for measuring the limiting current, as shown in FIG. 21.

Figure 21:
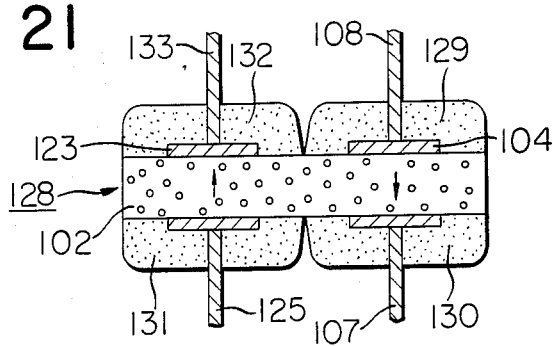
FIG. 21 is a side view of a limiting electric current type oxygen concentration sensor provided with a component for measuring the internal resistance in accordance with the third embodiment of this invention.

Referring to FIG. 21, this model has an advantage in which the thickness of the porous material layers are allowed to be selected independently from each other. The reason why the configuration shown in FIG. 21 is preferred is that it is necessary to limit the lateral flow of oxygen ions in the ionic conductor 102 in view of the existence of cross current in the direction from the porous material layer 129 to the porous material layer 130 and in the direction from the porous material layer 131 to the porous material layer 132, and that it is necessary to limit the flow of the oxygen gas from 132 to 129. As a result, the internal resistance detection side and the limiting current detection side are separated from each other by a distance equivalent to the thickness of the oxygen ionic conductor, for the purpose to satisfy these requirements.

In this case, it is possible to make the amount of the limiting current of the internal resistance detection side larger than the amount of the limiting current detection side by making the thickness of the porous material layer 131 thinner than the thickness of 131. Therefore, it is made possible to correctly measure the internal resistance without being influenced by an excess voltage even under a condition where the current density is same for the both sides. In addition, since the porous material layers 129 and 131 are not arranged on the same surface, the porous material layers can easily be produced independently from each other.

DEPENDENCE OF LIMITING CURRENT TYPE OXYGEN CONCENTRATION SENSOR UPON TEMPERATURE

Figure 22:
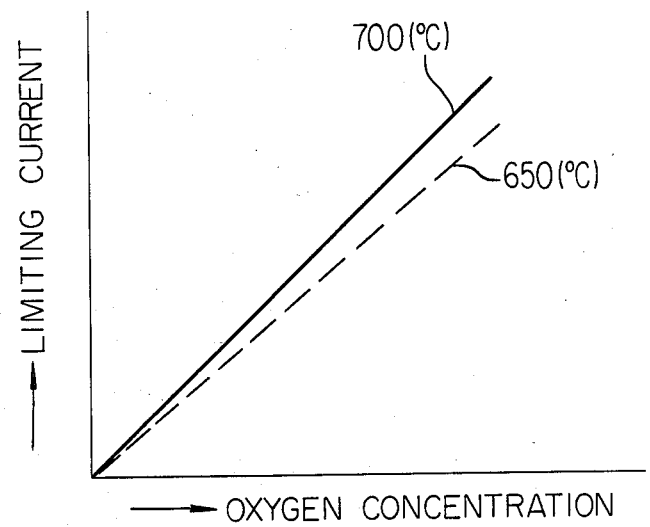
FIG. 22 is a graph showing the limiting current vs. oxygen concentration relations of a limiting electric current type oxygen concentration sensor under two different temperatures as parameters.
Figure 23:
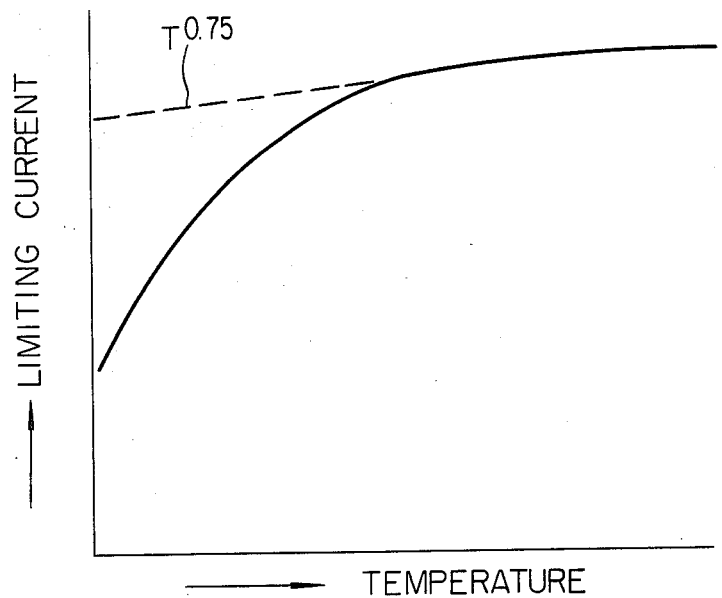
FIG. 23 is a graph showing the limiting current vs. temperature relations of a limiting electric current type oxygen concentration sensor for a certain oxygen concentration.

FIGS. 22 and 23 show the dependence of a limiting current upon a temperature under an arbitrary amount of oxygen concentration. This nature predominantly depends on the corresponding nature of the diffusion rate of a gas.

The characteristics of a limiting current type oxygen concentration sensor provided with a porous layer which functions to regulate the flow of the oxygen gas is represented by the following formula.

$$Il = \frac{4FS\,D_{O2eff}P}{RTl} \ln\left(\frac{1}{1-\frac{P_{O2}}{P}}\right) \quad (5)$$

wherein,
Il represents a limiting current,
F represents Faraday constant,
S represents an area in which the oxygen flow is regulated,
$D_{O2eff}$ represents an effective diffusion rate,
$R_{O2}$ represents a partial pressure of oxygen,
P represents a total pressure,
R represents gas constant,
T represents an absolute temperature,
l represents the thickness of a porous material layer,
ln represents a natural logarithm.

If the oxygen partial pressure ratio $P_{O2}/P$ is much less than 1, the formula 5 can be approximately simplified to $$Il \approx \frac{4FS\,D_{O2eff}P}{RTl} \cdot \frac{P_{O2}}{P} \quad (6)$$

From the experience, $$D_{O2eff}(T) = D_{O2eff}(To) \cdot (T/To)^{m+1} \quad (7)$$

wherein,
To represents a reference temperature,
$D_{O2eff}(T)$ represents the effective diffusion constant at the temperature T,
$D_{O2eff}(To)$ represents the effective diffusion constant at the temperature To.

Also from the experience, it is known that the index (m+1) in this formula is 1.75.

Accordingly, the dependence of the output current upon the temperature defined as a ratio of the output current Il(T) under a temperature T and the output current Il(To) under a temperature To under a certain amount of the partial pressure of oxygen is represented by $$Il(T)/Il(To) = (T/To)^m \quad (8)$$

If the limiting current depends only upon the variation of the diffusion rate of a gas caused by a variation of temperature, the variation of the output current of a sensor is limited to a marginal extent which can be represented by a quasi-straight ($T^{0.75}$) broken line in FIG. 23. In reality, however, since the internal resistance extremely increases in the low temperature range, a large amount of voltage-drop is caused in a sensor. As a result, the limiting current sharply drops in the low temperature range as shown by a full line in FIG. 23.

Figure 24:
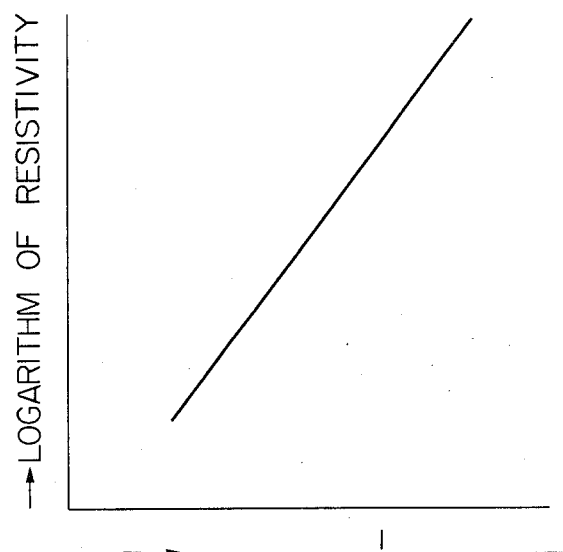
FIG. 24 is a graph showing the dependence of the internal resistance upon the temperature of a limiting electric current type oxygen concentration sensor.
Figure 25:
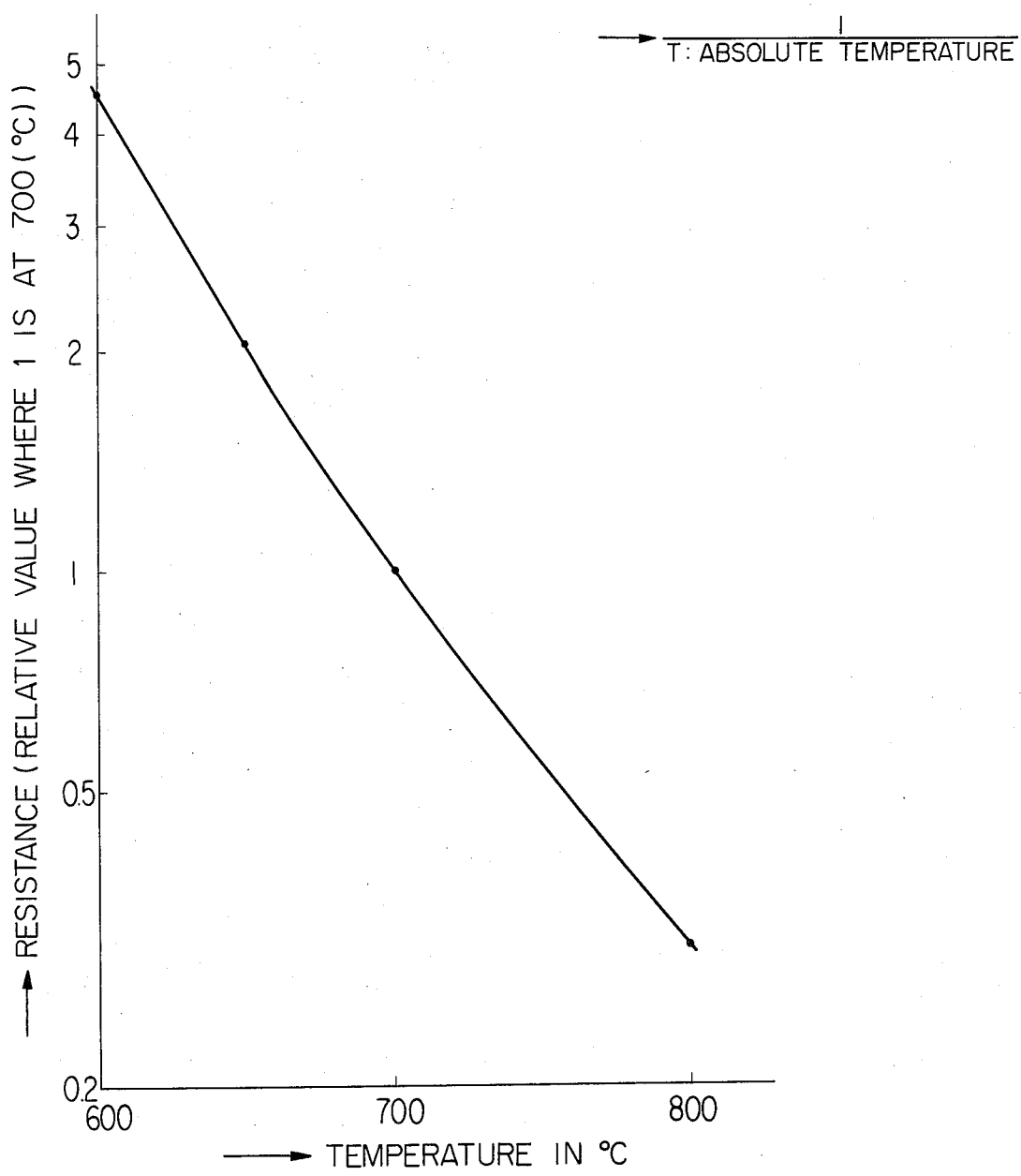
FIG. 25 is a graph showing the dependence of the internal resistance upon the temperature of a limiting electric current type oxygen concentration sensor.

FIGS. 24 and 25 show the relations of the temperature vs. the resistivity ρ of an oxygen ionic conductor employed for a limiting current type oxygen concentration sensor. The characteristics is approximately represented by the following formula. FIG. 25 employs a semilogarithmic scale.

$$\rho = c_1 e^{(E/KT)} \quad (9)$$

wherein,
$c_1$ represents a coefficient,
e represents a base of the natural logarithm,
E represents an activation energy,
K represents Boltzmann factor,
T represents an absolute temperature.

The coefficient $c_1$ and the activation energy E are determined by the composition of a material, the sintering condition, impurities contained et al. The oxygen ionic conductors having the foregoing composition give a small amount of $c_1$, resultantly causing a good performance. Any oxygen ionic conductor having any composition has a nature to increase the resistivity thereof following a decrease of temperature as shown in FIG. 25. This is because the amount of the activation energy is as high as 0.5 through 1.4 (eV). The amount of a resistance existing along the surface of an ionic conductor and an electrode varies depending on the surface treatment conditions, the material for the electrode, et al. It is possible to decrease the surface resistance to a practically allowable amount, if a composite material having the foregoing composition is employed.

Since the internal resistance of a limiting current type oxygen concentration sensor varies depending on the temperature thereof as described above, the temperature of the sensor can be detected by means of measurement of the internal resistance thereof.

Substituting the conditions that $\rho = \rho_o$ provided $T = To$ into the formula 9, $$c_1 = \frac{\rho_o}{e^{(E/KTo)}} \quad (10)$$

$$\rho = \rho_o e^{\frac{E}{K}\left(\frac{1}{T} - \frac{1}{To}\right)} \quad (11)$$

$$T = \frac{1}{\frac{K}{E}\log_e\left(\frac{\rho}{\rho_o}\right) + \frac{1}{To}} \quad (12)$$

wherein, $\log_e$ represents a natural logarithm.

Since it is possible to assume that the resistivity of a sensor is proportional to the internal resistance thereof, the formula 12 which relates to a resistivity can be converted to $$T = \frac{1}{\frac{K}{E}\log_e\left(\frac{R}{Ro}\right) + \frac{1}{To}} \quad (13)$$

wherein,
R represents an internal resistance,
Ro represents an internal resistance at the temperature of To.

Since the relations between E as well as To and Ro are determined for each sensor, it is possible to acquire the absolute temperature T, if the internal resistance R is provided.

LIMITING ELECTRIC CURRENT TYPE OXYGEN CONCENTRATION DETECTOR IN ACCORDANCE WITH THE FIRST EMBODIMENT OF THIS INVENTION

As is clear from the formula 8 or FIG. 22 or 23, a variation of a temperature T causes a corresponding variation of the limiting current Il (T), resultantly causing an error. The first embodiment of this invention is provided with a means for controlling the sensor temperature for the purpose to prevent a temperature variation from occurring for the ultimate purpose to remove the foregoing drawback.

As described above, an internal combustion engine varies the temperature of the exhaust gas thereof depending on the operating conditions. This means that temperature detection and temperature control are required for the purpose to employ an oxygen concentration sensor at a constant temperature.

A thermosensitive unit e.g. a thermocouple, a thermo-sensitive resistor et al. is provided in the neighborhood of a limiting current type oxygen concentration sensor for the purpose to detect the temperature of a gas of which the oxygen concentration is measured. However, this usual method is involved with a drawback in which the limiting current type oxygen concentration detector provided with a thermosensitive unit is complicated in the overall structure, large in the overall dimension and expensive in the production cost. Further, it is not necessarily easy to keep the temperature of the thermosensitive unit same to that of the limiting current type oxygen concentration sensor.

The first embodiment of this invention which removes the foregoing drawbacks is based on an idea that the temperature of a limiting current type oxygen concentration sensor is maintained at a predetermined amount by means of temperature control applied thereto following the temperature of the sensor determined by detection of the internal resistance of the sensor which has a nature to vary following the temperature thereof.

Figure 26:
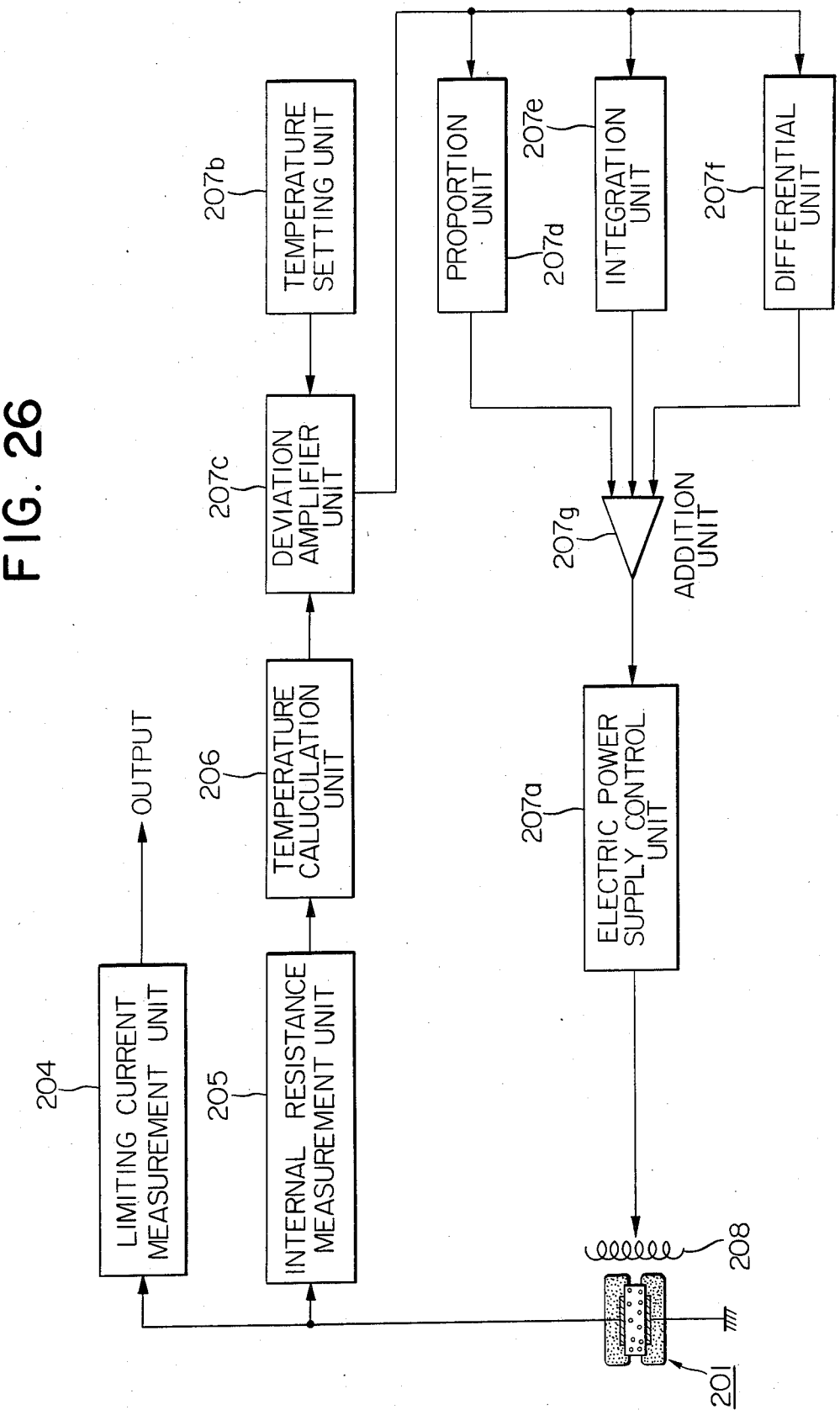
FIG. 26 is a block diagram showing the fundamental construction of a limiting electric current type oxygen concentration detector in accordance with the first embodiment of this invention.

FIG. 26 is a block diagram showing the fundamental construction of a limiting electric current type oxygen concentration sensor in accordance with the first embodiment of this invention.

Referring to FIG. 26, this limiting current oxygen concentration sensor is provided with a limiting current oxygen concentration sensor 201, a limiting current measurement unit 204 for detecting a limiting current which flows responsive to a voltage in the excess voltage domination range which is applied to the sensor, an internal resistance measurement unit 205 for measuring the internal resistance of the foregoing sensor employing a voltage in the resistance domination erectric current in the resistance domination range flowing in the foregoing sensor 201 or an range applied to the foregoing sensor 201, a temperature calculation unit 206 for calculating the temperature from the measured internal resistance, an electric power supply control unit 207a, a temperature setting unit 207b, a deviation amplifier unit 207c, a proportion unit 207d, a multiplication unit 207e, a differential unit 207f, an addition unit 207g and a heater unit 208. It is possible to eliminate the temperature calculation unit 206 to apply the output of the internal resistance measurement unit 206 directly to the deviation amplifier unit 207c. In addition, it is possible to eliminate the differential unit 207f to simplify the construction. Various types of the measurement equipment can be employed as the internal resistance measurement unit 205. It is possible to arrange a part which is employed to measure the internal resistance in the oxygen ionic conductor, to measure the internal resistance employing the resistance domination range, or to measure the internal resistance employing alternative current based on the feature of an equivalent circuit. This limiting current type oxygen concentration sensor is allowed to employ any type of the methods for measurement of an internal resistance.

The temperature calculation unit 206 is required to calculate the temperature employing the foregoing formula 13 of an approximation thereof.

Either hardware or software can be employed to calculate the temperature employing the formula 13. A means for calculation of the logarithm calculation term $\log_e (R/Ro)$ can be readily constructed employing the logarithm convertion module 4366 or 4367 produced and marketed by Teledyne Fillbrick or the like.

If the simplicity is preferred to the accuracy, it is possible to substitute the logarithm calculation with a simple approximation.

Figure 27:
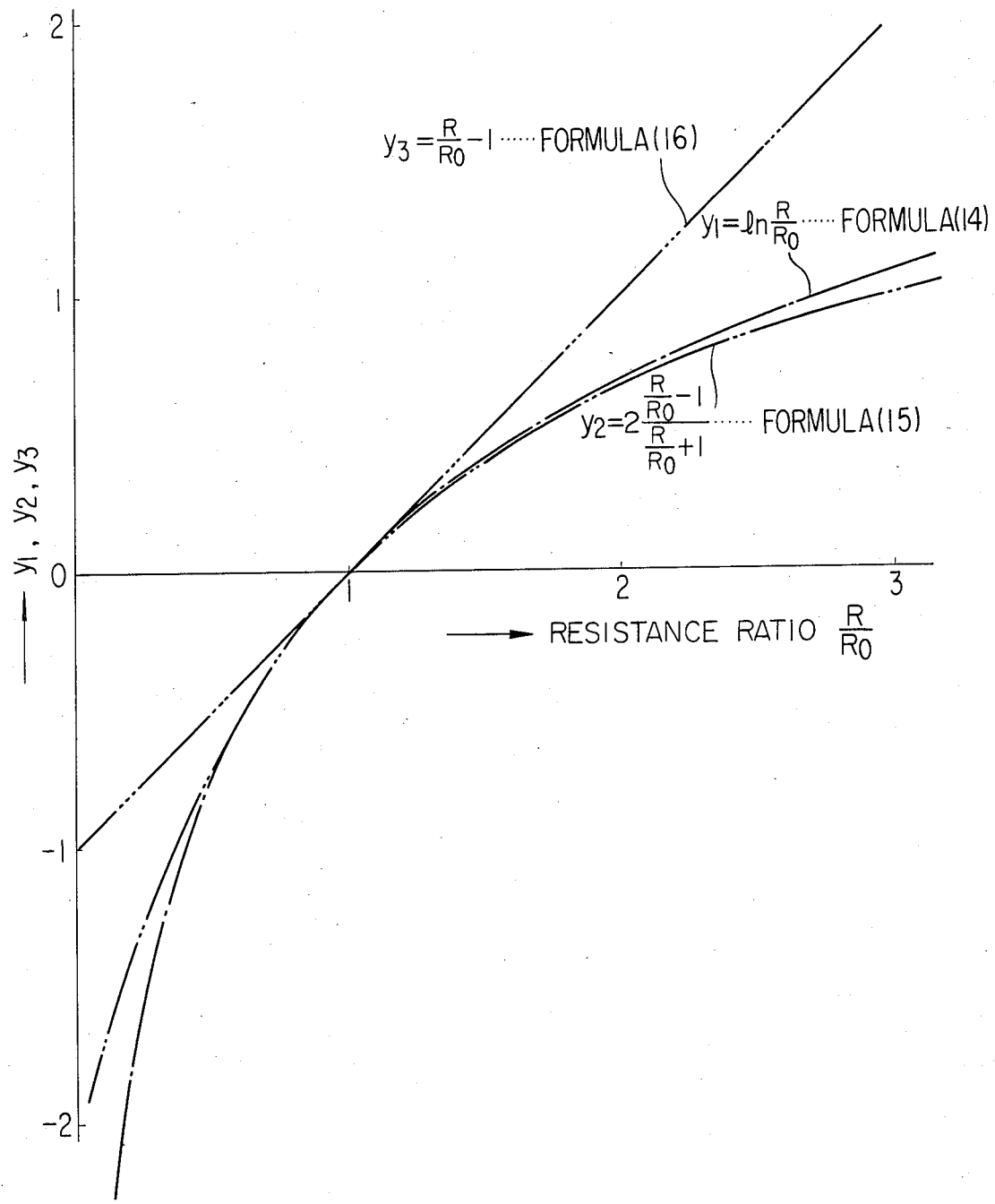
FIG. 27 is a graph showing the accuracy of and the applicable range of a simple approximation.

FIG. 27 shows the results of a study carried out to determine the applicable range in terms of R/Ro and the accuracy for a substitution of a function $$y_1 = \log_e (R/Ro) \tag{14}$$

with a function $$y_2 = 2\left(\frac{R/Ro - 1}{R/Ro + 1}\right) \tag{15}$$

The figure shows that the results of the both functions meet each other for the range of 0.3 <R/Ro <3 to a satisfactory extent.

The same figure shows the results of the case in which a simpler approximation $$y_3 = (R/Ro) - 1 \tag{16}$$

is employed. Since the necessary calculation's of this approximation are limited to addition and subtraction, this considerably simplifies the calculation. Incidentally, however, this limits the applicable range in terms of R/Ro to 0.6 <R/Ro<1.4.

In accordance with the approximation shown in the formula 15, $$T = \frac{1}{2\frac{K}{E}\left(\frac{\frac{R}{Ro} - 1}{\frac{R}{Ro} + 1}\right) + \frac{1}{To}} \tag{17}$$

On the other hand, in accordance with the approximation shown in the formula 16, $$T = \frac{1}{\frac{K}{E}\left(\frac{R}{Ro} - 1\right) + \frac{1}{To}} \tag{18}$$

Figure 28:
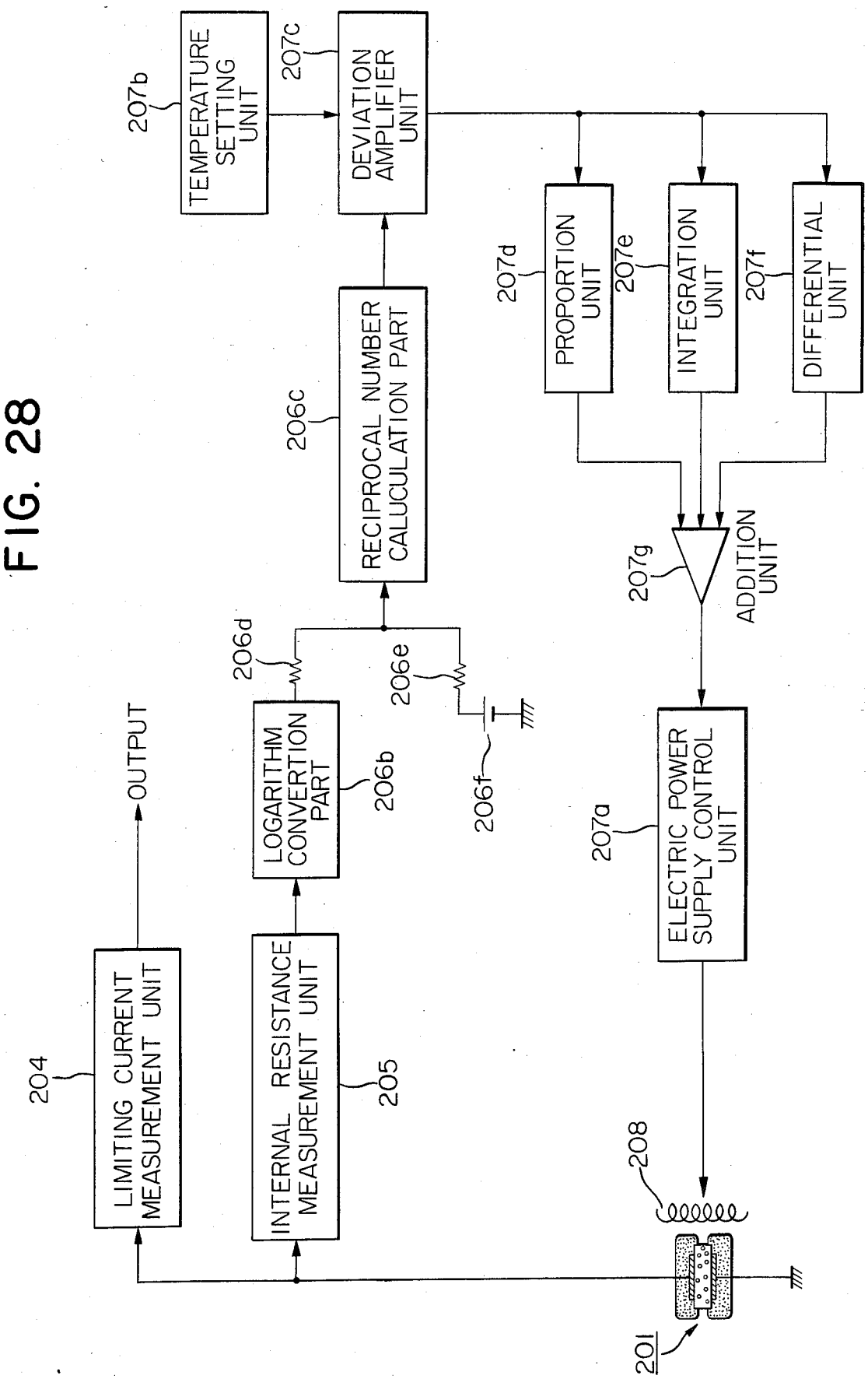
FIG. 28 is a block diagram of a limiting electric current type oxygen concentration detector in accordance with one modification of the first embodiment of this invention wherein the temperature calculation is carried out employing the formula 13.

FIG. 28 shows a block diagram of a limiting current type oxygen concentration detector wherein the temperature calculation is carried out employing the formula 13. This figure shows one example of the temperature calculation unit 206 shown in FIG. 26, which comprises a logarithm convertion part 206b, resistance type voltage deviders 206d and 206e, a fixed voltage power supply 206f and an inverse number calculation part 206c. The foregoing equipment can be employed as the logarithm convertion part 206b. It is possible to eliminate the inverse number calculation part 206c and to set the inverse number of the temperature.

Figure 29:
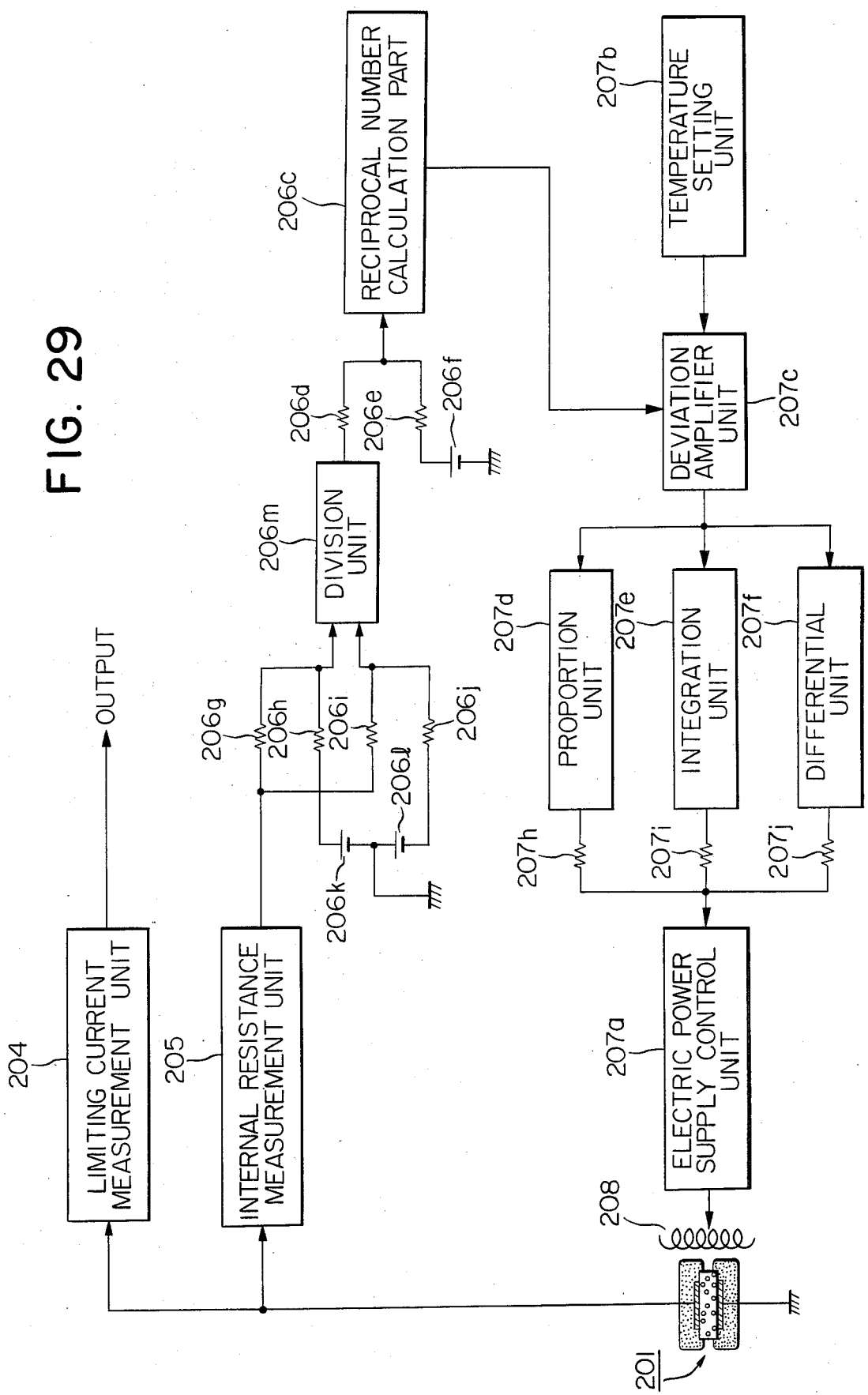
FIG. 29 is a block diagram of a limiting electric current type oxygen concentration detector in accordance with another modification of the first embodiment of this invention wherein a logarithm convertion part is eliminated.

An oxygen concentration detector shown in FIG. 29 is different from that shown in FIG. 28 in the following two points. The first is that it employs the approximation shown in the formula 17 and that it is provided with fixed voltage power supplies 206k and 206l, resistance type voltage dividers 206g and 206h and resistance type voltage dividers 206i and 206j, and a division unit, rather than a logarithm calculation unit. The second is that the addition unit 207g shown in FIG. 28 is replaced by resistances 207h, 207i and 207j.

An oxygen concentration detector shown in FIG. 30 which employs the approximation shown in the formula 18 is not provided with the elements including 206g, 206h, 206i, 206j, 206k, 206l, and 206m, resultantly causing the construction of the detector extremely simpler.

Figure 31:
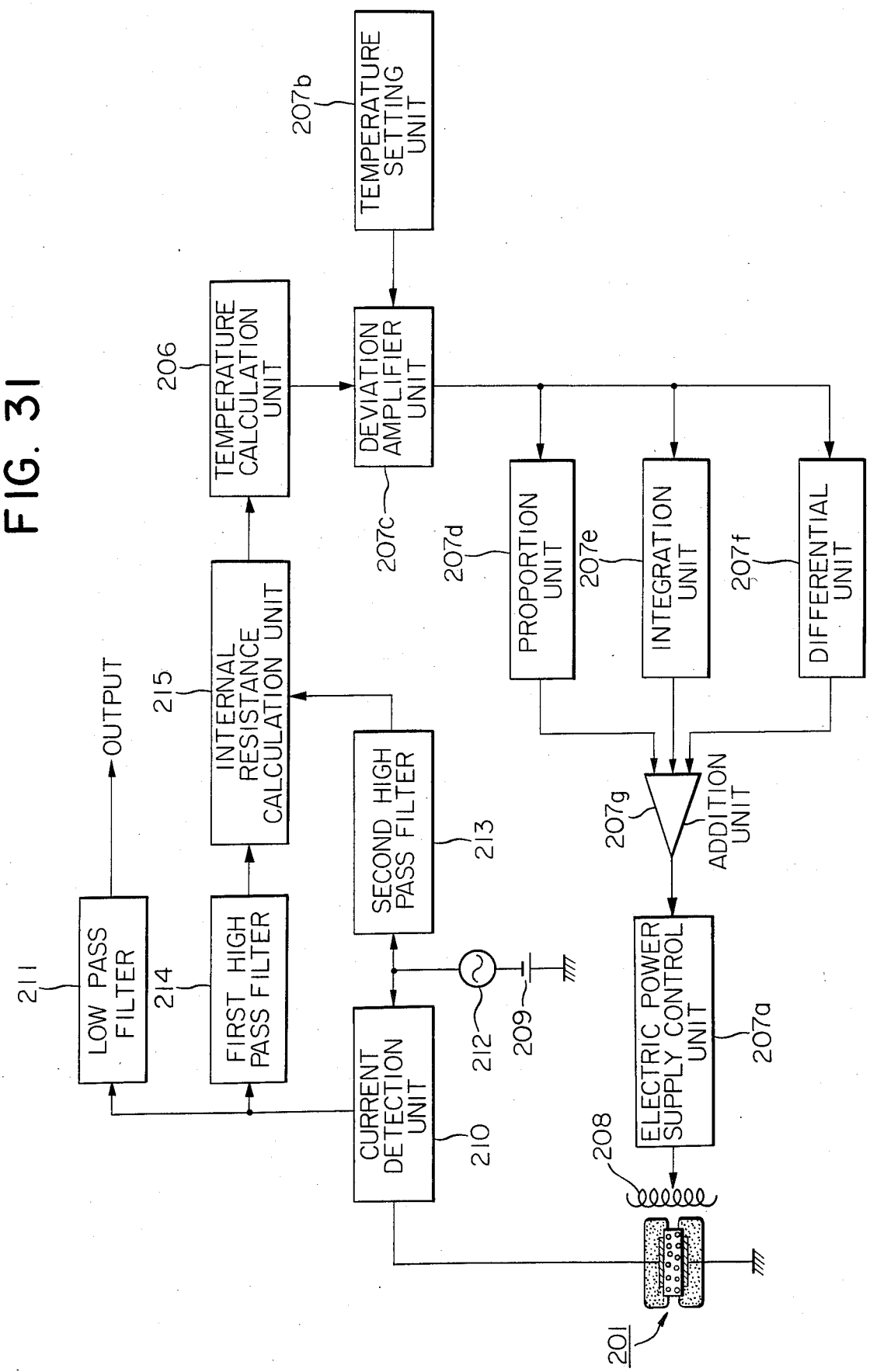
FIG. 31 is a block diagram of a limiting electric current type oxygen concentration detector in accordance with the fourth modification of the first embodiment of this invention wherein direct current is employed for measurement of a limiting current and alternative current is employed for measurement of an internal resistance.

FIG. 31 shows a block diagram of a limiting current type oxygen concentration detector wherein direct current is employed for measurement of a limiting current and alternative current is employed for measurement of an internal resistance.

The principle on which an internal resistance is measured employing an alternative current will be described below. FIG. 32 shows the locus of a frequency responsive to each component of impedance of a voltage (a current) in the excess voltage domination range applied to a limiting current type oxygen concentration sensor. Referring to the figure, albeit the amount of reactance component is zero for direct current and the frequency of which the amount is infinity, reactance component is available for the other frequency range. An equivalent circuit shown in FIG. 33 can represent the characteristics of a sensor shown in FIG. 32. A resistance Rb corresponds to the internal resistance in the resistance domination range. A resistance $R_D$ corresponds to a resistance existing along the surface separating an oxygen ionic conductor and an electrode in the excess voltage domination range. A capacity $C_D$ corresponds to an electrostatic capacity existing along the surface separating an oxygen ionic conductor and an electrode.

Therefore, various methods are available for measurement of an internal resistance Rb in the excess voltage domination range as tabulated below:

(a) Acquire the absolute value of an impedance employing frequency approximately $1/2\pi C_D R_b$ or more, on the assumption that the amount can be recognized as an approximate value of Rb, (b) Based on the foregoing method, calculate the resistance component from a combination of the absolute value and phase angle of the impedance, and (c) A plurality of frequency is employed for measurement of the absolute value and phase angle of an impedance, before each circuit constant of the equivalent circuit is obtained.

Among the three methods shown above, the method (a) is most simple and convenient. The frequency is required to be selected in the optimum range following the size and the production method of a sensor element. A frequency range 500 (Hz) through 100 (KHz) is suitable.

Referring to FIG. 31, the indicated as 209 is a direct current power supply unit which is required to measure a limiting current. The indicated as 210 is a current detection unit. A low pass filter 211 functions to pick up the direct current component contained in an electric current which contains both alternative current and direct current components and which is detected employing the current detection unit 210. The indicated as 212 is an alternative current power supply unit which is required to measure an internal resistance. A second high pass filter 213 functions to pick up the alternative current component contained in an applied voltage containing both alternative current and direct current components.

A first high pass filter 214 functions to pick up the amount of the alternative current component contained in an electric current which contains both alternative current and direct current components and which is detected employing the current detection unit 210. An internal resistance calculation unit 215 divides the alternative current component contained in an applied voltage by the amount of the alternative current component picked up from the output current of the current detection unit 210, for the purpose to calculate the internal resistance. The other units are same as the corresponding units shown in FIG. 26. It is of course possible to rectify the both outputs of the second high pass filter 213 and the first high pass filter 214 before a calculation is carried out for acquisition of an internal resistance. Further, it is possible to eliminate the second high pass filter 213, when the voltage of the alternative current power supply 212 is fixed at a constant amount and the internal resistance is calculated employing the inverse number of the output of the first high pass filter 214. It is possible to eliminate the calculation of an inverse number, when the temperature is calculated from a conductance (an inverse number of an internal resistance) rather than from a resistance. It is possible to eliminate the calculation of a temperature, provided a temperature control is carried out following the output of the second high pass filter 213. The temperature calculation unit 206 can be constructed as shown by a combination of 206b through 206f in FIG. 28, by a combination of 206c through 206m in FIG. 29, or by a combination of 206c through 206f in FIG. 30.

Figure 34:
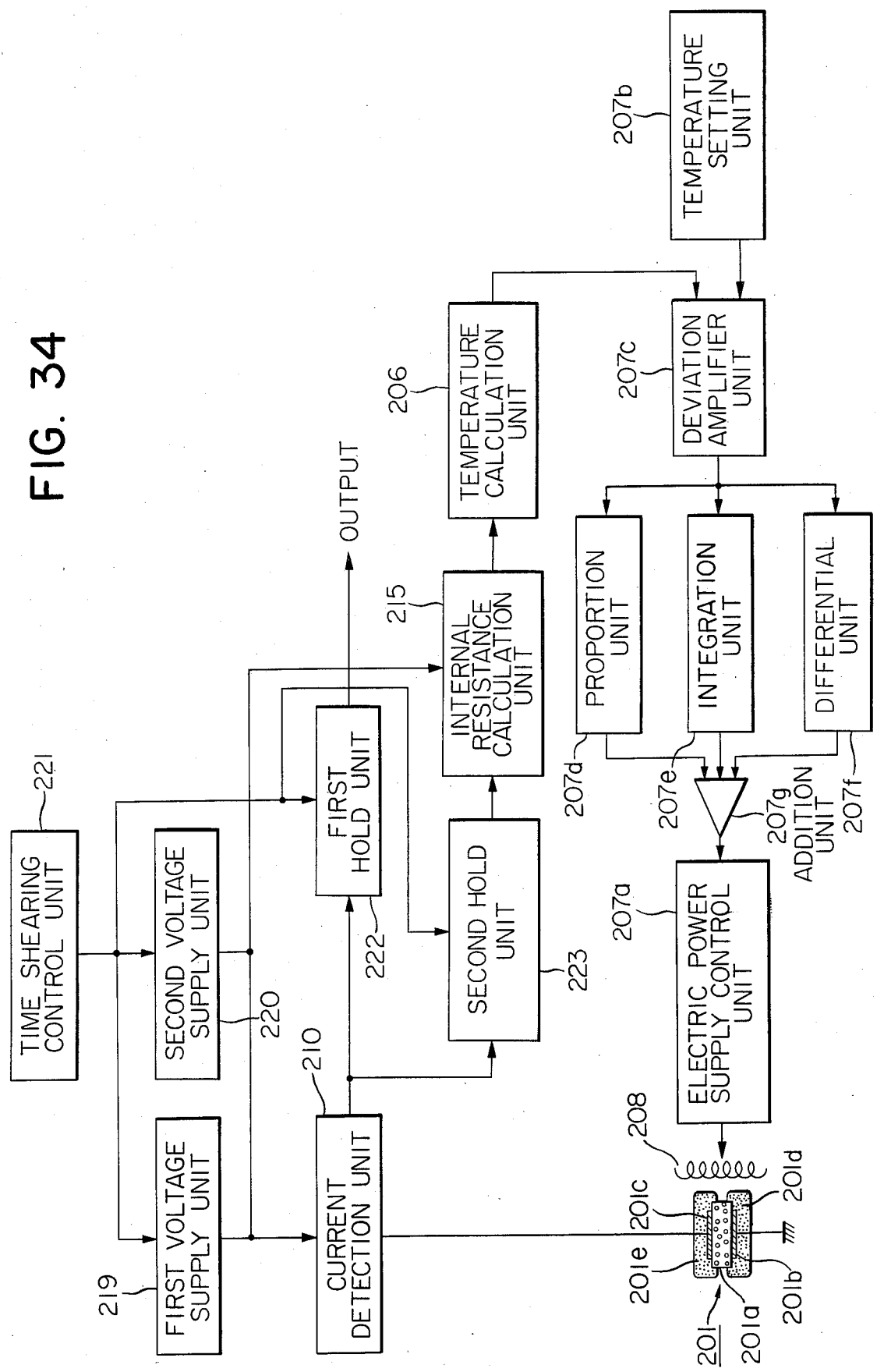
FIG. 34 is a block diagram of a limiting electric current type oxygen concentration detector in accordance with the fourth modification of the first embodiment of this invention wherein a time sharing system is introduced for simultaneous measurement of a limiting current and an internal resistance.

FIG. 34 shows a block diagram of a limiting current type oxygen concentration detector wherein a time shearing system is employed for simultaneous measurement of a limiting current and an internal resistance. A first voltage supply unit 219 functions to supply a voltage for measurement of a limiting current during the first period. A second voltage supply unit 220 functions to supply a voltage for measurement of an internal resistance during the second period. A time shearing control unit 221 alternatively allocates time for the first period and the second period. A first hold unit 222 holds or memorizes the amount of limiting current during the second period in which the measurement of the limiting current is not carried out. A second hold unit 223 holds or memorizes the amount of internal resistance during the first period in which the measurement of the internal resistance is not carried out. The other units are same to as shown in FIG. 28. As was described in the description presented with reference to FIG. 31, the temperature calculation unit 206 can be constructed as shown by a combination of 206b through 206f in FIG. 28, by a combination of 206c through 206m in FIG. 29, or by a combination of 206c through 206f in FIG. 20.

The function of and the conditions to be set in the circuit shown in FIG. 34 will be described below. The first voltage supply unit 219 required to output a voltage suitable for measurement of a limiting current, the voltage being determined following the oxygen concentration measurement range, the concentration of combustion products, the composition of an electrode et al. It is preferable to select the voltage to a voltage close to the maximum voltage in the excess voltage domination range corresponding to the minimum amount of the oxygen concentration measurement range. The second voltage supply unit 220 is required to output a voltage suitable for measurement of an internal resistance. Therefore, the voltage is required to be selected to be further less (e.g. less than 0.7 times) than the minimum amount of the excess voltage domination range corresponding to the minimum amount of the oxygen concentration measurement range. In other words, the voltage should be selected from the resistance domination range, albeit some other operation conditions should also be paid attention. Either an alternative-current voltage or a direct-current voltage is allowed as this voltage.

The preferable frequency of time shearing and the allocation of the time to the first and second periods will be described below. It is not necessary to allocate a same length of time both to the first and second period. Since the combustion of an internal combustion engine et al. has a tendency to change the oxygen concentration of the exhaust gas thereof much more rapidly than it changes the temperature of the exhaust gas thereof, it is advantageous to allocate a longer time to the first period in which the oxygen concentration is measured. A higher frequency of time shearing is preferable, because this improves the response of the detector, within the frequency range in which the current can faithly follow the voltage e.g. the frequency range not exceeding 1 (KHz). The internal resistance calculation unit 215 functions to divide the amount of the output voltage of the second voltage supply unit 220 by the amount of the current which was measured during the second period and has been held. In the case where the second voltage supply unit 220 is fixed at a constant value, it is possible to obtain an internal resistance by multiplying a proportion constant to an inverse number of a current, after the inverse number is calculated. It is possible to obtain an internal resistance from a voltage, when a constant current is also flowed. The temperature calculation unit 206 functions to obtain a temperature from a resistance employing the relations shown in the formula 13.

Figure 35:
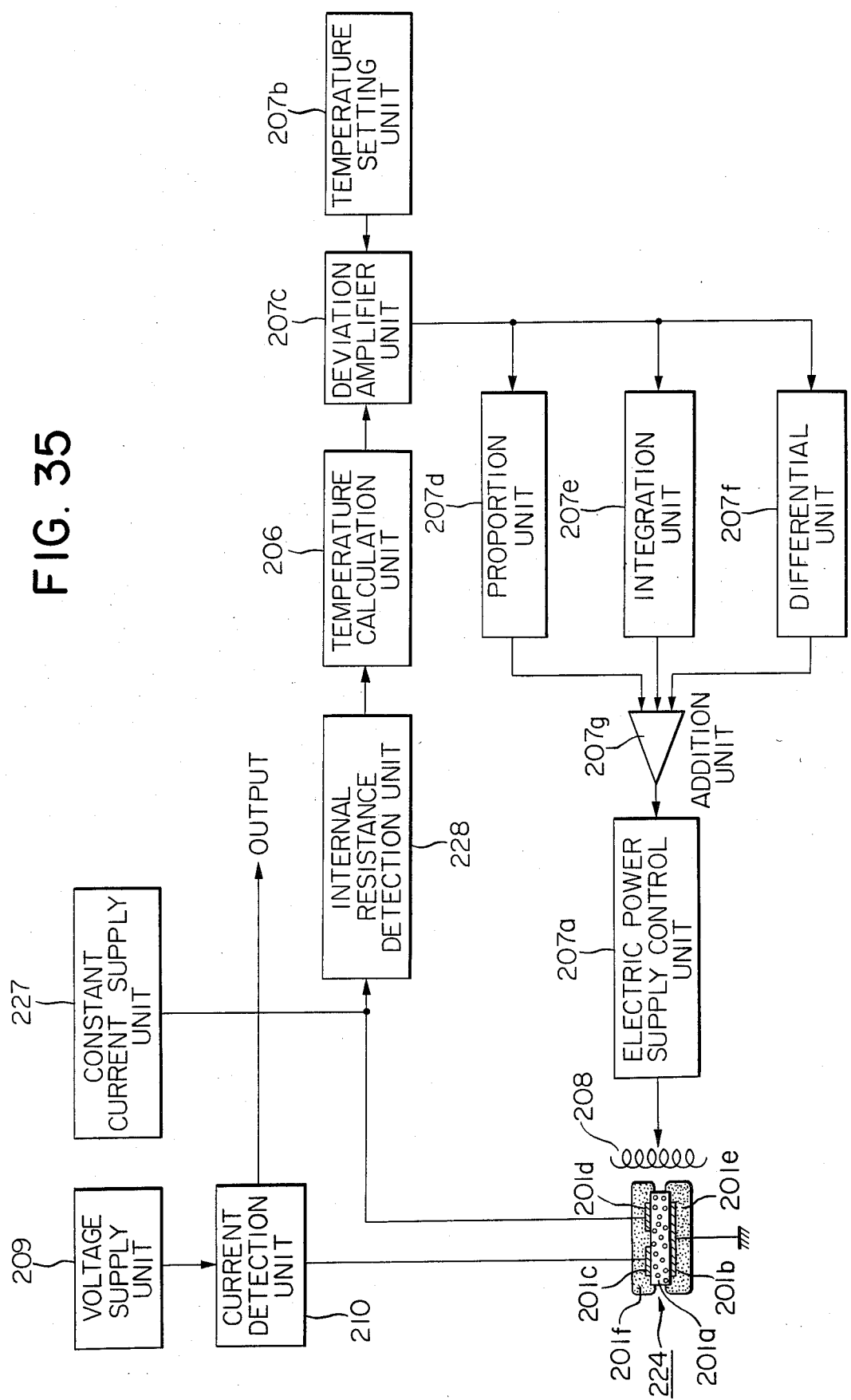
FIG. 35 is a block diagram of a limiting electric current type oxygen concentration detector in accordance with the fifth modification of the first embodiment of this invention wherein a limiting current type oxygen concentration sensor provided with a component for measuring the internal resistance shown in FIG. 19

FIG. 35 shows a block diagram of a limiting current type oxygen concentration detector wherein a limiting current type oxygen concentration sensor provided with a component for measuring the internal resistance shown in FIG. 19 or FIG. 20. A limiting current type oxygen concentration sensor 224 is provided with a component for measuring an internal resistance (an internal resistance detection side), in addition to a component for measuring a limiting current (a limiting current detection side). The internal resistance detection side is provided with an oxygen ionic conductor 201a having an electrode 201d arranged on one surface thereof and the other electrode 201b arranged on the other surface thereof. The limiting current detection side is provided with a cathode covered by a member which limits gas diffusion toward the cathode. The electrode 201b functions for the both sides.

An electrode 201c of the limiting current detection side is connected to a limiting current measurement unit consisting of the voltage supply unit 209 and the current detection unit 210. The electrode 201d of the internal resistance detection side is connected to an internal resistance measurement unit consisting of a constant current supply unit 227 and the internal resistance detection unit 228. As described in the description presented with reference to FIG. 34, the temperature calculation unit 206 can be constructed as a combination of 206b through 206f shown in FIG. 28, as a combination of 206c through 206m shown in FIG. 29, or as a combination of 206c through 206f shown in FIG. 30.

Since this oxygen concentration detector has two independent sensors of which the functions are different from each other, this detector does not require a time shearing system which was required by the detector shown in FIG. 34 and a system for superposition and division of voltage and/or current which was required by the detector shown in FIG. 31.

LIMITING ELECTRIC CURRENT TYPE OXYGEN CONCENTRATION DETECTOR IN ACCORDANCE WITH THE SECOND EMBODIMENT OF THIS INVENTION

A limiting current type oxygen concentration detector in accordance with the second embodiment of this invention of which the major purpose is to prohibit an error caused by the inherent nature of an oxygen concentration sensor or the dependence of the limiting current of the sensor upon temperature, from occurring, is based on an idea that the detector is provided with a means for measuring the internal resistance of the sensor and with a control means to set off an error with the internal resistance thereof measured employing the foregoing means for measuring the internal resistance.

FIG. 36 shows a block diagram of a limiting current type oxygen concentration detector in accordance with the second embodiment of this invention. This limiting current type oxygen concentration detector is provided with a limiting current type oxygen concentration sensor 301, a limiting current measurement unit 304 for measuring a limiting current which flows responsive to a voltage in the excess voltage domination range which is applied to the sensor 301, a temperature measurement unit 305 for measuring the temperature (the internal resistance) of the sensor 301, a temperature correction coefficient calculation unit 306 for calculating the temperature correction coefficient following the measured temperature of the sensor 301, and a correction unit 307 for correcting the measurement output of the limiting current measurement unit 304 following the output of the temperature correction coefficient calculation unit 306.

The temperature measurement unit 305 can be constructed to measure the internal resistance of the limiting current type oxygen concentration sensor 301, before the internal resistance is employed for calculation of the temperature of the sensor 301.

The temperature correction is carried out by means of multiplying the function $(T/T_o)^{-m}$ which brings an error caused by the temperature dependence shown in FIG. 23, zero by the formula 8. Putting $\alpha(T)$ to the temperature correction coefficient, $$\alpha(T) = (T/T_o)^{-m} \qquad (19)$$

Referring to FIG. 36, the temperature correction coefficient calculation unit 306 calculates the foregoing temperature correction coefficient α(T), and a correction unit 307 multiply the calculated temperature correction coefficient α(T) by the output of the limiting current measurement unit 304 for the purpose to correct the output of the limiting current measurement unit 304.

As a result, a calculation in which an amount of limiting current (the formula 8) which depends on the temperature is multiplied by a temperature correction term α(T) eliminates the temperature dependence to give a limiting current which is proportional to the partial pressure of oxygen.

A calculation for obtaining $\alpha(T) = (T/T_o)^{-m}$ following the internal resistance of a sensor will be described below.

From the formulae 13 and 14, $$\alpha(T) = \left(\frac{T}{T_o}\right)^{-m} = \left\{\frac{KT_o}{E} \log_e\left(\frac{R}{R_o}\right) + 1\right\}^m \qquad (20)$$

By means of hardware or software, the formula 20 is calculated, before the measured amount of limiting current is multiplied by α(T). However, this system is involved with a drawback in which the construction is rather complicated, because the formula 20 contains a logarithm calculation and a power calculation.

Therefore, it is a good idea to employ some approximation, in the case where a more attention is paid to simplicity and convenience rather than to accuracy.

The logarithm calculation term is simplified by means of replacement of the logarithm calculation term by the formula 15.

$$\left(\frac{T}{T_o}\right)^{-m} \approx \left\{\frac{KT_o}{E}\left(2\frac{\frac{R}{R_o} - 1}{\frac{R}{R_o} + 1}\right) + 1\right\}^m \qquad (21)$$

The power calculation term is simplified to $$\left(\frac{T}{T_o}\right)^{-m} \approx 1 + 2m\frac{KT_o}{E} \frac{R - R_o}{R + R_o} \qquad (22)$$

This simplification is based on an idea that $$Z_1 = (1+x)^m \qquad (23)$$

is equivalent to $$Z_2 \approx (1 + mx) \qquad (24)$$

Since x is much less than 1 in the temperature range of this sensor, 600 (°C.) through 1,000 (°C.), the formula 24 can be approximated with the formula 23 within the error of 1 (%).

In the case where the formula 16 is employed, the temperature correction term can be represented by $$\left(\frac{T}{T_o}\right)^{-m} \approx 1 + m\frac{KT_o}{E}\left(\frac{R}{R_o} - 1\right) \qquad (25)$$

This simplification eliminates logarithm calculations and power calculations. As a result, the formula 22 includes additions, subtractions and divisions only and the formula 25 includes additions and subtractions only. This is effective to simplify the construction of the calculation units and to decrease the production cost of the calculation units.

It is possible to employ some means other than a method which utilizes the internal resistance of a sensor e.g. a thermo-sensitive element, a thermo-couple et al. for the measurement of the temperature of a sensor.

As described earlier with reference to FIG. 32 or FIG. 33, alternative-current can be employed for measurement of the internal resistance of a limiting-current type oxygen concentration sensor.

FIG. 37 shows the fundamental circuit construction of a limiting current type oxygen concentration detector wherein alternative current is employed for measurement of the internal resistance of a limiting current type oxygen concentration sensor.

An atlernative-current and direct-current superposed voltage supply unit 312 supplies a voltage to a limiting current type oxygen concentration sensor 301 having 2 terminals through a current detector 313. A current signal detected by the current detector 313 is applied to an alternative-current direct-current separator 314 which can be a combination of a high pass filter and a low pass filter and which separates the current signal to the direct current component and the alternative current component. The direct current component is a limiting current which represents the oxygen concentration of the sensor 313. An internal resistance calculation unit 315 is applied the alternative current component and an alternative-current voltage outputted by an alternative-current oscillator 318 for the purpose to calculate the internal resistance of the sensor 313. Following the determined amount of the internal resistance, a temperature correction coefficient α(T) is calculated by a temperature correction coefficient calculator 316 employing any of the formula 20, 22, 25 et al. This determined amount of temperature correction coefficient α(T) is applied to a correction unit 317 to correct the direct current component or the limiting current. As described above, the internal resistance calculation unit 315, the temperature correction coefficient calculator 316 and the correction unit constitute a compensation unit 320 which compensates the dependence of the output upon the temperature.

A means for the logarithm calculation for $\log_e(R/R_o)$ included in the first term of the right side of the formula 20 can be readily constructed employing a logarithm convertion module 4366 (or 4367) produced by Teledyne Fillbrick et al.

A means for the power calculation included in the right side of the formula 14 can be readily constructed employing a power function module 4371 et al. produced by Teledyne Fillbrick et al.

FIG. 38 shows a block diagram of a limiting current type oxygen concentration detector of which the temperature correction coefficient calculation unit is composed employing the formula 22. The combination of a direct-current voltage power supply 321 and a fixed alternative current supply unit 322 supplies a voltage or a current of a direct current component superposed by an alternative current component to a limiting current type oxygen concentration sensor 301. A current voltage converter 323 functions to pick up the current flowing in the sensor 301 or the voltage appearing across the sensor 301. A low pass filter 324 selects the direct current component or the limiting current out of the output of the current voltage converter 323. The limiting current is applied to a multiplier 326. The alternative current component selected by a high pass filter 325 is rectified in a rectifier 327, before it is applied to a circuit which is designed to output a voltage proportional to the internal resistance of the sensor 301. Since the sensor 301 is applied with a fixed amount of alternative current voltage, this detector does not require an internal resistance calculation unit 315 shown in FIG. 37, unlike the foregoing detector. The preferable frequency range is 500 (Hz) through 50 (KHz) and the preferable range of the alternative current is 1 through 100 (mV) in terms of the voltage across the terminals of the sensor 301.

It is possible to replace the fixed alternative-current supply unit 322 with a fixed alternative-current voltage power supply. In this case, it is possible to obtain an amount proportional to the internal resistance of the sensor 301, when employing an inverse number of the rectified output in addition to the output of the current voltage converter 323 as the input of the high pass filter 325.

The temperature correction coefficient calculation unit functions to conduct the calculation of the formula 22. A combination of three components including a power supply 328 and resistances 329 and 330 conducts an approximate addition of (R+Ro) included in the formula 22. A combination of three components including a power supply 331 and resistances 332 and 333 conducts an approximate subtraction of (R−Ro) included in the formula 22. A divider 334 conducts a calculation of $$\left( \frac{R - Ro}{R + Ro} \right)$$

included in the formula 22. A combination of four components including a power supply 328, resistances 335 and 336 and a potentiometer 337 conducts an approximate calculation of $$\left( 1 + 2m \frac{KTo}{E} \frac{R - Ro}{R + Ro} \right)$$

included in the formula 22.

It is possible to employ an adder rather than a resistance circuitry to improve the calculation accuracy.

A multiplier 326 conducts a multiplication of the temperature correction coefficient obtained above and the measured amount of limiting current to output an output applied with the temperature compensation. It is required to reajust the potentiometer 337 for a sensor having a different amount of temperature coefficient.

FIG. 39 shows a block diagram of a limiting current type oxygen concentration detector of which the temperature correction coefficient calculation unit is composed employing the formula 25. The difference from the detector shown in FIG. 38 is that this detector is provided with a temperature correction coefficient calculation unit composed based on the formula 25. In other words, the temperature correction term included in the formula 25 is calculated by means of a fixed voltage supply 338 and of a combination of resistances 339 and 340 and a potentiometer 341. This simplifies the construction of the temperature correction coefficient calculation unit. It is required to readjust the fixed voltage power supply 338 or the potentiometer 341 for a sensor having a different amount of temperature coefficient.

Figure 40:
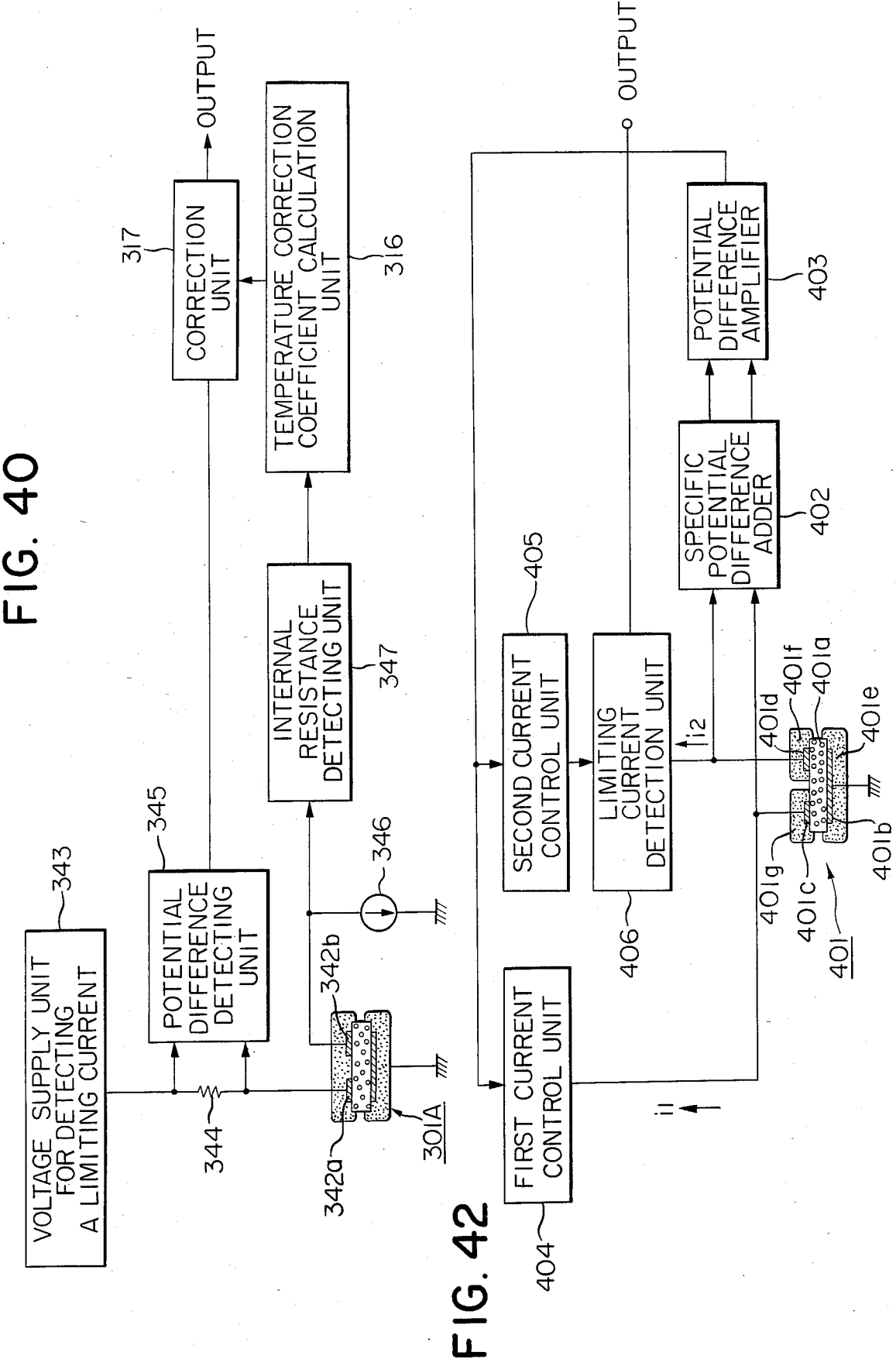
FIG. 40 is a block diagram of a limiting electric current type oxygen concentration detector in accordance with the fourth modification of the second embodiment of this invention, wherein a limiting current type oxygen concentration sensor provided with a component for measuring the internal resistance shown in FIG. 19

FIG. 40 shows a block diagram of a limiting current type oxygen concentration detector provided with a limiting current type oxygen concentration sensor 301A provided with a component for measuring an internal resistance. This oxygen concentration sensor 301A has a portion which is composed of an oxygen ionic conductor having a cathode 342a arranged on one surface thereof and covered by a member which limits the oxygen diffusion toward the cathode 342a and an anode arranged on the other surface thereof and which functions to detect a limiting current (a portion for detecting a limiting current) and the other portion which is composed of an oxygen ionic conductor having an electrode 342b arranged on one surface thereof and the other electrode arranged on the other surface thereof and which functions to detect an internal resistance (A portion for detecting an internal resistance). the portion for detecting a limiting current is applied a voltage in the excess voltage domination range, and the portion for detecting an internal resistance is applied a voltage in the resistance domination range or is supplied a current in the resistance domination range. Therefore, changeover, superposition and/or separation are or is unnecessary for this detector.

Figure 41:
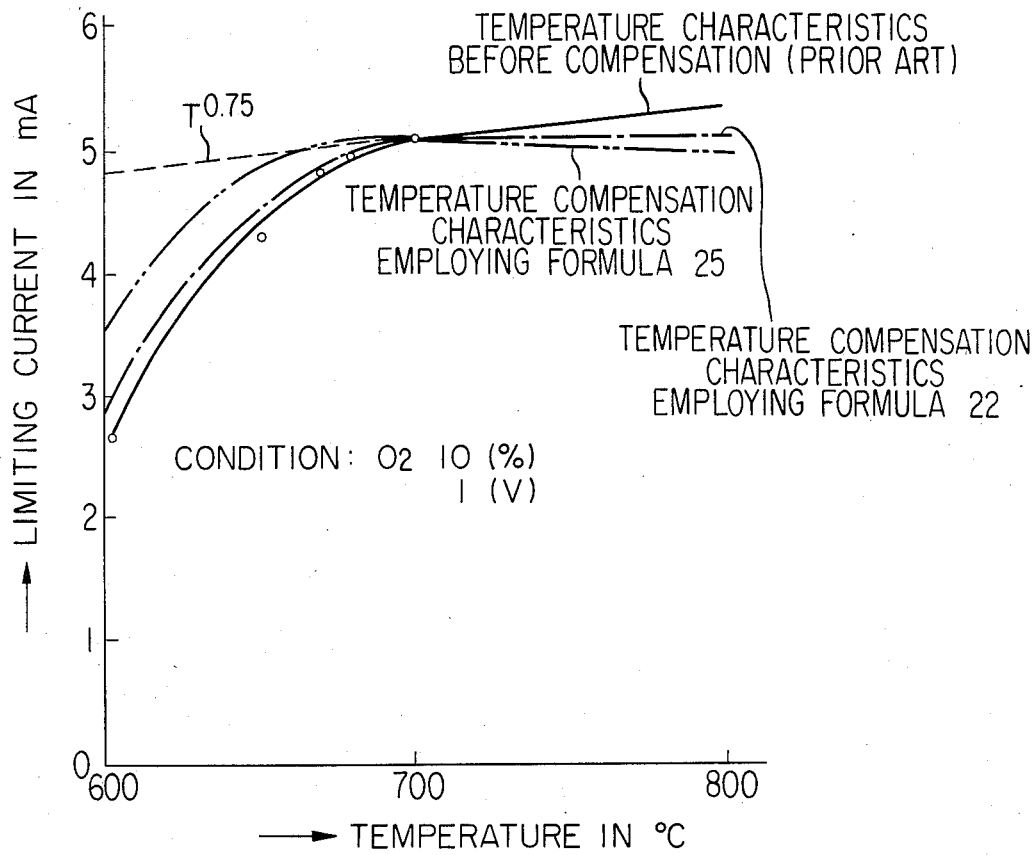
FIG. 41 is a graph showing the effect of temperature compensation realized by the second embodiment of this invention.

FIG. 41 shows the effect of temperature compensation realized by the second embodiment of this invention. As is clear from FIG. 41, the dependence of the limiting current upon temperature is considerably decreased for a limiting current type oxygen concentration detector in accordance with the second embodiment of this invention. Therefore, the accuracy is considerably improved and the temperature range allowing measurement is considerably increased.

Even in the case of a simplified construction based on the formula 25, a magnitude of the temperature compensation similar to that of the accurate version is realized. As shown in FIG. 27, the approximation formula 16 is unsatisfactory in comparison with the logarithm formula 14 in the range 0.6>R/Ro and R/Ro>1.4. The reason why the temperature compensation characteristics employing the approximation formula 25 based on the formula 16 is better than that employing the approximation formula 20 based on the formula 14 or the approximation formula 22 based on the formula 15, is that (a) the limiting current vs. temperature relations is not linear as shown by a broken line in FIG. 23 but falls sharply in the low temperature range as shown by a full line in FIG. 23, (b) the incline of the formula 16 is adjusted to exhibit a logarithmic function in a higher temperature range and to deviate from a logarithmic function in a lower temperature range. The multiplier 326 shown in FIGS. 38 and 39 can be replaced by an element which varies the internal resistance thereof in response to a signal voltage applied to the gate thereof such as an field effect transistor.

LIMITING ELECTRIC CURRENT TYPE OXYGEN CONCENTRATION DETECTOR IN ACCORDANCE WITH THE THIRD EMBODIMENT OF THIS INVENTION

As is shown in FIG. 23, the amount of limiting current is much lower in a low temperature range than the amount following the inherent characteristics in which a limiting current is proportional to $T^{0.75}$. This is because the internal resistance extremely increases in a low temperature range. The object of the third embodiment of this invention is to correct the detected amount of limiting current following an amount of voltage-drop due to the internal resistance of a sensor and which is assumed following a measured amount of internal resistance of a sensor for the ultimate purpose to remove the error of limiting current caused by a low temperature.

The conceptual construction of a limiting current type oxygen concentration detector in accordance with the third embodiment of this invention and various modification thereof will be described below with reference to drawings. The modifications are classified into three. This classification is based on whether or not a sensor employed an electrode which is exclusively employed for measurement of an internal resistance thereof (whether or not the sensor has 2 terminals or 3 or 4 terminals) and on the means by which a voltage is applied to or a current is supplied to the sensor, for measurement of the internal resistance and/or for measurement of the limiting current.

(a) A limiting current type oxygen concentration sensor included in the first category is provided with an oxygen concentration sensor having 3 or 4 terminals.

(b) A limiting current type oxygen concentration sensor included in the second category is provided with an oxygen concentration sensor having 2 terminals and with a means for application of a voltage for the measurement based on the time shearing system.

(c) A limiting current type oxygen concentration sensor included in the third category is provided with an oxygen concentration sensor having 2 terminals and with two different power supply for the measurement the one of which is alternative current for measurement of an internal resistance and the other of which is direct current for measurement of a limiting current.

It is noted that limiting current type oxygen concentration sensors in accordance with the modifications of this embodiment are not necessarily limited to those clasified in the three categories.

(a) Limiting current type oxygen concentration detectors provided with a sensor having 3 or 4 terminals Referring to FIG. 42, a limiting current type oxygen concentration sensor 401 is provided with an oxygen ionic conductor 401a, an electrode 401b arranged on one surface of the oxygen ionic conductor 401a, an electrode 401c for measuring an internal resistance and an electrode 401d for measuring a limiting current both of which are arranged on the other surface of the oxygen ionic conductor 401a.

The oxygen ionic conductor 401a is a replete plate produced of a solid solution including one or more substances selected from $ZrO_2$, $HfO_2$, $ThO_2$, $Bi_2O_3$ et al. and one or more slabilizers selected from CaO, MgO, $Y_2O_3$, $Yb_2O_3$ et al. The electrodes 401b, 401c and 401d are produced of an electric conductor of a refractory nature which is a substance selected from Pt, Ag, Rh, Ir, Pd et al. or an alloy of these materials. The electrode 401d from which an electric current flows out is covered by a porous material layer 401f which functions to regulate the oxygen quantity flowing toward the electrode 401d. The electrode 401b is covered by a porous material layer 401e to be protected from contamination of foreign materials. The electrode 401c is covered by a porous material layer 401g. The porous material layer 401e, 401f or 401g is an inorganic material of a refractory nature e.g. alumina, magnesia, spinel, mullite et al. The porosity of the porous material layer 401e is preferable to be larger than that of the porous material layer 401f, because the function of the porous material layer 401e is simply to drain oxygen, albeit the function of the porous material layer 401d is to regulate the quantity of oxygen diffusing therethrough. The electric potential of the electrode 401c for measuring an internal resistance and of the electrode 401d for measuring a limiting current is applied to a potential difference amplifier 403 through a specific potential difference adder 402. The output of the potential difference amplifier 403 is applied to the electrode 401c through a first current control unit 404 and to the electrode 401d through a second current control unit 405 and a current detection unit 406. The locations of the second current control unit 405 and the current detection unit 406 can be exchanged. The direction of the current flowing in the first current control unit 404 can be selected from the direction of the current flowing in the second current control unit 405. The intensity of current $i_1$ flowing in the first current control unit 404 is controlled to the approximately proportional to the intensity of the current $i_2$ flowing in the second current control unit 405. As a result of this control, the initial portions of the curves representing the current vs. voltage relations of the internal resistance detection component provided with the electrode 401c which initial portion is linear, become identical to each other and proportional to the straight line $C_1-C_2$ shown in FIG. 49, for a variation of the oxygen concentration of gases of which the oxygen concentration is measured.

Figure 43:
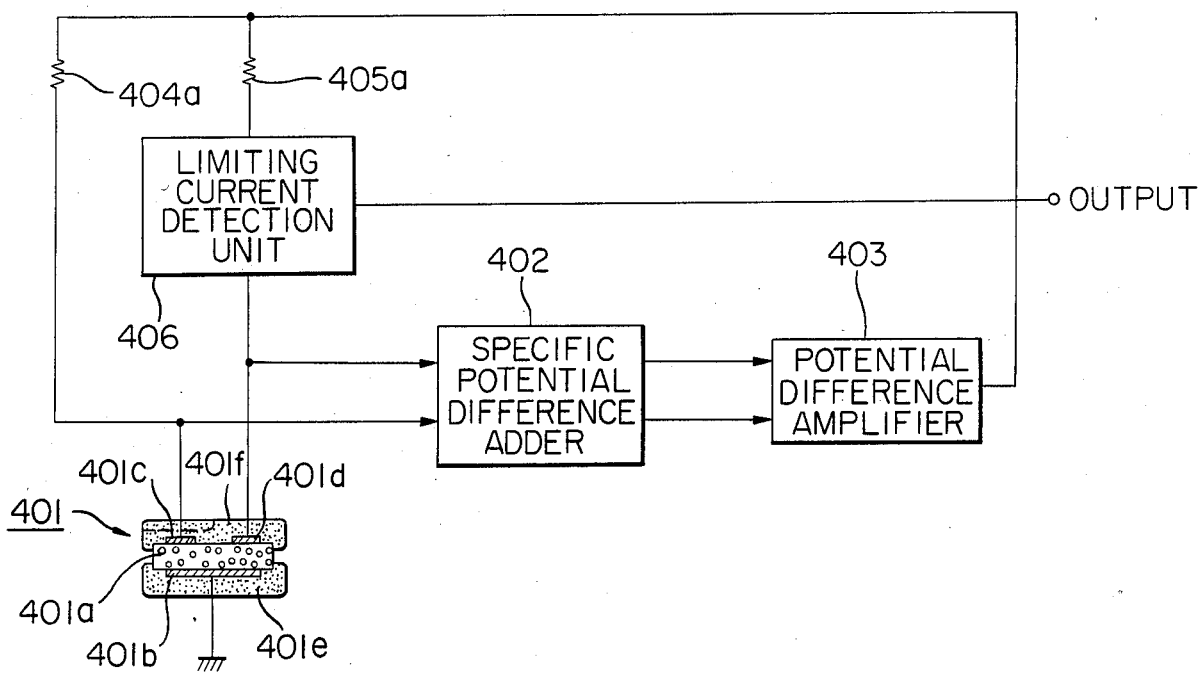
FIG. 43 is a block diagram of a limiting electric current type oxygen concentration detector in accordance with one modification of the third embodiment of this invention of which the fundamental construction is shown in FIG. 42.

In the case where the direction of the current $i_1$ is selected to be identical to that of the current $i_2$, the first current control unit 404 can be replaced by an internal resistance detection control resistance 404a, and the second current control unit 405 can be replaced by a limiting current detection control resistance 405a, as shown in FIG. 43 which shows a block diagram of a simplified circuit, which is inevitably involved with a less magnitude of proportionality. It is possible to compile a circuit shon in FIG. 44 in which a potential difference across a resistance 405a is detected rather than employing the current detection unit 406, for the ultimate purpose to obtain a limiting current.

Figure 49:
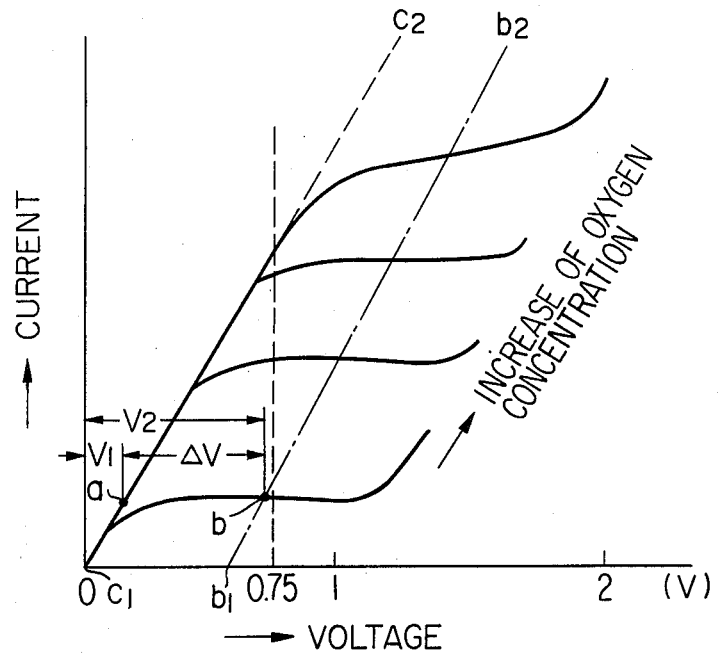
FIG. 49 is a graph showing the electric current vs. voltage relations employing the oxygen concentration as a parameter, of an exemplary limiting electric current type oxygen concentration sensor.

In the case where the porosity of the porous material layer 401g is selected to be larger than that of the porous material layer 401f, or in the case where the intensity of current of 401d is selected to be less than that of 401c which is regulated by the porosity of the porous material layer 401g under a condition that the both porous material layers have the same porosity each other, the electric potential of the internal resistance detection electrode 401c approximately represents the voltage-drop generated in the internal resistance of the sensor (For example, the point a shown in FIG. 49). On the other hand, the electric potential of the limiting current detection electrode 401d represents a sum of the voltage-drop generated in the internal resistance and the excess voltage caused by the regulation of the oxygen flow made by the porous material layer 401f (For example, the point b shown in FIG. 49). In response to an oxygen flow in the direction from the porous material layer 401f to the porous material layer 401e, the electric current flows from the electrode 401b to the electrode 401c and 401d. Therefore, the electric potential of the electrodes 401c and 401d is below the ground potential. Supposing the portion for detecting the internal resistance operates at the point a under a certain amount of oxygen concentration, the electric potential of the electrode 401c stands $-V_1$ with reference to the ground. In a similar manner, supposing the portion for detecting the limiting current operates at the point b, the electric potential of the electrode 401d stands $-V_2$. Therefore, it is possible to set off the potential difference between the electrodes 401c and 401d, provided the specific potential difference adder 402 functions to subtract $\Delta V$ from $-V_1$ or to add $\Delta V$ to $-V_2$. This has an effect to control the input of the potential difference supplier 403 to decrease toward zero, provided the potential difference is amplified with a high amplification degree. In other words, in the case where the potential of the electrode 401c, in terms of the amount of the output of the specific potential difference adder, is less, the output potential of the potential difference amplifier becomes a larger amount below zero, and in the case where the potential of the electrode 401c is higher, the output potential of the potential difference amplifier becomes higher (less in terms of the absolute value of the output voltage), because $i_1$ and $i_2$ are so controlled. Finally, a control is made to make the input potential difference of the potential difference amplifier 403 zero. In other words, the electric potential of the electrode 401d for measurement of a limiting current is kept at the point b in FIG. 49, and this electric potential moves along the line $b_1$–$b_2$ in FIG. 49, following a variation of the oxygen concentration. Therefore, the foregoing regulation enables detection of the precise amount of a limiting current $i_2$, regardless of a variation of the internal resistance of a sensor. This phenomenon in which the operation point of the limiting current detection side moves along the line $b_1$–$b_2$ in FIG. 49 following a variation of the oxygen concentration is equivalent to that which is exhibited by a sensor which is additionally provided with a power supply having a negative internal resistance $r_3$, of which the amount is $$r_3 = -r_2 \times i_1/i_2 \qquad (26)$$

wherein, $r_2$ represents the ordinary or positive resistance of the internal resistance detection side of a sensor. The problem of self oscillation is generally inevitable for an electric circuit which generates a negative resistance therein. One of the requirements to prohibit self-oscillation from occurring for a circuit exhibiting a negative resistance is that the negative resistance is compensated by means of addition of a positive resistance having an amount larger than the negative resistance. This is equivalent to that the incline of a line $b_1$–$b_2$ in FIG. 49 is made larger than the incline of a line $c_1$–$c_2$ in FIG. 49 which represents the amount of the internal resistance of the limiting current detection side of a sensor. Regardless of the amount of a negative resistance $r_3$, it is absolutely possible to convert the overall resistance to a positive resistance by selecting a proper amount of $i_1/i_2$ to be applied to the formula 26. In the case where the both electrodes 401c and 401d are produced of the same material and the both porous material layers are produced of materials of which the nature is similar to each other and the both electrodes 401c and 401d flows the limiting current at a current density which is identical to each other, the eletric potential of the electrodes 401c and 401d does not become as described above, if the current density is selected to be same for $i_1$ as for $i_2$. In other words, a voltage difference $\Delta V$ is not generated between the point a and the point b. Therefore, the proportional relations for the first current regulation component and the second current regulation component is required to be set so that the current density of the electrode 401c of the internal resistance detection side becomes less (from the practical viewpoints less than 0.7 through 0.9 times) than the current density of the electrode 401d of the limiting current detection side.

A thiner porous material layer of the internal resistance detection side as shown by a broken line in FIG. 43 has an effect to allow much quantity of a gas to pass through the layer, resultantly increasing the current density of the limiting current flowing in the internal resistance detection side. This increased current density of the limiting current in the internal resistance detection side decreases the effect of an excess voltage caused by the limiting current, for the electrode 401c even under the same current density. As a result, since a correction is realized to compensate the component of voltage-drop generated in the internal resistance, the operating voltage of the electrode 401a of the limiting current detection side is caused to move along the line $b_1$–$b_2$ shown in FIG. 49. It is of course possible to produce an internal resistance detection side which does not exhibit the limiting current characteristics, if the electrodes 401c and 401d are separated by an electric conductor such as an electron conductor, a conductor for the exygen ions and a composite conductor.

It is not necessarily required to make the shape of a sensor abnormal as shown by a broken line in FIG. 43 and to increase the limiting current, for the purpose to prohibit the effect of an excess voltage for occurring. In other words, the current density of electrode of an internal resistance detection side which is les (0.01 through 0.7 times) then the current density of the electrode of a limiting current detection side is also effective to prohibit the effect of an excess voltage from occurring. This condition of the current density of the both sides can be realized by means of selection of the area of the electrode 401c larger than the area of the electrode 401d. However, since this decrease in the current density is accompanied by the corresponding decrease in the voltage-drop, it is required to amplify the voltage-drop component by a ratio corresponding to the decrease in the current density.

It is not necessarily required to arrange the electrode 401c of the internal resistance detection side parallel to the electrode 401d of the limiting current detection side, as shown in FIG. 42. In other words, these electrodes 401c and 401d are allowed to be arranged in a concentric location. Incidentally, it is of course possible to provide one opposite electrode to each of the electrodes 401c and 401d rather than providing one opposite electrode to the both of the electrodes 401c and 401d shown in FIG. 42. Situation is same for the oxygen ionic conductor. Namely, it is possible to provide one each oxygen ionic conductor respectively to the internal resistance detection side and to the limiting current detection side. Further, in this case, a material different from the material from the limiting current detection side is allowed to be selected for the internal resistance detection side. Such a material can be a thermo-sensitive material (e.g. thermistor) having a resistance temperature coefficient which is identical or close to that of the oxygen ionic conductor with which the limiting current detection side is produced.

Figure 47:
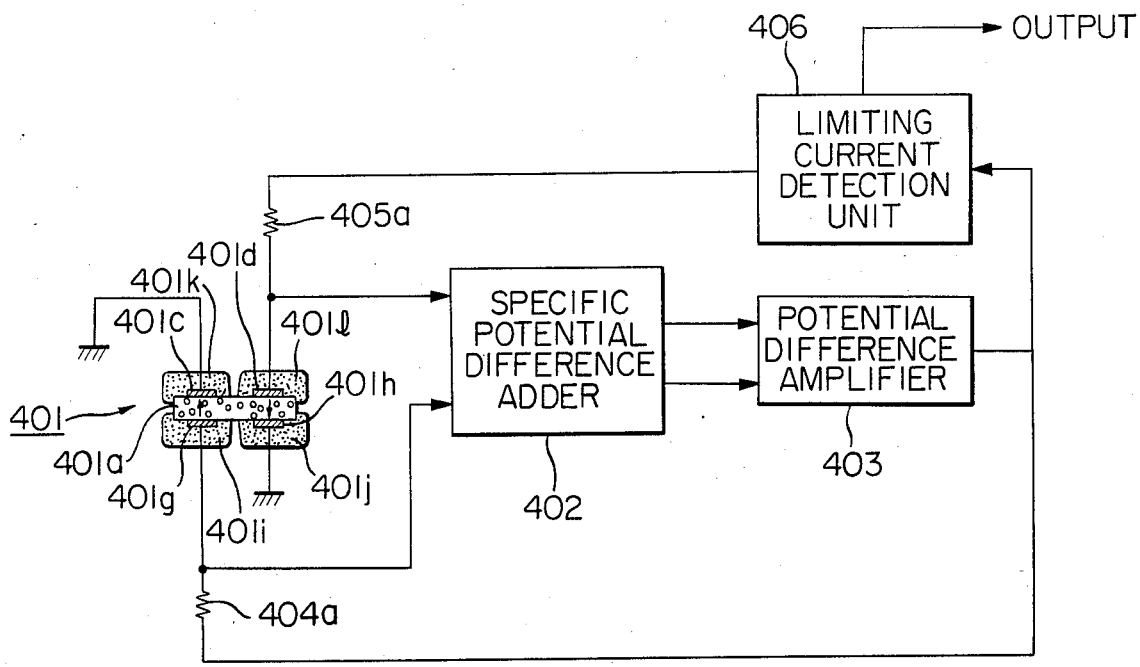
FIG. 47 is a block diagram of a limiting electric current type oxygen concentration detector in accordance with the fifth modification of the third embodiment of this invention of which the fundamental construction is shown in FIG. 42.
Figure 48:
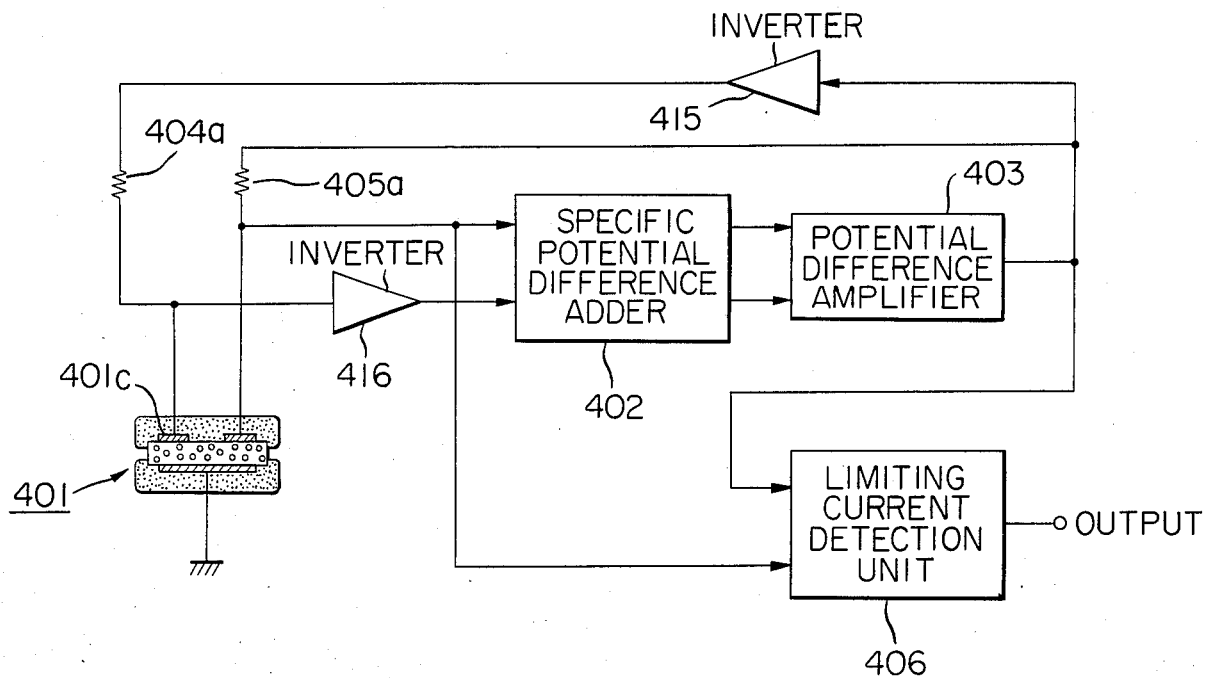
FIG. 48 is a block diagram of a limiting electric current type oxygen concentration detector in accordance with the sixth modification of the third embodiment of this invention of which the fundamental construction is shown in FIG. 42.

Unlike the case shown in FIG. 42, the direction of current for detection of the internal resistance of a sensor can be selected independently of the direction of current for detection of a limiting current flowing in the sensor. FIG. 47 shows a block diagram of a limiting current type oxygen concentration detector provided with a sensor of which the direction of current for detection of the internal resistance is different from the direction of current for detection of a limiting current. This configuration has an advangage in which the thickness of the porous material layer can be freely selected, because the functional surfaces faces toward opposite directions. Incidentially, howener, since the lateral flow of the oxygen ions in the directions between 401$k$ and 401$l$ must be prohibited from occurring, the internal resistance detection side and the limiting current detection side must be separated by at least a distance equivalent to the thickness of the oxygen ionic conductor. FIG. 47 shows a block diagram in which the electrodes 401$c$ and 401$h$ are grounded, the output of a potential difference amplifier 403 is applied to a resistor 404$a$ and the electric potential of an electrode 401$g$ is applied to a specific potential difference under 402. In this case, since the thickness of a porous material layer 401$j$ which is thinner than the thickness of a porous material layer 401$l$ enables the amount of the limiting current of the internal resistance detection side larger than the corresponding amount of the limiting current detection side, it is possible to prohibit an excess voltage from causing an adverse effect for measurement of the internal resistance, resulting in a possibility to correctly measure the internal resistance of a sensor. Further, since Il and Ii are not placed on the same surface, this causes an advantage in which a free selection is allowed for the porous material layers. Albeit the oxygen concentration detector shown in FIG. 47 is provided with a sensor having 4 terminals or 4 lead wires, the number of terminals or lead wires is decreased to 3 in the oxygen concentration detector shown in FIG. 48. In this case, the output of the electric potential amplifier 403 is inverted by an inverter 415, before it is applied to a resistor 404$a$. And, the electric potential of the electrode 401$c$ is inverted by an invertor 416, before it is applied to a specific electric potential adder 402. The function of this oxygen concentration detector is identical to that of the detector shown in FIG. 46.

Figure 44:
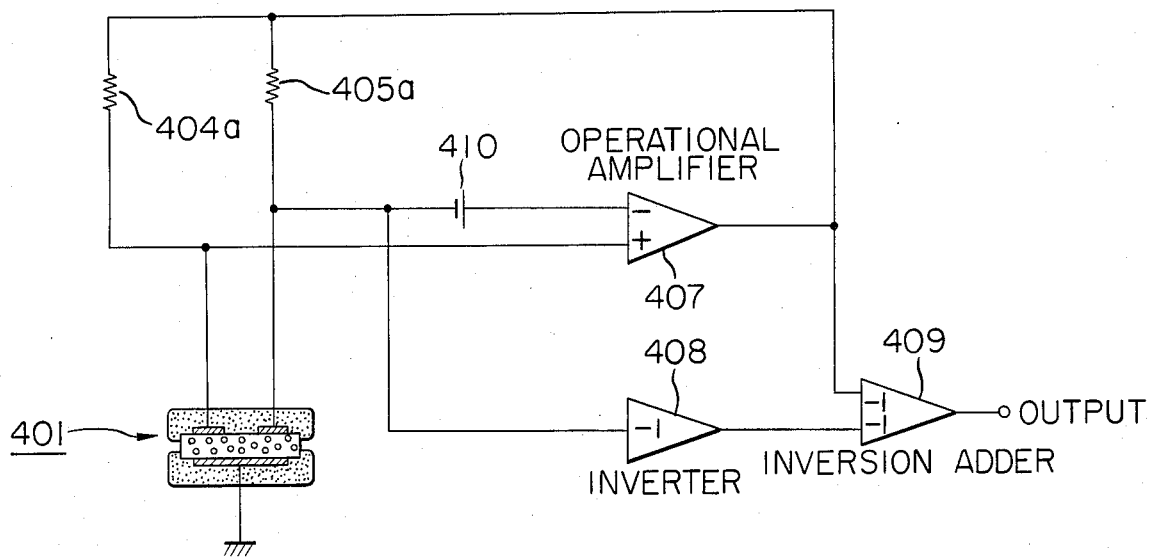
FIG. 44 is a block diagram of a limiting electric current type oxygen concentration detector in accordance with another modification of the third embodiment of this invention of which the fundamental construction is shown in FIG. 42.

FIG. 44 shows a block diagram of a limiting current type oxygen concentration detector in accordance with another modification of the third embodiment of this invention. Referring to the figure, a batter 410 functions to supply a specific amount of electric potential. An operational amplifier 407 amplifies an electric potential available across a positive input terminal and a negative input terminal. An inverter 408 inverts the polarity of a voltage. An inversion adder 409 adds the outputs of the operational amplifier 407 and an invertor 408. A combination of the invertor 408 and the inversion adder 409 enables to detect the electric potential generated across a resistor 405$a$. This voltage has an amount proportional to the amount of a limiting current.

Figure 45:
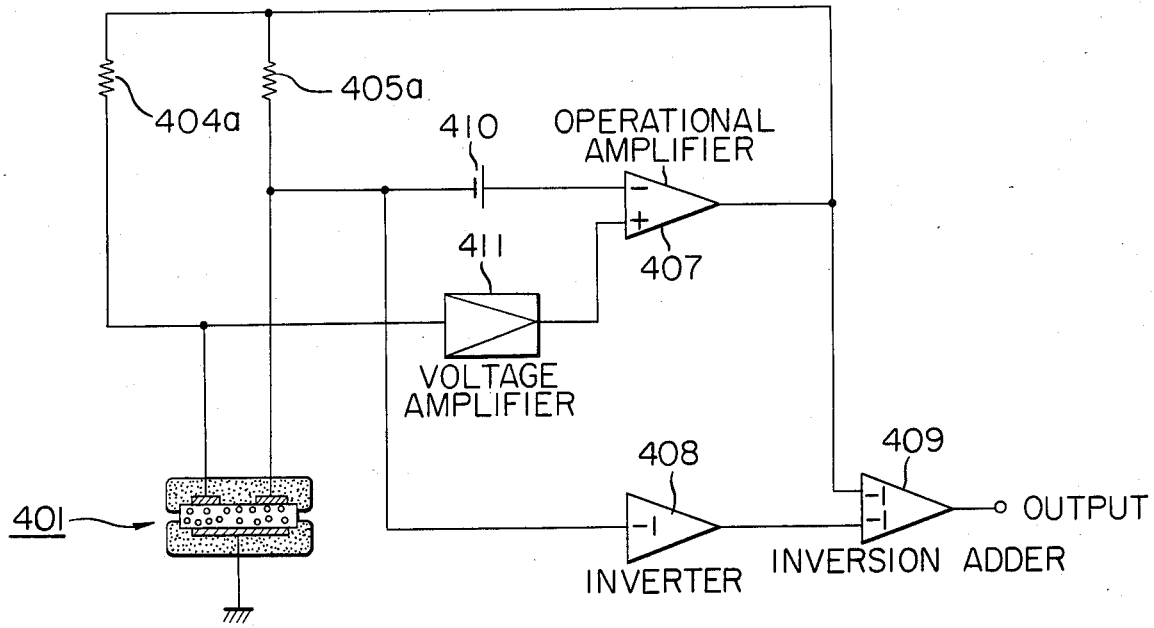
FIG. 45 is a block diagram of a limiting electric current type oxygen concentration detector in accordance with the third modification of the third embodiment of this invention of which the fundamental construction is shown in FIG. 42.

FIG. 45 shows a block diagram of a limiting current type oxygen concentration detector in accordance with the third modification of hthis invention. The amount of a resistance 404$a$ is selected to be larger that the amount of a resistance 405$a$ to decrease the current density of the internal resistance detection side. This is effective to remove the effect of a limiting current. The decrement in the amount of limiting current caused by a decrease of the current density is corrected employing a voltage amplifier 411, resultantly enabling to assume the voltage-drop which would be generated under the same current density.

Figure 46:
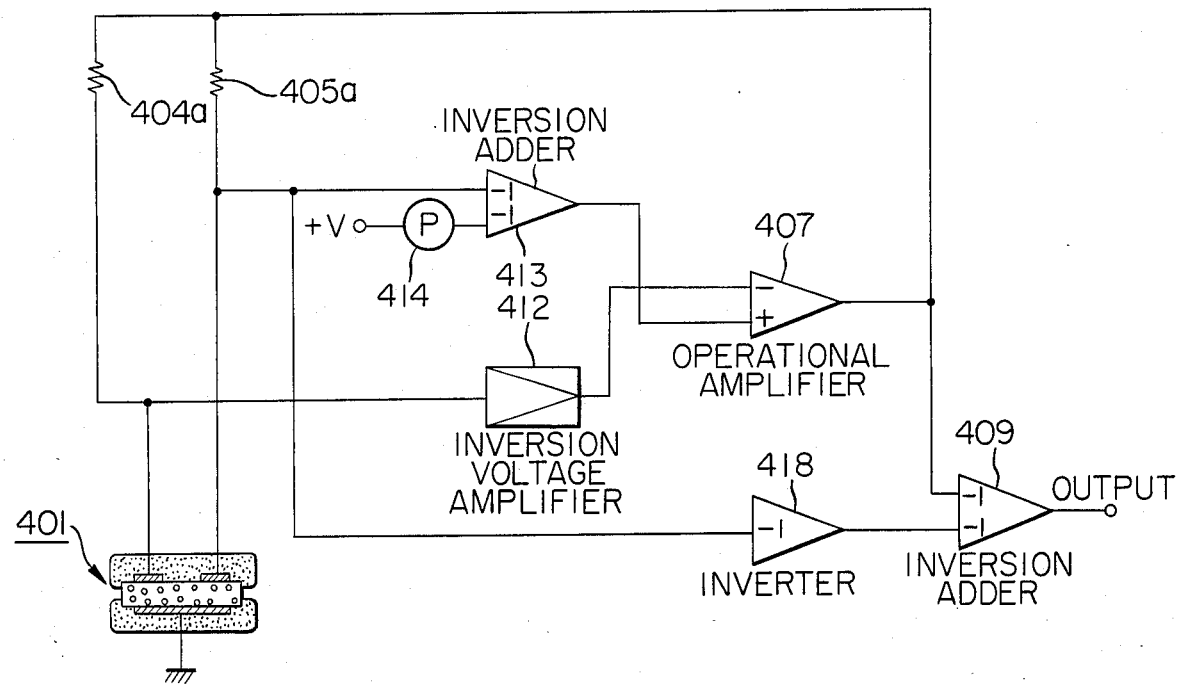
FIG. 46 is a block diagram of a limiting electric current type oxygen concentration detector in accordance with the fourth modification of the third embodiment of this invention of which the fundamental construction is shown in FIG. 42.

FIG. 46 shows a block diagram of a limiting current type oxygen concentration detector in accordance with the fourth modification of the third embodiment of this invention. A potentiometer 414 rather than the battery is employed. An inversion adder 413 and an input $+V$ are newly introduced. An inversion voltage amplifier 412 rather than an amplifier 411 is employed. Since the inversion adder 413 and the inversion voltage amplifier 412 function to invert the polarity of a voltage, the connection of the input terminal of an operational amplifier 407 is reversed in comparison with that shown in FIG. 44.

Figure 50:
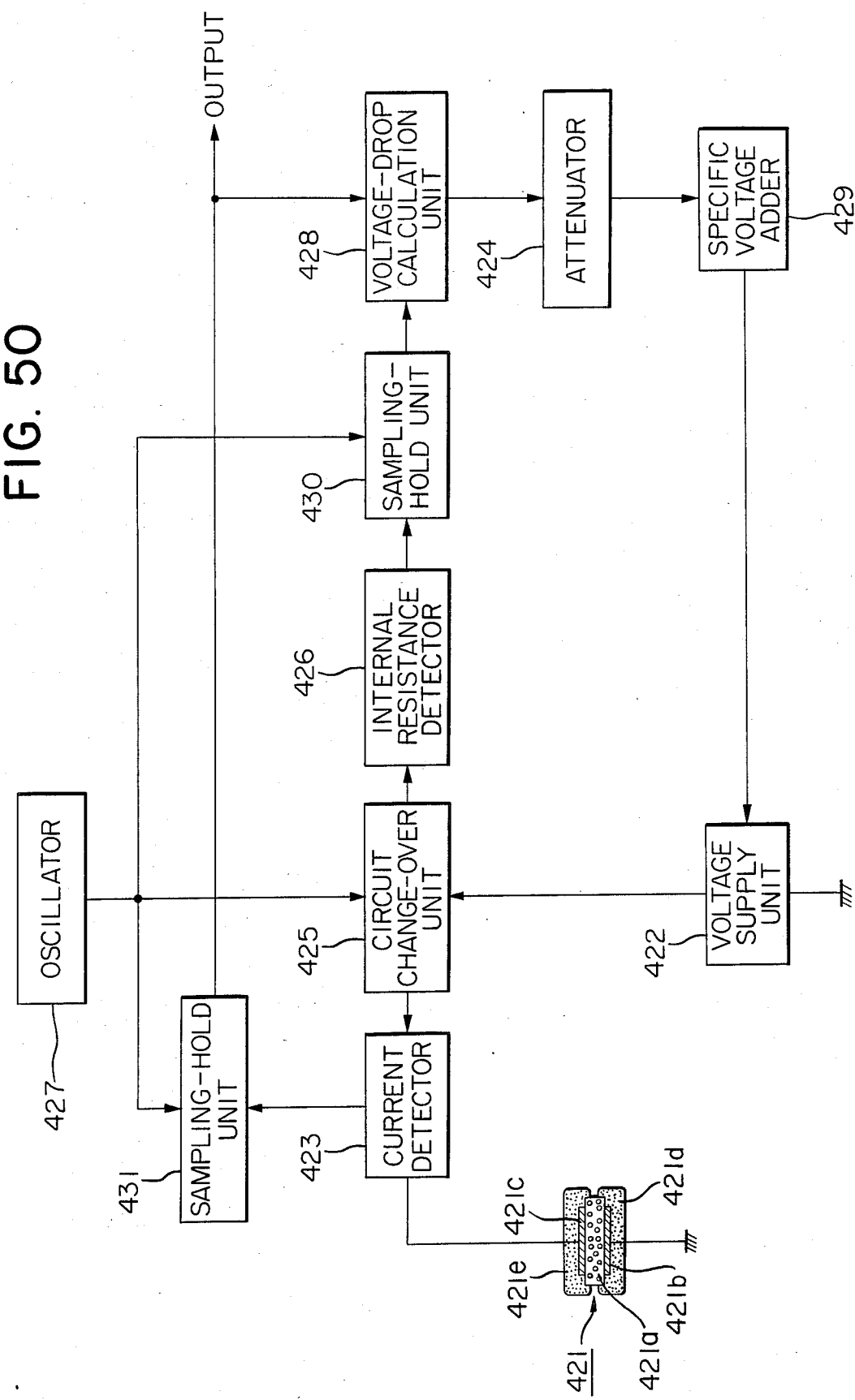
FIG. 50 is a block diagram of a limiting electric current type oxygen concentration detector in accordance with the seventh modification of the third embodiment of this invention wherein a limiting current type oxygen concentration sensor having two terminals is provided and a time shearing system is employed for allocation of time to the measurement of the internal resistance of the sensor and to the measurement of the limiting current of the sensor.

(b) Limiting current type oxygen concentration detectors provided with a sensor having 2 terminals and with a means for allocation of time to one period of measurement of the internal resistance and the other period for measurement of a limiting current, based on a time shearing system FIG. 50 shows a block diagram of a limiting current type oxygen concentration detector in accordance with the seventh modification of the third embodiment of this invention wherein a limiting current type oxygen concentration sensor having two terminals is provided and a time shearing system is employed for allocation of time to two periods of which one part is employed for measurement of the internal resistance of the sensor and the other part is employed for measurement of the limiting current flowing in the same sensor. Referring to the figure, a limiting electric current type oxygen concentration sensor 421 comprises an oxygen ionic conductor 421$a$, electrodes 421$b$ and 421$c$ placed on each surface of the oxygen ionic conductor 421$a$, a coating layer 421$e$ placed on one 421$c$ of the electrodes for the purpose to regulate the flow of oxygen which diffuses toward the electrode 421$c$, and a coating layer 421$d$ placed on the other 421$b$ of the electrodes for the purpose to protect the electrode 421$b$ for contamination.

In this circuitry, a time shearing system is employed. During one period, measurement is conducted for a limiting current flowing in the sensor 421. During the other period, measurement is conducted for the internal resistance of the sensor 421. A voltage supply unit 422 applies a voltage to the sensor 421 during the period for measurement of a limiting current. A current detector 423 detects the current which flows in the sensor 421 during the period for measurement of a limiting current.

A circuit change-over unit 425 changes over the circuitry for measurement of a limiting current flowing in and the internal resistance of the sensor 421.

An internal resistance detector 426 detects the internal resistance of the sensor 421.

An oscillator 427 functions to periodically change over the period for measurement of a limiting current and the period for measurement of the internal resistance. From the realistic viewpoints, a period range of 5 (msec) through 500 (msec) is preferable for each period. Since the rate in which the sensor changes its temperature is not necessarily quick, it is realistic that a longer time is allocated for measurement of a limiting current than for measurement of the internal resistance.

A voltage-drop calculation unit 428 multiplies the amounts of limiting current and the internal resistance to calculate the voltage-drop generated in the sensor.

A specific voltage adder 429 adds a portion of the voltage-drop generated in the internal resistance and a specific voltage (The amount of this voltage is required to be selected depending on the composition of a gas of which the oxygen concentration is measured, albeit a voltage range of 0.25 (V) through 1.0 (V) is realistic for exhaust gases of internal combustion engenes, such gases containing $CO_2$, $H_2O$ et al.), for the purpose to acquire a voltage suitable for measurement of a limiting current or a voltage which brings the operation point of a sensor to the excess voltage domination range.

A sampling-hold unit 430 holds or memorizes the amount of the internal resistance during the period for measurement of a limiting current wherein the measurement of the internal resistance is not conducted.

A sampling-hold unit 431 holds or memorizes the amount of a limiting current during the period for measurement of the internal resistance wherein the measurement of limiting current is not conducted.

The foregoing change-over action and the sampling action carried out by sampling hold units 430 and 431 synchronize to each other following the oscillator 427.

Following the clock signal generated by the oscillator 427, time is allocated to a first period and a second period each of which takes place periodically.

During the first period, a limiting current is measured. During this period, a sensor is applied a voltage of which the amount is the sum of a specific voltage and the amount of the voltage-drop caused by the internal resistance of a sensor, the voltage-drop having been measured in the previous period. As was described earlier, it is realistic to allocate a longer time for measurement of a limiting current of a sensor than for measurement of the internal resistance of a sensor.

During the second period, the internal resistance is measured. It is realistic to employ a direct-current voltage or an alternative-current voltage each of which has a marginal voltage (approximately 1 through 100 (mV)) for this purpose. A limiting current in the excess voltage domination range and the internal resistance are simultaneously measured, provided the first and second periods are repeated alternatively.

A move of the operating point in which a limiting current is measured, along the line $b_1$–$b_2$ shown in FIG. 49 following an increase in the oxygen concentration is equivalent to the behavior of a sensor which is provided with a fixed voltage power supply having a negative resistance ($r_3$), of which the amount is a product of the amount of the internal resistance $R_b$ (positive) of a sensor and the amount of the transfer rate of an attenuator 424. Namely, the amount of the negative resistance $r_3$ is represented by $$r_3 = -R_b \times \eta \quad (27)$$

wherein, $\eta$ represents the transfer rate of an attenuator.

It is well-known that the negative resistance must be compensated by means of series addition of an ordinary resistance of which the amount is larger than that of the negative resistance in order to prohibit oscillation from occurring and to allow stable operation for the circuit. As a result, what is requested is:

$$R_b + r_3 > 0 \quad (28)$$

Therefore, $$\eta < 1 \quad (29)$$

Referring to FIG. 49, the foregoing requirement is equivalent to that the incline of the line $c_1$–$c_2$ which represents the current vs. voltage characteristics of the internal resistance $R_b$ of a sensor must be less than the incline of the line $b_1$–$b_2$ along which the operating point of the sensor moves following a variation of the oxygen concentration.

The internal resistance compensation in accordance with this invention has an effect to expand the oxygen concentration range in which measurement is allowed for the oxygen concentration, by a ratio $1/(1+\eta)$. Albeit this means that the amount of $\eta$ close to 1 causes the ratio to become unlimitedly higher, a range of 0.5 through 0.99 is realistic particularly because of the problem of stability.

The attenuator 424 can be arranged at any point selected from the points between the internal resistance calculation unit 426 and the sampling-hold unit 430, between the sampling-hold unit 430 and the voltage drop calculation unit 428, and between the specific voltage adder 429 and the voltage supply unit 422. These selections of points at which the attenuator 424 is arranged caused no functional difference for the oxygen concentration detector. Further, adjustment of one or more proportional constants of calculation units 426, 430, 428, 429 and 422 causes elimination of the attenuator 424.

In addition, three selections are allowed for points at which the sampling-hold unit 430 is arranged. The points can be selected from between the voltage-drop calculation unit 428 and the attenuator 424, between the attenuator 424 and the specific voltage adder 429 or between the specific voltage adder 429 and the voltage supply unit 422. These selections cause no functional change.

Figure 51:
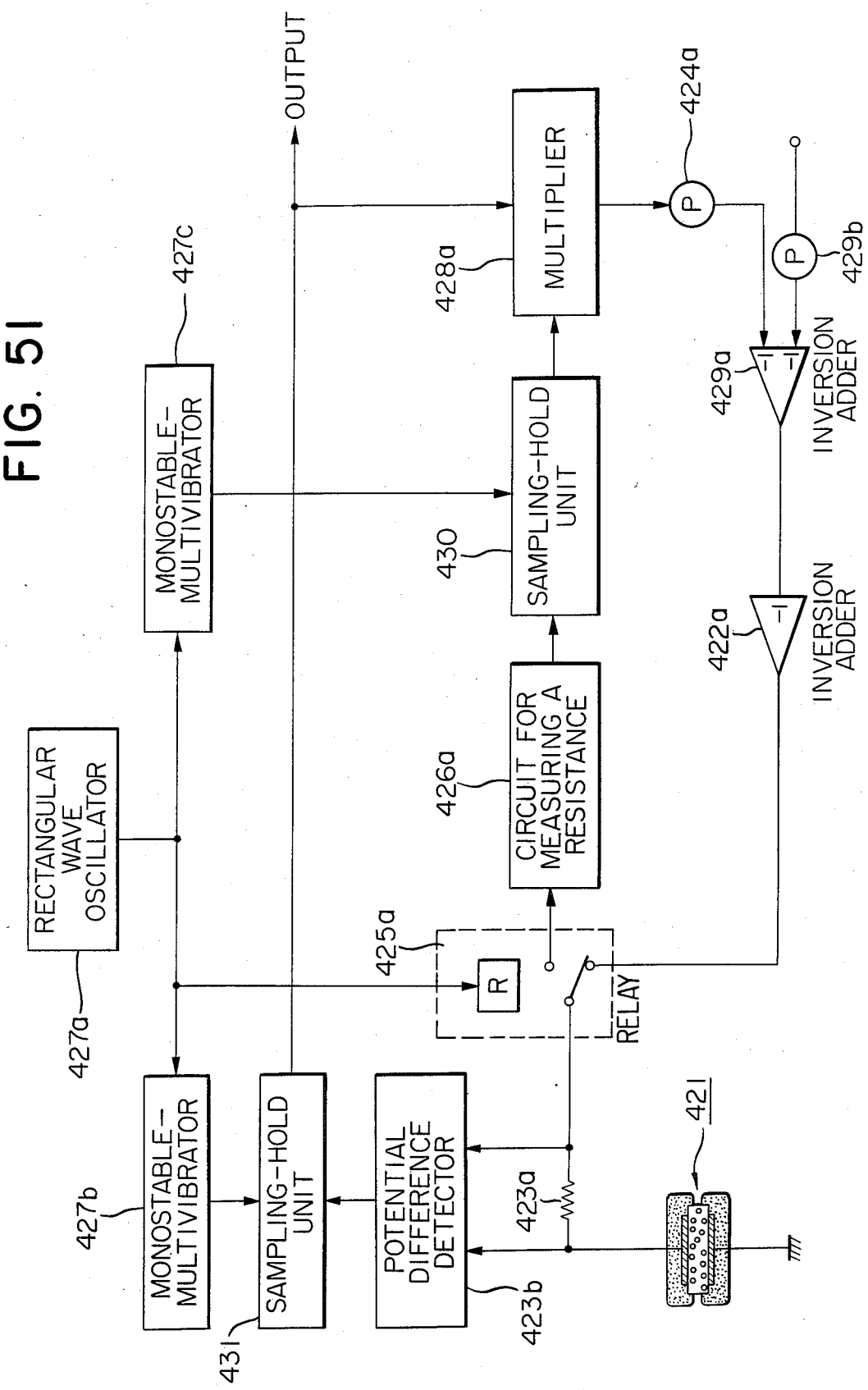
FIG. 51 is a block diagram of a limiting electric current type oxygen concentration detector in accordance with the eighth modification of the third embodiment of this invention wherein a limiting current type oxygen concentration sensor having two terminals is provided and a time shearing system is employed for allocation of time to the measurement of the internal resistance of the sensor and to the measurement of the limiting current of the sensor.

FIG. 51 shows a block diagram of a limiting current type oxygen concentration detector in accordance with the eighth modification of the third embodiment of this invention, which is based on the same idea as for the modification of which the block diagram is shown in FIG. 50. Referring to the figure, an inversion adder 422a applies a voltage to a sensor during the period in which measurement is conducted for a limiting current of the sensor. A voltage appearing across a resistance of 423a to represent a limiting current is detected by an electric potential detector 423b. A potentiometer 424a provides a signal representing the ratio with which a voltage-drop is compensated.

A relay 425a functions to alternately connect the sensor with a circuit for measurement of a limiting current and with a circuit for measurement of the internal resistance.

A circuit 426a is employed for measurement of a resistance by means of application of a marginal amount of voltage.

A rectangular wave oscillator 427a generates a clock signal which regulates allocation of time to the first period in which a limiting current is measured and to the second period in which the internal resistance is measured. Monostable-multivibrator 427b functions to delay measurement of a limiting current for a short period for the purpose to avoid an adverse effect due to the transient phenomena. A monostable-multivibrator 427e performs a similar function for sampling of the internal resistance.

A multiplier 428a calculates a voltage-drop generated in the sensor by multiplying the amounts of limiting current and the internal resistance. An inversion adder 429a adds a specific voltage provided by a potentiometer 429b to the voltage-drop. Function of sampling-hold units 430 and 431 is to avoid adverse effects caused by transient phenomena which occur immediately after change-over of the periods.

Figure 52:
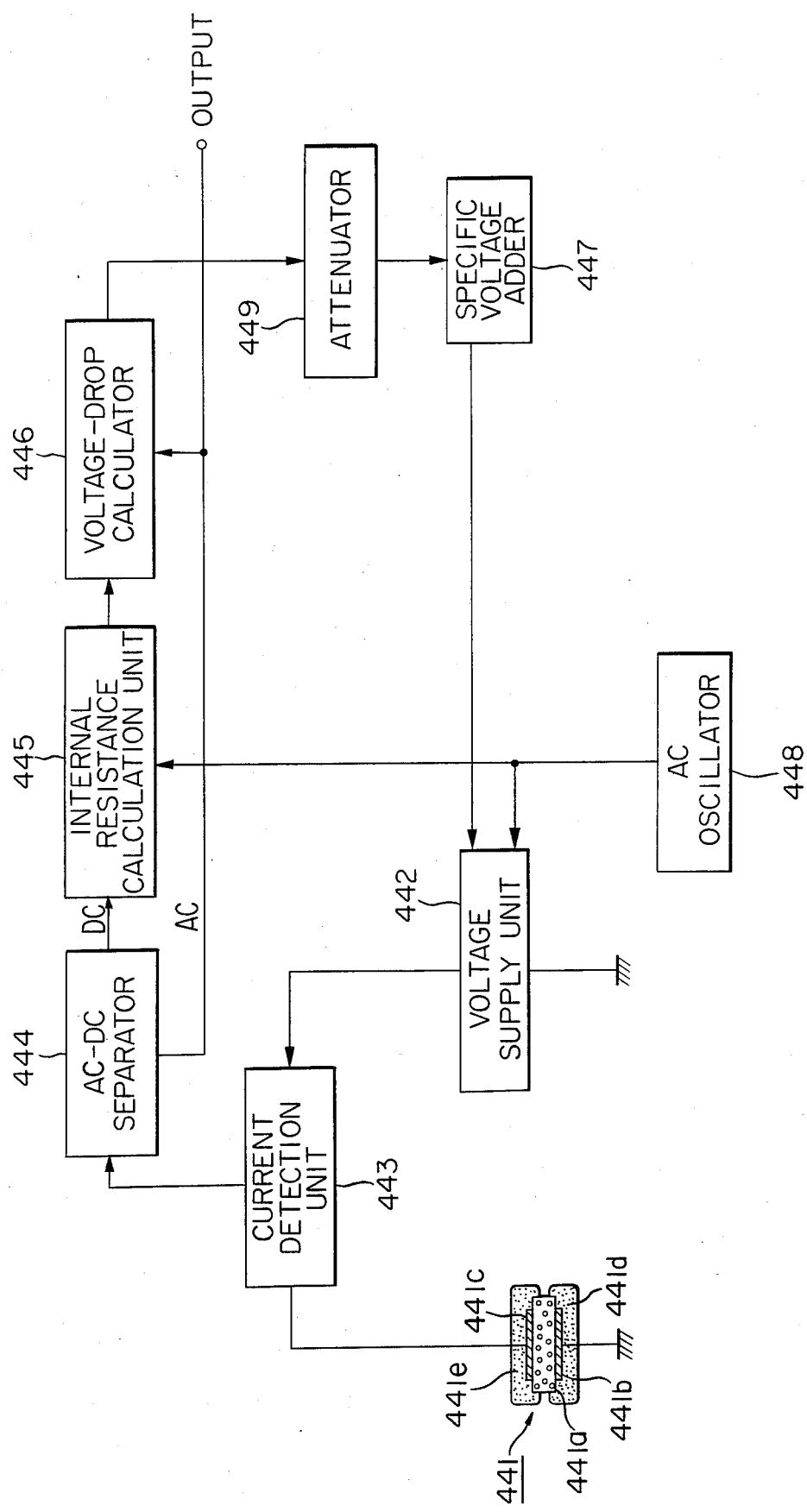
FIG. 52 is a block diagram showing the fundamental construction of a limiting current type oxygen concentration detector in accordance with the ninth modification of the third embodiment of this invention wherein a limiting current type oxygen concentration sensor having two terminals is provided and direct current is employed for measuring the internal resistance of the sensor and alternative current is employed for measuring the limiting current of the sensor.

(c) Limiting current type oxygen concentration detectors provided with a sensor having 2 terminals and in which alternative current is employed for measurement of the internal resistance of the sensor and direct current is employed for measurement of a limiting current flowing in the sensor FIG. 52 shows a block diagram showing the fundamental construction of limiting current type oxygen concentration detection wherein a sensor having two terminals is provided and direct current is employed for measurement of the internal resistance of the sensor and alternative current is employed for measurement of a limiting current flowing in the sensor. Referring to the figure, a limiting electric current type oxygen concentration sensor 441 comprises an oxygen ionic conductor 441a, electrodes 441b and 441c placed on each surface of the oxygen ionic conductor 441a, a coating layer 441e placed on one of the electrodes 441e for the purpose to regulate the flow of oxygen which diffuses toward the electrode 441c, and a coating layer 441d placed on the other of the electrodes 441b for the purpose to protect the electrode 441b from contamination. A voltage supplier 442 applies a voltage to the sensor 441 through a current detector 443. A current signal picked up by the current detector 443 is applied to an alternative current direct current separator 444, which outputs a direct current component which represents the limiting current further representing the oxygen concentration, and which outputs an alternative current component which is applied to an internal resistance calculation unit 445. An alternative current oscillator 448 applies a voltage to the internal resistance calculation unit 445 to allow the unit 445 to calculate the internal resistance of the sensor employing the voltage and the alternative current component applied by the separator 444. A voltage-drop calculator 446 multiplies the amount of the internal resistance to the direct current component which represents the limiting current to calculate the voltage-drop ($V_1$ shown in FIG. 49) generated in the internal resistance. A portion of the amount of the voltage-drop is added to the amount of a specific voltage ($\Delta V$ shown in FIG. 49) in a specific voltage adder 447. This is the direct-current voltage ($V_2$ shown in FIG. 49) which is applied to the sensor. The output voltages of the specific voltage adder 447 and the alternative current oscillator 448 are added in the voltage supply unit 442.

FIG. 49 describes that the operating point of a sensor at which the measurement of a limiting current is allowed, moves along the line $b_1$-$b_2$ following a variation of the oxygen concentration. This is a phenomenon equivalent to that inherent to a circuit consisting of a sensor and a fixed voltage power supply which exhibits a negative resistance, of which the amount ($r_3$) is shown by $$r_3 = -Rb \times \eta \tag{30}$$

wherein,
  Rb represents the amount of the internal resistance of a sensor, and
  $\eta$ represents the attenuation ratio of the attenuator 449.

In order to allow a stable operation which is free of oscillation for such a circuit as exhibits a negative resistance, the negative resistance must be compensated by a positive resistance of which the amount is larger than the negative resistance. As a result, what is required is:

$$Rb + r_3 > 0 \tag{31}$$

Therefore, $$\eta < 1 \tag{32}$$

Referring to FIG. 49, the foregoing requirement is equivalent to that the incline of the line $C_1$-$C_2$ which represents the current vs. voltage characteristics of the internal resistance Rb of a sensor must be less than the incline of the line $b_1$-$b_2$ along which the operating point of the sensor moves following a variation of the oxygen concentration.

The internal resistance compensation in accordance with this invention has an effect to expand the oxygen concentration range in which measurement is allowed for the oxygen concentration, by a ratio $1/(1+\eta)$. Albeit this means that the amount of $\eta$ close to 1 causes the ratio to become unlimitedly highly, a range of 0.5 through 0.99 is realistic particularly because of the problem of stability.

The attenuator 449 can be arranged at any point selected from the points between the internal resistance calculation unit 445 and the voltage-drop calculator 446, between the alternative-current direct current separator 444 and the voltage-drop calculator 446, and between the specific voltage adder 447 and the voltage supply unit 442. These selections of points at which the attenuator 449 is arranged cause no functional difference for the oxygen concentration detector. Further, adjustment of one or more proportional constants of calculation units 444, 445, 446 and 447 causes elimination of the attenuator 449.

Figure 53:
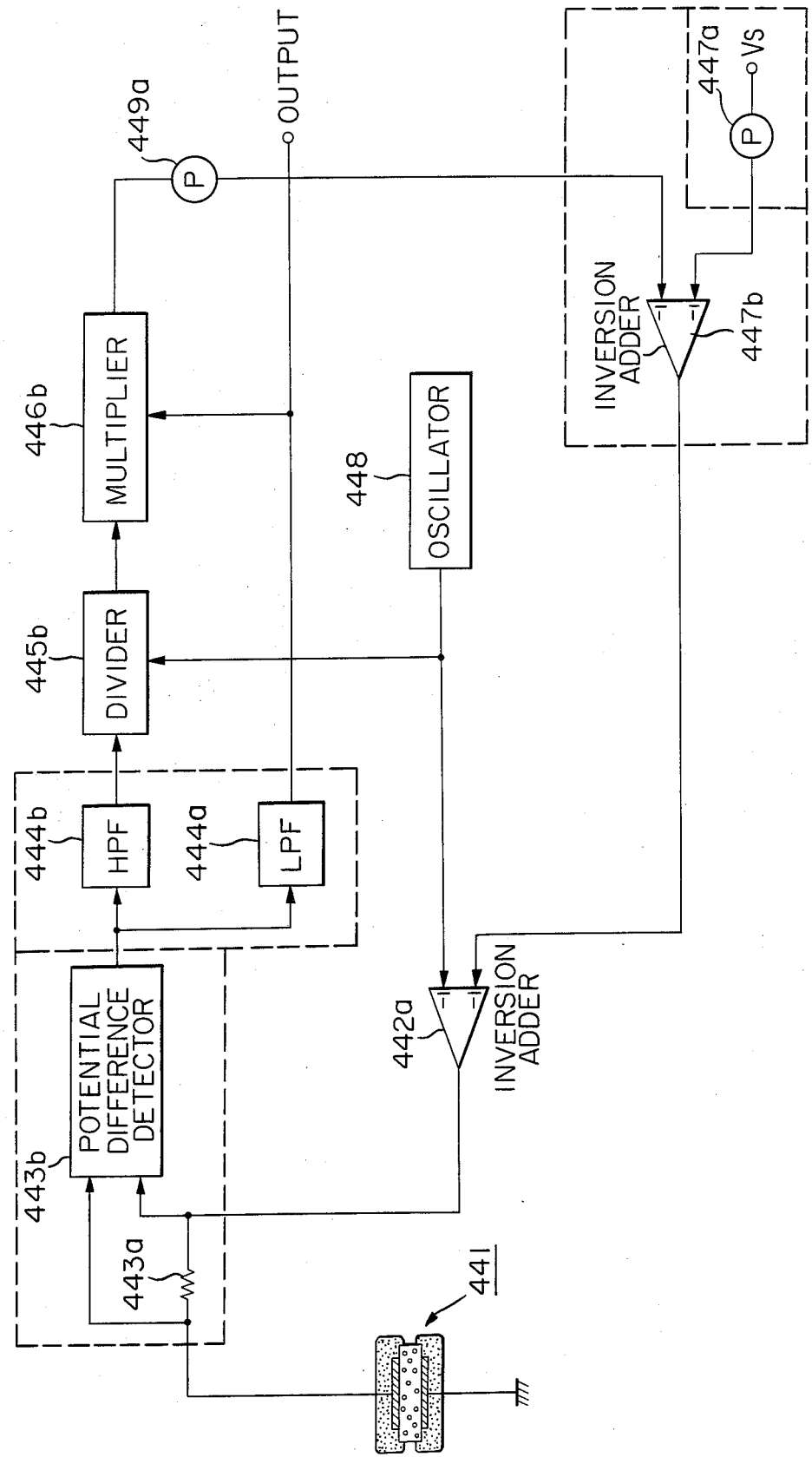
FIG. 53 is a block diagram showing a limiting electric current type oxygen concentration detector in accordance with one alteration of the ninth modification of the third embodiment of this invention of which the fundamental construction is shown in FIG. 52.

FIG. 53 shows a block diagram of a limiting current type oxygen concentration detector in accordance with one alteration of the detector shown in FIG. 52. Referring to the figure, an inversion adder 442a applies a voltage to a sensor 441 through a resistor 443a which has a function to detect the current flowing in the sensor 441. A potential difference detector 443b determines the amount of a current employing a combination of the amount of the resistance 43a and the amount of the potential difference of 43b based on the following formula.

$$I = V/R \tag{33}$$

wherein,
  I represents the intensity of a current,
  V represents the amount of the potential difference, and
  R represents a resistance.

A high pass filter (HPF) 444b picks up the alternative-current component out of the output of the potential difference detector 443b. This can be replaced by a band filter, a lock-in amplifier or a tracking filter et al. A low pass filter (LPF) 444a picks up the direct-current component out of the output of the potential difference detector 443b. This direct-current component represents a limiting current of the sensor 441. An oscillator 448 generates an alternative-current voltage. The frequency range and the voltage range preferable for measurement of the internal resistance are respectively 0.5 through 100 (KHz) and 1 through 500 (mV). A divider 445b conducts the following calculation to acquire the internal resistance of the sensor, after being applied the outputs of the high pass filter 444b and the oscillator 448.

$$r_1 = E_{AC}/I_{AC} \tag{34}$$

wherein, $r_1$ represents the internal resistance of the sensor containing the surface resistance thereof, $E_{AC}$ represents the output voltage of the oscillator, and $I_{AC}$ represents the output of the high pass filter.

The output of the divider 445b which represents the internal resistance of the sensor 441 and the output of the low pass filter 444a which represents a limiting current of the sensor 441 are applied to a multiplier 446b which conducts the following calculation to acquire the voltage-drop generated in the internal resistance.

$$V_d = I_{dc} \times r_1 \tag{35}$$

wherein, $V_d$ represents the voltage-drop generated in the internal resistance, and $I_{dc}$ represents the output of the low pass filter which represents the limiting current of the sensor.

A specific voltage of which the amount is approximately 0.5 (V) is produced in a potentiometer 447a which is applied a reference voltage of which the amount is approximately −10 (V). The specific voltage is added to a portion of the output of the multiplier 446b (the output of a potentiometer 449a which is applied the output of the multiplier 446b) in an inversion adder 447b. The output of this inversion adder 447b is the direct-current voltage component of the voltage which is applied to the sensor 441. This direct-current voltage component is added to the alternative-current voltage component which is the output voltage of the oscillator 448, to produce a voltage which is applied to the sensor for the purpose to carry out the measurement of the oxygen concentration.

Figure 54:
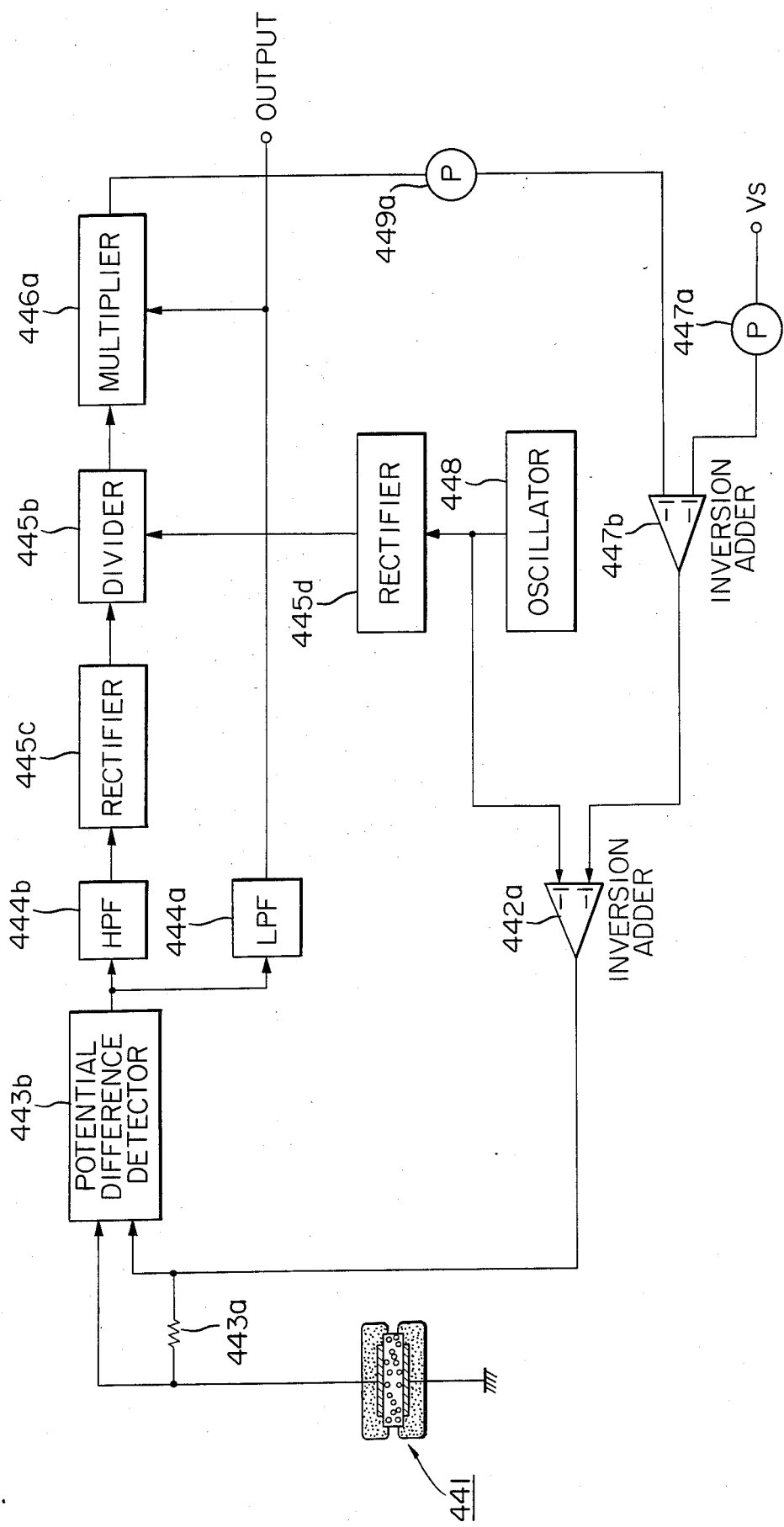
FIG. 54 is a block diagram showing a limiting electric current type oxygen concentration detector in accordance with another alteration of the ninth modification of the third embodiment of this invention of which the fundamental construction is shown in FIG. 52.

FIG. 54 shows a block diagram of a limiting current type oxygen concentration detector in accordance with another alteration of the device shown in FIG. 52. This has an advantage in which the outputs of the high pass filter 444b and the oscillator 448 are rectified, before being applied to the divider 445b, so that a possibility in which some number is divided by zero is removed, resultantly solving a problem of a potential unstable operation in a range wherein the amount of alternative current is close to zero.

It is of course possible that a multiplication and/or division can be replaced by an addition and/or a subtraction to be conducted for the numerals converted to logarithmic numbers, before the sum and/or the difference shown in logarithmic numbers are or is converted back to the ordinary numbers.

FIGS. 55 through 58 demonstrate the effects of this invention by means of comparison of various items of characteristics of limiting current type oxygen concentration detectors in accordance with this invention which are shown in full lines and of limiting current type oxygen concentration detectors available in the prior art which are shown in broken lines.

Figure 55:
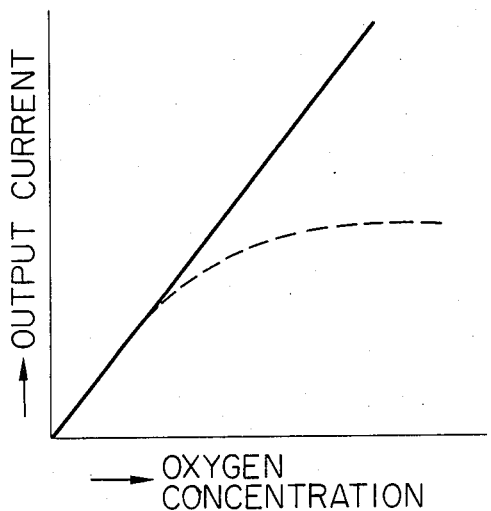
FIG. 55 is a graph comparing the characteristics of the output current vs. oxygen concentration relations of limiting current type oxygen concentration detectors in accordance with this invention and available in the prior art.

FIG. 55 compares the characteristics of the output current vs. oxygen concentration relations. Referring to the figure, the limiting current type oxygen concentration detectors available in the prior art show a tendency in which the current vs. oxygen concentration relations saturate in a higher oxygen concentration range, due to an increase in the internal resistance which inevitably occurs in a higher oxygen concentration range. In the case of the limiting current type oxygen concentration detectors in accordance with this invention, since the increase in the voltage drop generated in the internal resistance of a sensor is compensated, the current vs. oxygen concentration relations maintains a good linearity for a wide range of the oxygen concentration, resulting in a better accuracy and a wider oxygen concentration range in which the measurement of the oxygen concentration is allowed.

Figure 56:
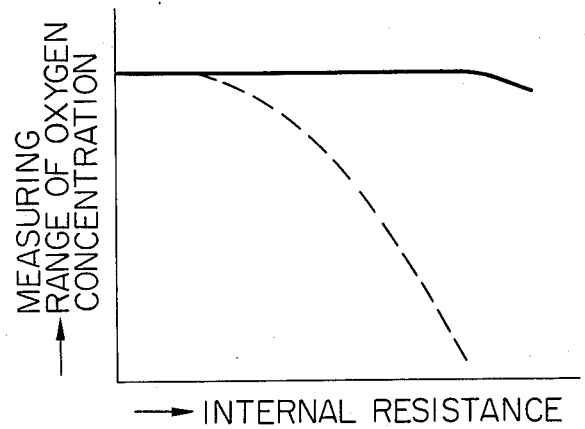
FIG. 56 is a graph comparing the characteristics of the oxygen concentration range in which the measurement is allowed vs. the internal resistance of a sensor, of limiting current type oxygen concentration detectors in accordance with this invention and available in the prior art.
Figure 57:
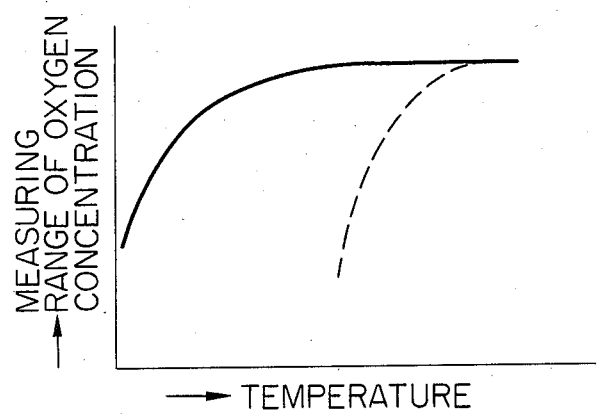
FIG. 57 is a graph comparing the oxygen concentration measurement range vs. temperature characteristics of limiting current type oxygen concentration detectors in accordance with this invention and available in the prior art.

FIG. 56 compares the characteristics of the oxygen concentration range in which the measurement is allowed vs. the internal resistance of a sensor. Referring to the figure, the detectors available in the prior art vary the oxygen concentration range in which the measurement is allowed, depending on the amount of the internal resistance. In the case of the detectors in accordance with this invention, however, measurement is allowed for a wide range of oxygen concentration, regardless of the amount of the internal resistance of a sensor, because the influence of FIG. 57 compares the relations between the oxygen concentration range in which the measurement is allowed and the temperature. Referring to the figure, the detectors available in the prior art decreases the oxygen concentration range in which the measurement is allowed, following a decrease in the temperature. In the case of the detectors in accordance with this invention, however, a relatively wide range is maintained for measurement of the oxygen concentration is maintained, regardless of a variation in temperature. This is again because the influence of the internal resistance of a sensor which is under the influence of temperature is well compensated.

Figure 58:
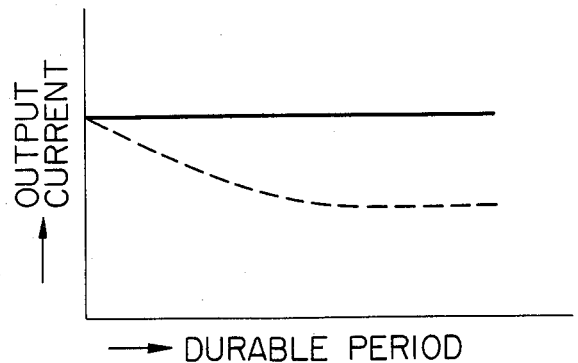
FIG. 58 is a graph comparing the output current vs. utilization period characteristics of limiting current type oxygen concentration detectors in accordance with this invention and available in the prior art.

FIG. 58 compares the output current vs. utilization period characteristics. Referring to the figure, the detectors available in the prior art decreases the output current following the increase in utilization period. This is because the amount of the internal resistance of a sensor is inherently inclined to vary during the initial period of utilization. In the case of the detectors in accordance with this invention, however, since the influence of variation of the internal resistance is compensated, no such a tendency is observed, albeit the foregoing inherent nature would remain unchanged for a sensor.

The foregoing description has clarified that the limiting electric current type oxygen concentration sensor in accordance with this invention is applied an improvement wherein the influence of the voltage-drop generated in the internal resistance of a limiting current type oxygen concentration sensor which is inherently under the influence of temperature, is removed, resultantly realizing various items of advantages including (a) an improved accuracy in measurement of the oxygen concentration, (b) an expanded range of the oxygen concentration and the temperature wherein the measurement is allowed for the oxygen concentration, (c) removal of adverse effects caused by variation of the amount of the internal resistance which is predominantly due to deterioration which happens following the utilization thereof.

LIMITING ELECTRIC CURRENT TYPE OXYGEN CONCENTRATION DETECTOR IN ACCORDANCE WITH OTHER OR COMBINED EMBODIMENTS OF THIS INVENTION

This invention is not limited to the foregoing embodiments. Particularly, combination of the foregoing embodiments, modifications and/or alterations, realizes various combined advantages of this invention, resulting in further improvements of the performance and in diversification of the employment thereof.

Figure 59:
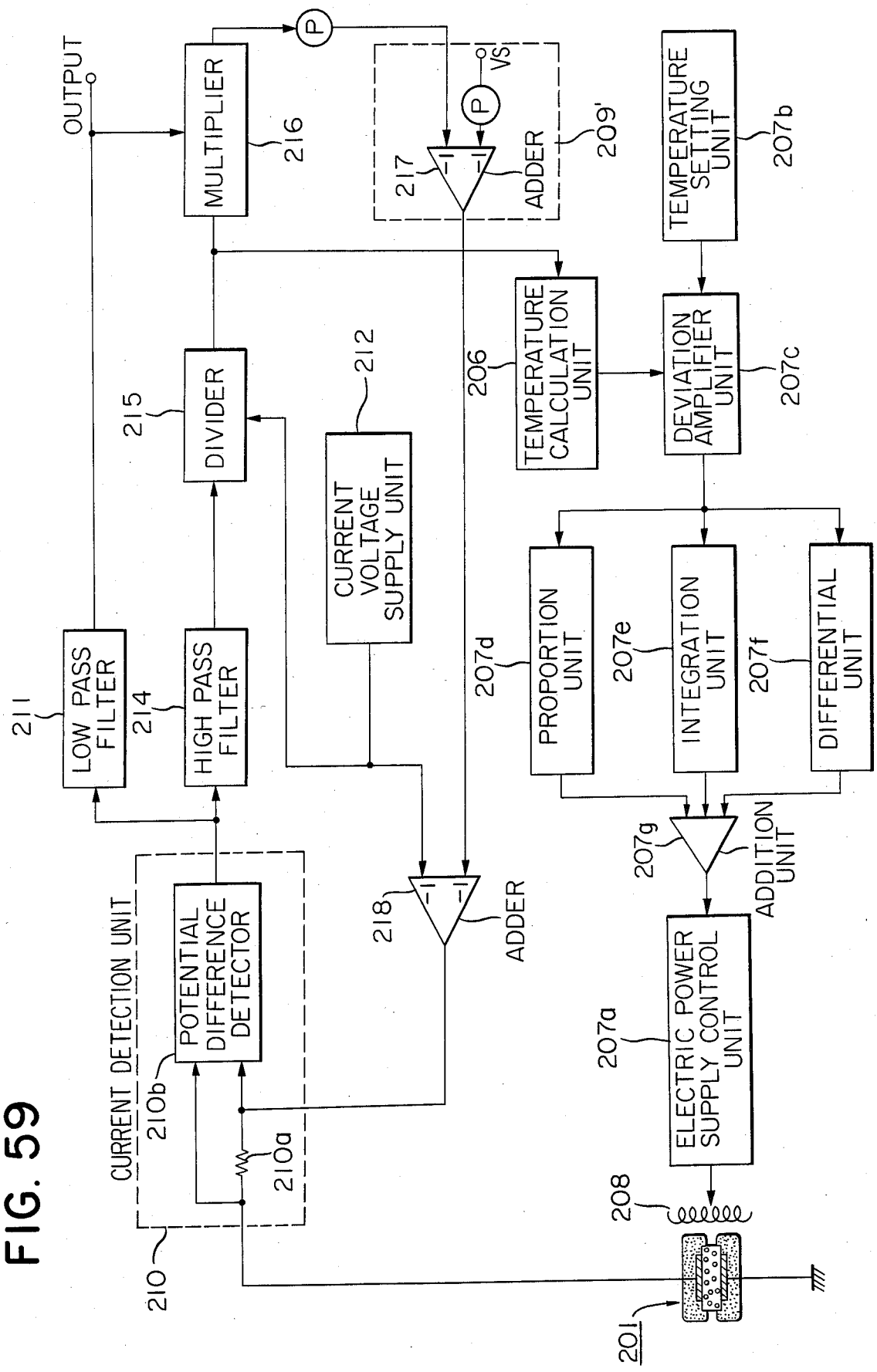
FIG. 59 is a block diagram of a limiting electric current type oxygen concentration detector in accordance with a combined modification of the first and third embodiments of this invention.

FIG. 59 shows a block diagram of a limiting current type oxygen concentration detector in accordance with a combined modification of the first and third embodiments of this invention, wherein the temperature of the sensor is regulated to stay at a predetermined amount, following the amount of the internal resistance which is measured in the detector and also wherein the amount of voltage which is employed for measurement of a limiting current flowing in the sensor is regulated to stay in the excess voltage range, also following the amount of the internal resistance. Referring to FIG. 59, the components of which the function is identical to that of the corresponding components shown in FIG. 31 are given the same indices as were given to such corresponding components. The major differences in comparison with what is shown in FIG. 31 are that this limiting current type oxygen concentration detector is based on an idea that (a) the amount of the voltage-drop generated in the internal resistance of a sensor 201 is calculated in a multiplier 216, (b) the amount of the voltage-drop and a predetermined amount of voltage are added in an adder 217 to apply correction thereto and to produce an amount of direct-current voltage which is employed for measurement of the oxygen concentration. An adder 218 is employed for superposing the direct-current voltage to an alternative-current voltage, before it is applied to the sensor 201. As was described in the description presented with reference to FIG. 13, it is possible to compile a temperature calculation units employing either 206b through 206f shown in FIG. 28, or 206c through 206m shown in FIG. 29, or 206c through 206f shown in FIG. 30.

Albeit the invention has been described with reference to specific embodiments, modifications and/or alterations, this description is not meant to be construed in a limiting sense. Various other embodiments, modifications and/or alterations of this invention will become apparent to persons skilled in the art upon reference to the description of this invention. It is therefore contemplated that the appended claims will cover any such embodiments, modifications and/or alterations as fall within the true scope of this invention.

What is claimed is:

1. A limiting electric current oxygen concentration detector comprising:
    (a) a limiting electric current oxygen concentration sensor, said sensor including an oxygen ionic conductor having major surfaces, a cathode on one of said surfaces, an anode on another of said surfaces, and means for controlling the rate of oxygen permeation into said oxygen ionic conductor,
    (b) means for measuring a limiting electric current which flows in said limiting electric current type oxygen concentration sensor responsive to the application of a voltage to said sensor,
    (c) means for measurng the internal resistance of said sensor by application of a voltage of an amount large enough to cause said sensor to operate in the resistance domination range,
    (d) means for allocating time to a first period in which said means for measuring the limiting current of said sensor is caused to function and to a second period in which said means for measuring the internal resistance of said sensor is caused to function,
    (e) means for calculating a voltage-drop generated in the internal resistance of said sensor, employing the amount of the internal resistance and the limiting current as measured by their respective means,
    (f) a first attenuator for attenuating the output of said means for calculating the voltage-drop by a ratio, thereby preventing oscillation of a circuit driving said sensor, and
    (g) means for generating a voltage which is employed for measurement of a limiting current of said sensor, by addition of of a specific voltage and the output voltage of the first attenuator.

2. A limiting electric current oxygen concentration detector as defined in claim 1, wherein
    said means for allocating time to a first period and to a second time comprises
        a control signal generator for alternately generating a control signal representing the first period and a control signal representing the second period,
        circuit change-over means for connecting said means for measuring the internal resistance to said sensor by the control signal representing the first period and connecting said means for measuring the limiting electric current to said sensor by the control signal representing the second period,
        first sampling-hold means for sampling-holding the output from said means for measuring the internal resistance by the control signal representing the first period, and
        second sampling-hold means for sampling-holding an output from said means for measuring the limiting electric current by the control signal representing the second period,
    said means for calculating the voltage-drop comprises multiplying means for multiplying the outputs from said first and second sampling-hold means, and
    said means for generating a voltage for measurement of a limiting current comprises
        a voltage source for generating a voltage,
        a second attenuator for attenuating the voltage generated by said voltage source and generating the specific voltage, and
        an adder for adding the output from said first attenuator and the output from said second attenuator.

3. A limiting electric current oxygen concentration detector comprising:
    (a) means including a limiting electric current oxygen concentration sensor, said sensor including an oxygen ionic conductor having major surfaces, a cathode on one of said surfaces, an anode on another of said surfaces, and means for controlling the rate of oxygen permeation into said oxygen ionic conductor, (b) means for applying a voltage containing alternating voltage and direct voltage superposed on each other for supplying a current containing alternating current and direct current superposed on each other to said sensor, (c) means for independently picking up the alternating-current component and the direct-current component from the output voltage of said sensor, whereby the amount of limiting current flowing in said sensor is acquired from said direct-current component and the magnitude of the internal resistance of said sensor is acquired from said alternating-current component, (d) means for calculating a temperature correction coefficient from the formula $$\alpha(T) = (T/T_o)^{-m}$$

wherein,
T represents absolute temperature
To represents reference temperature based on said magnitude of the internal resistance of said sensor, and (e) means for applying temperature correction to said amount of limiting current flowing in said manner, employing said temperature correction coefficient α(T).

4. A limiting electric current oxygen concentration detector as defined in claim 3, wherein the formula for the temperature correction coefficient α(T) is approximated as follows:

$$\alpha(T) = 1 + 2m(KT_o/E)\{(R-R_o)/(R+R_o)\}$$

wherein
E represents activation energy,
K represents Boltzmann constant,
T represents absolute temperature,
To represents reference temperature,
R represents internal resistance, and
Ro represents internal resistance at the temperature To.

5. A limiting electric current oxygen concentration detector as defined in claim 3, wherein the formula for the temperature correction coefficient (T) is approximated as follows:

$$\alpha(T) = 1 + m(KT_o/E)\{(R/R_o) - 1\}$$

wherein
E represents activation energy,
K represents Boltzmann constant
T represents absolute temperature,
To represents reference temperature,
R represents internal resistance, and
Ro represents internal resistance at the temperature To.

6. A limiting electric current oxygen concentration detector as defined in claim 3 wherein said formula for the temperature T is approximated as follows:

$$T = \frac{1}{(K/E)(R/R_o - 1) + 1/T_o}$$

wherein,

E represents activation energy
K represents Boltzmann constant
R represents internal resistance
Ro represents internal resistance at the temperature To.

7. A limiting electric current oxygen concentration detector comprising:

(a) means including a limiting electric current oxygen concentration sensor, said sensor including a oxygen ionic conductor having major surfaces, a cathode on one of said surfaces, an anode on the other of said surfaces, and means for controlling the rate of oxygen permeation into said oxygen ionic conductor, (b) means for measuring a voltage-drop (V₁) generated in the internal resistance of said sensor, and (c) means for measuring a limiting electric current flow in said sensor in response to a voltage of an amount equal to the sum (V₁+ΔV) of a specific voltage (ΔV) and said voltage-drop (V₁).

8. A limiting electric current oxygen concentration detector comprising (a) means including a limiting electric current oxygen concentration sensor, said sensor including an oxygen ionic conductor having major surfaces, a cathode on one of said surfaces, an anode on the other of said surfaces, means for controlling the rate of oxygen permeation into said oxygen ionic conductor, and means for heating said sensor, (b) a direct current voltage source for generating a direct voltage to be superposed on an alternating voltage and applied to said sensor in order to measure a limiting electric current flowing therein, (c) an alternating current voltage source for generating alternating voltage to be applied to said sensor in order to measure internal resistance thereof, (d) current detection means for detecting the current flowing in said sensor by applying a voltage obtained by superposing the alternating and direct voltages on said sensor, (e) alternating- and direct-current component separating means for separating an alternating-current component from a direct-current component from the output of said current detection means, (f) means for determining the internal resistance of said sensor in accordance with the output from said alternating voltage source and the alternating-current output component from said alternating- direct-current component separating means, (g) means for calculating the internal resistance of said sensor according to the following formula, $$T = 1/\{K/E) \log_e (R/R_o) + 1/T_o\}$$

wherein,
e represents the base of natural logarithms,
E represents activation energy,
K represents Boltzmann constant,
T represents absolute temperature,
To represents reference temperature
R represents internal resistance,
Ro represents internal resistance at the temperature To, (h) means for determining the temperature T according to the output of said means for calculating the internal resistance (i) means for setting a temperature, and (j) means for controlling current from a power source to said means for heating said sensor according to the difference between said calculated value of temperature of said sensor and the set temperature.

9. A limiting electric current oxygen concentration detector as defined in claim 8, wherein said formula for the temperature T is approximated as follows:

$$T = 1/[2(K/E)\{(R/R_o - 1)/(R/R_o + 1)\} + 1/T_o].$$

10. A limiting electric current oxygen concentration detector as defined in claim 8, wherein said formula for the temperature T is approximated as follows:

$$T = 1/[(K/E)(R/R_o - 1) + 1/T_o].$$

11. A limiting electric current oxygen concentration detector comprising:
   (a) means including a limiting electric current oxygen concentration sensor, said sensor including an oxygen ionic conductor having major surfaces, a cathode on one of said surfaces, an anode on the other of said surfaces, means for controlling the rate of oxygen permeation into said oxygen ionic conductor, and means for heating said sensor,
   (b) a first voltage source for generating a voltage to be applied to said sensor during a first period so as to measure a limiting electric current flowing thereto,
   (c) a second voltage source for generating a voltage to be applied to said sensor during a second period so as to measure internal resistance thereof,
   (d) means for performing control in a time-sharing manner such that the voltage from said first voltage source is supplied to said sensor during a first period and the voltage from said second voltage source is supplied to said sensor during a second period,
   (e) current detection means for detecting the current flowing when the voltage from said first voltage source is applied to said sensor and the current flowing when the voltage from said second voltage source is applied to said sensor,
   (f) means for determining the internal resistance of said sensor in accordance with the detected current from said current detection means,
   (g) means for calculating the internal resistance of said sensor according to the following formula, $$T = 1/\{(K/E) \log_e (R/R_o) + 1/T_o\}$$

wherein,
   e represents the base of natural logarithms,
   E represents activation energy
   K represents Boltzmann constant,
   T represents absolute temperature
   To represents reference temperature
   R represents internal resistance,
   Ro represents internal resistance at the temperature To,
   (h) means for determining the temperature T according to the output of said means for calculating the internal resistance,
   (i) means for setting a temperature, and
   (j) means for controlling current from a power source to said means for heating of said sensor according to the difference between said calculated value of temperature of said sensor and the set temperature.

12. A limiting electric current oxygen concentration detector defined in claim 11 wherein said formula for the temperature T is approximated as follows:

$$T = \frac{1}{(2(K/E)\{(R/R_o - 1)/(R/R_o + 1)\} + 1/T_o)}.$$

13. A limiting electric current oxygen concentration detector comprising:
   (a) means including a limiting electric current oxygen concentration sensor, said sensor including (i) a first component which detects a limiting electric current of said sensor, said component comprising a cathode layer placed on one surface of an oxygen ionic conductor and an anode layer placed on the other surface of said oxygen ionic conductor, and (ii) a second component which detects the internal resistance of said sensor, said second component comprising at least an additional electrode placed on the surfaces of said oxygen ionic conductor means for controlling the rate of oxygen permeation into said oxygen ionic conductor, and means for heating said sensor,
   (b) means for measuring the internal resistance of said limiting electric current type oxygen concentration sensor,
   (c) means for determining the temperature according to the output of said means for measuring the internal resistance of said sensor according to the following formula, $$T = 1/\{(K/E) \log_3 (R/R_o) + 1/T_o\}$$

wherein,
   e represents the base of natural logarithms,
   E represents activation energy,
   K represents Boltzmann constant,
   T represents absolute temperature,
   To represents reference temperature
   R represents internal resistance,
   Ro represents internal resistance at the temperature of To,
   (d) means for setting a temperature,
   (e) means for controlling current from a power source to said means for heating of said sensor according to the difference between said calculated value of temperature of said sensor and the set temperature, and
   (f) means for measuring the limiting electric current which flows in said first component.

14. A limiting electric current oxygen concentration detector as defined in claim 13, wherein said formula for the temperature T is approximated as follows:

$$T = 1/[2(K/E)\{(R/R_o - 1)/(R/R_o + 1)\} + 1/T_o].$$

15. A limiting electric current oxygen concentration detector as defined in claim 13, wherein said formula for the temperature T is approximated as follows:

$$T = 1/[(K/E)(R/R_o - 1) + 1/T_o].$$

16. A limiting electric current oxygen concentration detector comprising:
   (a) means including a limiting electric current oxygen concentration sensor, said sensor including (i) a first component which detects a limiting electric current of said sensor, said component comprising a cathode layer placed on one surface of an oxygen ionic conductor and an anode layer placed on the other surface of said oxygen ionic conductor, and
(ii) a second component which detects the internal resistance of said sensor, said second component comprising at least an additional electrode placed on the surfaces of said oxygen ionic conductor for controlling the rate of oxygen permeation into said oxygen ionic conductor, (b) means for measuring the internal resistance of said limiting electric current oxygen concentration sensor, (c) means for measuring the limiting electric current which flows in said first component, (d) means for determining a temperature correction coefficient from the formula $$\alpha(T) = (T/To)^{-m}$$

wherein,

T represents absolute temperature

To represents reference temperature based on said internal resistance of said sensor, and (e) means for applying temperature correction to said limiting current flowing in said first component employing said temperature correction coefficient $\alpha(T)$.

17. A limiting electric current oxygen concentration detector as defined in claim 16, wherein the formula for the temperature correction coefficient $\alpha(T)$ is approximated as follows:

$$\alpha(T) = 1 + m(KTo/E)\{(R/Ro) - 1)\}.$$

18. A limiting electric current oxygen concentration detector as defined in claim 16, wherein the formula for the temperature correction coefficient $\alpha(T)$ is approximated as follows:

$$\alpha(T) = 1 + m(KTo/E)\{(R/Ro) - 1)\}.$$

19. A limiting electric current oxygen concentration detector comprising:

(a) a limiting electric current concentration oxygen concentration sensor comprising a first component which detects a limiting electric current of said sensor, said component comprising a cathode layer placed on one surface of an oxygen ionic conductor and an anode layer placed on the other surface of said oxygen ionic conductor, and a second component which detects internal resistance of said sensor, said second component comprising an additional electrode layer placed at a part of the surfaces of said oxygen ionic conductor, said additional electrode layer being covered with a member having a gas permeation larger than that of a member covering said first component for detecting the limiting electric current, (b) a current detection unit for measuring the limiting electric current by applying a voltage for detecting limiting electric current to said first component for detecting the limiting electric current, and (c) drive circuits means for driving said first and second components, comprising (1) a current control unit for controlling the current flowing in said second component to be smaller than that flowing in said first component, thereby preventing oscillation of said drive circuit means, (2) a specific voltage adder receiving a first voltage between said electrode layers of said first component and a second voltage between said electrode layers of said second component, for calculating a difference between the first and second voltages as a specific voltage ($\Delta V$), and (3) a drive circuit for amplifying the output from said specific voltage adder and driving said first and second components through said current control unit.

20. A limiting electric current oxygen concentration detector as defined in claim 19, wherein said current control unit comprises a first resistor connected between an ouput terminal of said drive circuit and said first component of said sensor, and a second resistor connected between said ouput terminal of said drive circuit and said first component of said sensor and having a resistance larger than that of said first resistor.

21. A limiting electric current oxygen concentration detector as defined in claim 20, wherein said specific voltage adder comprises a voltage source for generating a specific voltage, and an operational amplifier having a first input terminal connected in series with one electrode of said first component of said limiting electric current type oxygen concentration sensor through said voltage source, and a second input terminal connected to said electrode of said sensor, and said current detection unit comprises operating means for receiving potentials at two ends of said first resistor and determining the difference between the potentials, and generating a voltage proportional to the limiting electric current.

22. A limiting electric current oxygen concentration detector as defined in claim 19, wherein said second component comprises a pair of electrode layers separated from electrodes of said first component, said electrodes being connected to said drive circuit so that oxygen ion flows of said first and second components of said oxygen ionic conductor are opposite each other.

23. A limiting electric current oxygen concentration detector as defined in claim 19, comprising a first inverter between said second component and said drive circuit and a second inverter between said second component and said specific voltage adder so that oxygen ion flows of said first and second components of said oxygen ionic conductor are opposite each other.

24. A limiting electric current oxygen concentration detector comprising:

(a) a limiting electric current oxygen concentration sensor comprising a first component which detects limiting electric current of said sensor, said first component comprising a cathode layer placed on one surface of an oxygen ionic conductor and an anode layer placed on the other surface of said oxygen ionic conductor, a second component which detects internal resistance of said sensor, said second component comprising an additional electrode layer placed on a part of the surfaces of said oxygen ionic conductor, said first component allowing flow therein of a limiting electric current approximately identical to the limiting electric current in said second component, (b) means for measuring limiting electric current which flows in said first component, responsive to application of a voltage to said first component, and (c) means for driving each of said first and second components of said sensor comprising
 (1) an electric control unit for performing control so that a current less than the current flowing in said first component by a ratio flows in said second component, thereby driving said second component within a resistance domination range of said sensor, and
 (2) a voltage source for generating a specific voltage ($\Delta V$),
 a voltage amplifier for amplifying the voltage in said second component at an amplification factor which corresponds to said ratio for decreasing the current flowing through said second component, and
 a specific voltage adder having a first input terminal connected in series with one electrode of said first component through said voltage source and a second input terminal connected in series with an output terminal of said voltage amplifier.

25. A limiting electric current concentration detector as defined in claim 24, wherein said specific voltage adder comprises a power source for generating a specific voltage, an adder for adding a voltage between the electrodes of said first component and a specific voltage generated by said voltage source, a voltage amplifier for amplifying the voltage in said second component at an amplification factor corresponding to a ratio for decreasing the current flowing in said second component, and an operational amplifier for calculating the difference between the output from said adder and the output from said voltage amplifier and amplifying the difference.

26. A limiting electric current oxygen concentration detector comprising:
 (a) a limiting electric current oxygen concentration sensor, said sensor including an oxygen ionic conductor having major surfaces, a cathode on one of said surfaces, an anode on another of said surfaces, and means for controlling the rate of oxygen permeation into said oxygen ionic conductor,
 (b) an alternating voltage source for generating an alternating voltage in order to measure the internal resistance of said sensor,
 (c) voltage supplying means for superposing the alternating voltage and a direct voltage for measuring the limiting electric current on each other and supplying a superposed voltage to said sensor,
 (d) current detection means for detecting current flowing in said sensor by supplying the superposed voltage to said sensor,
 (e) alternating- and direct-current component separating means for separating an alternating-current component and a direct-current component from a detection output from said current detection means,
 (f) internal resistance calculating means for calculating the internal resistance of said sensor according to an output from said alternating voltage source and an alternating-current output component from said alternating- and direct-current component separating means,
 (g) voltage drop calculating means for calculating a value of voltage drop due to the direct current flowing in an internal resistor of said sensor according to the output from said internal resistance calculating means and an output from said alternating- and direct-current component separating means,
 (h) a first attenuator for attenuating an output from said voltage drop calculating means by a value, thereby preventing oscillation of a circuitry for driving said sensor, and
 (i) means for generating a voltage which is employed for measurement of a limiting current of said sensor, by addition of a specific voltage and the output voltage of the first attenuator.

27. A limiting electric current oxygen concentration detector as defined in claim 26, wherein
 said alternating- and direct-current component separating means comprises a high-pass filter for extracting the alternating-current component and a low-pass filter for extracting the direct-current component,
 said internal resistance calculating means comprises a subtracter for subtracting the output from said high-pass filter from the output from said alternating voltage source,
 said means for calculating the voltage-drop comprises a multiplier for multiplying the output from said subtracter by the output from said low-pass filter, and
 said means for generating a voltage for measurement of a limiting current comprises
  a voltage source for generating a voltage,
  a second attenuator for attenuating the voltage from said voltage source to generate the specific voltage, and
  an adder for adding the output from said first attenuator and the output from said second attenuator.

28. A limiting electric current oxygen concentration detector as defined in claim 27, wherein said internal resistance calculating means comprises a first rectifier for rectifying an alternating output from said alternating voltage source, a second rectifier for rectifying an alternating output from said high-pass filter, and a subtractor for subtracting an output from said second rectifier from an output from said first rectifier and driven by a direct current.

29. A limiting electric current oxygen concentration detector as defined in claim 26, further including
 (j) means for calculating the temperature according to the output of said means for measuring the internal resistance of said sensor according to the following formula, $$T = 1/\{(K/E) \log_e (R/Ro) + 1/To\}$$

wherein,
e represents the base of natural logarithms,
E represents activation energy,
K represents Boltzmann constant,
T represents absolute temperature,
To represents reference temperature
R represents internal resistance,
Ro represents internal resistance at the temperature To,
 (k) means for setting a temperature, and
 (l) means for heating said sensor according to the difference between said calculated value of temperature of said sensor and said set temperature,
 (m) means for controlling current from a power source to said means for heating said sensor.

30. A limiting electric current oxygen concentration detector as defined in claim 26, further comprising means for calculating a temperature correction coefficient from the formula $$\alpha(T) = (T/T_o)^{-m}$$

wherein,

T represents absolute temperature,

To represents reference temperature, based on said internal resistance of said sensor, and means for applying temperature correction to said amount of limiting current flowing in said sensor, employing said temperature correction coefficient $\alpha(T)$.

* * * * *